(12) United States Patent
Raveh et al.

(10) Patent No.: US 10,408,740 B2
(45) Date of Patent: Sep. 10, 2019

(54) METHOD FOR HUANGLONGBING (HLB) DETECTION

(71) Applicants: The State of Israel, Ministry of Agriculture & Rural Development Agricultural Research Organization, Rishon Lezion (IL); University of Florida Research Foundation, Incorporated, Gainesville, FL (US)

(72) Inventors: Eran Raveh, Midreshet Ben Gurion (IL); Won Suk Lee, Gainesville, FL (US); Alireza Pourreza, Gainesville, FL (US); Reza John Ehsani, Lake Alfred, FL (US)

(73) Assignees: The State of Israel, Ministry of Agriculture & Rural Development Agricultural Research Organization, Rishon Lezion (IL); UNIVERSITY OF FLORIDA RESEARCH FOUNDATION, INCORPORATED, Gainesville, FL (US)

(*) Notice: Subject to any disclaimer, the term of this patent is extended or adjusted under 35 U.S.C. 154(b) by 46 days.

(21) Appl. No.: 15/318,983

(22) PCT Filed: Jun. 15, 2015

(86) PCT No.: PCT/IL2015/050603
§ 371 (c)(1),
(2) Date: Dec. 15, 2016

(87) PCT Pub. No.: WO2015/193885
PCT Pub. Date: Dec. 23, 2015

(65) Prior Publication Data
US 2017/0131200 A1    May 11, 2017

Related U.S. Application Data

(60) Provisional application No. 62/012,366, filed on Jun. 15, 2014.

(51) Int. Cl.
| | | |
|---|---|---|
| *G01N 21/23* | (2006.01) | |
| *G01N 21/21* | (2006.01) | |
| *G01N 21/84* | (2006.01) | |

(52) U.S. Cl.
CPC ............ *G01N 21/23* (2013.01); *G01N 21/21* (2013.01); *G01N 21/84* (2013.01);
(Continued)

(58) Field of Classification Search
CPC ...................................................... G01N 21/23
(Continued)

(56) References Cited

U.S. PATENT DOCUMENTS 6,024,449 A * 2/2000 Smith ..................... A61B 3/107
                                                          351/212
6,324,298 B1 * 11/2001 O'Dell ............... G01N 21/9501
                                                         257/E21.53
(Continued)

OTHER PUBLICATIONS

Chika C. Nwugo, Study on Citrus Responses to Huanglongbing.., Jun. 19, 2013; vol. 6; Abstract.*
(Continued)

*Primary Examiner* — Kara E. Geisel
*Assistant Examiner* — Omar H Nixon
(74) *Attorney, Agent, or Firm* — Mark M Friedman

(57) ABSTRACT

A sensing system identifies Huanglongbing (HLB) symptoms in leaves of citrus trees in real time and differentiates them from nutrient deficiencies.

29 Claims, 23 Drawing Sheets

(52) U.S. Cl.
CPC ............... *G01N 2021/8466* (2013.01); *G01N 2201/0221* (2013.01); *G01N 2201/0683* (2013.01)

(58) Field of Classification Search
USPC .......................................................... 356/369
See application file for complete search history.

(56) References Cited

U.S. PATENT DOCUMENTS

| | | | |
|---|---|---|---|
| 6,695,209 B1* | 2/2004 | La ...................... | G06K 7/10851 235/462.2 |
| 2008/0167552 A1* | 7/2008 | Bouchevreau ......... | A61B 6/481 600/431 |
| 2009/0015835 A1* | 1/2009 | Balakrishnan ............ | G01J 3/02 356/369 |
| 2012/0018356 A1 | 1/2012 | Jalink | |
| 2012/0123681 A1* | 5/2012 | Milori ................ | G01N 21/6486 702/2 |
| 2013/0325346 A1 | 12/2013 | McPeek | |
| 2014/0127672 A1 | 5/2014 | Davis et al. | |
| 2014/0127718 A1* | 5/2014 | Ma .................... | G01N 33/56911 435/7.32 |

OTHER PUBLICATIONS

A. Hocquellet, P. Toorawa, J. M. Bove, and M. Garner, "Detection and identification of the two *Candidatus liberobacter* species associated with citrus huanglongbing by PCR amplification of ribosomal protein genes of the beta operon" Molecular and Cellular Probs,13, 373-379. Jul. 1999 Academic Press.

K. A. McMahon, "Practical Botany—the Maltese Cross" Tested Studies for Laboratory Teaching, 25:352-357, 2004. http://www.zoo.utoronto.ca/able.

L. G. Marcassa, M. C. G. Gasparoto, J. Belasque Jr., E. C. Lins, F. Dias Nunes, and V. S. Bagnato "Fluorescense spectroscopy applied to orange trees" Laser Methods in Biology and Medicine, Laser Physics 16(5):884-888, 2006.

Li, W., J. S. Hartung and L. Levy, "Quantitative real-time PCR for detection and identification of *Candidatus liberibacter* species associated with citrus huanglonabing" journal of Microbiological Methods, 66: 104-115, Jan. 2006. Elsevier.

Ashish R Mishra, Reza Ehsani, Won Suk Lee, Gene Albrigo "Spectral Characteristics of Citrus Greening (Huanglongbing)" Jun. 2007 ASAE Annual Meeting 073056.

J Belasque Jr, M. C. G. Gasparoto, L. G. Marcassa "Detection of mechanical and disease stresses in citrus plants by fluorescence spectroscopy" Applied Optics 47(11): 1922-1926, Apr. 10, 2008. Optical Society of America.

D. G. Kim, T. F. Burks, A. W. Schumann, M. Zekri, X. Zhao, and J. Qin "Detection of Citrus Greening Using Microscopic Imaging" Agricultural Engineering International: the CIGR Ejournal, Jun. 2009.

E. C. Lins, J. Belasque Jr, and L. G. Marcassa "Detection of citrus canker in citrus plants using laser induced fluorescence spectroscopy" Precision Agriculture, 10:319-330, Aug. 2009.

S. Sankaran, R. Ehsani, and E. Etxeberria "Mid-infrared spectroscopy for detection of Huanglongbing (greening) in citrus leaves" Talanta 83:574-581, Oct. 2010. Elsevier.

Xiuhua Li, Won Suk Lee, Minzan Li, Reza Ehsani, Ashish R Mishra, Chenghai Yang, Robert L Mangan "Comparison of different detection methods for citrus greening disease based on airborne multispectral and hyperspectral imagery" 2011 Louisville, Kentucky, Aug. 7-10, 2011 1110570. (doi:10.13031/2013.37734).

A. Mishra, D. Karimi, R. Ehsani, L. G. Albrigo "Evaluation of an active optical sensor for detection of Huangiongbing (HLB) disease" Biosystems Engineering, v.110, No. 3, Nov. 2011, p. 302(8) (ISSN: 1537-5110).

F. M. V. Pereira, D. M. B. P. Milori, E. R. Pereira-Filho, A. L. Venibcio, M. D. S. T. Russo, M. C. D. B. Cardinali, P. K. Martins, and J. Fretas-Astua "Laser-induced fluorescence imaging method to monitor citrus greening disease" Computers and Electronics in Agriculture 79: 90-93, Aug. 2011.

S. Sankaran and R. Eshani "Visible-near infrared spectroscopy based citrus greening detection: Evaluation of spectral feature extraction techniques" Crop Protection 30:1508-1513, Jul. 2011. Elsevier.

S. Sankaran, A. Mishra, J. M. Maja, and R. Ehsani "Visible-near infrared spectroscopy for detection of Huangiongbing in citrus orchards" Computers and Electronics in Agriculture, 77:127-134, Mar. 2011. Elsevier.

A. H. Putnam, "Florida Agriculture by the Numbers" Florida Department of Agriculture and Consumer Services, Tallahassee, FL. 2012.

Pedro Gonzalez, Jose Reyes-De-Corcuera, Ed Etxeberria "Characterization of leaf starch from HLB-affected and unaffected-girdled citrus trees" Physiological and Molecular Plant Pathology, vol. 79, Jul. 2012, pp. 71-78.

Arun Kumar, Won Suk Lee, Reza J. Ehsani, L. Gene Albrigo, Chenghai Yang, Robert L. Mangan, "Citrus greening disease detection using aerial hyperspectral and multispectral imaging techniques," Journal of Applied Remote Sensing 6(1), 063542 (Jun. 1, 2012) https://doi.org/10.1117/1.JRS.6.063542.

Mishra, A. R., D. Karimi, R. Ehsani, and W. S. Lee, "Identification of citrus greening (HBL) using a VIS-NIR spectroscopy technique" Trans. ASABE, 55(2): 711-720, 2012. ISSN 2151-0032.

Li, H., W.S. Lee, R. Wang, R. Ehsani, and C. Yang "Special angle mapper (SAM) based citrus greening disease detection using airborne hyperspectral imaging" 11th International Conference on Precision Agriculture, Indianapolis, Indiana. 2012.

Li, X. H., W. S. Lee, M. Z. Li, R. Ehsani, A. R. Mishra, C. H. Yang, and R. L. Mangan "spectral difference analysis and airborne imaging classification for citrus greening infected trees" Computers and Electronics in Agriculture, 83:32-46, Jan. 2012.

* cited by examiner

FIG. 3A
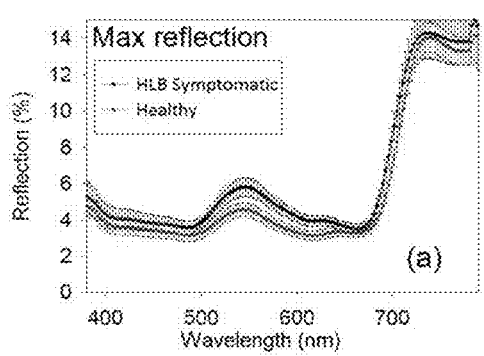
(a)
FIG. 3B
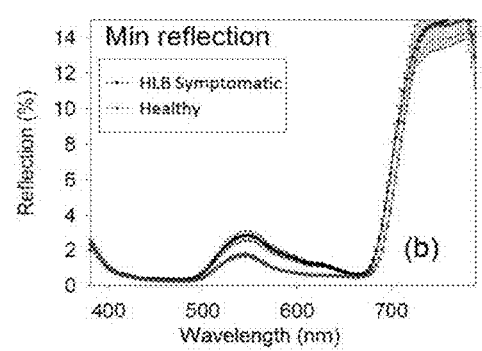
(b)
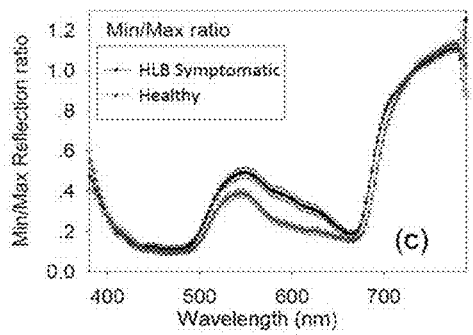
(c)
FIG. 3C
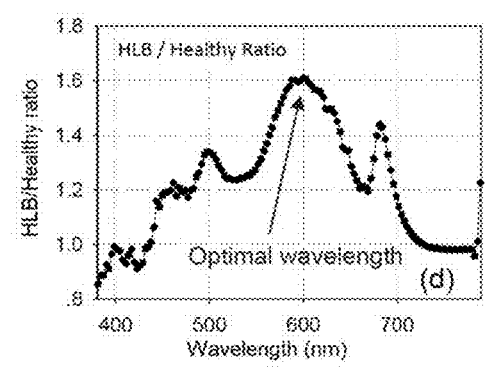
(d)
FIG. 3D

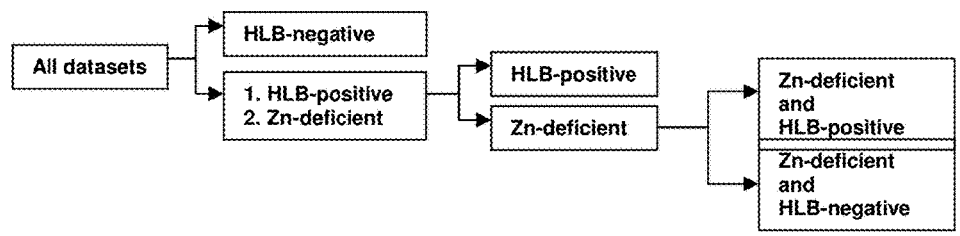
FIG. 15
FIG. 16A
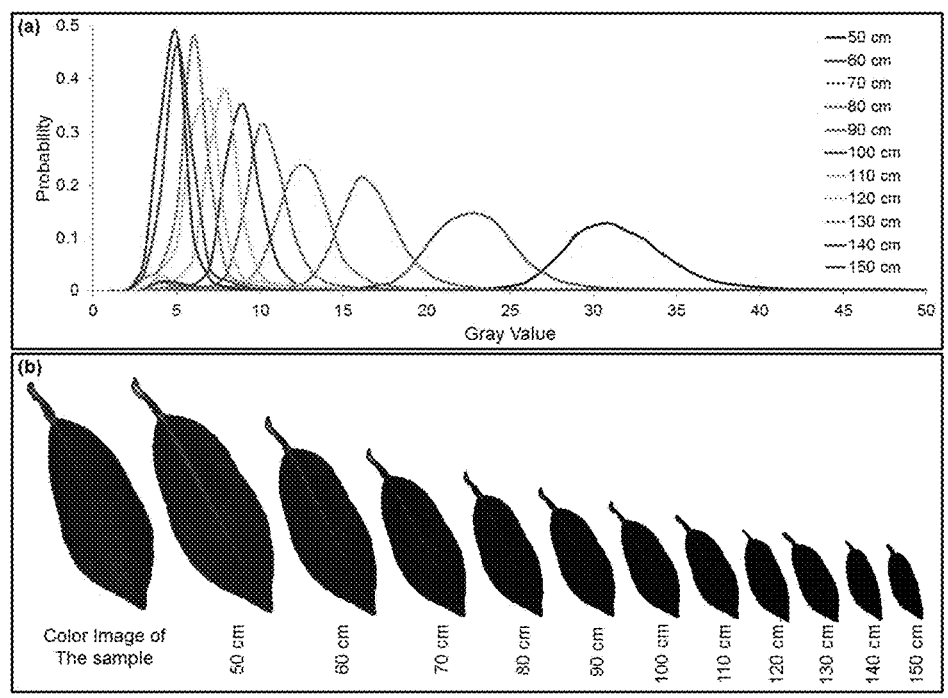
FIG. 16B

METHOD FOR HUANGLONGBING (HLB) DETECTION

CROSS REFERENCES TO RELATED APPLICATIONS

This application is related to and claims priority from commonly owned U.S. Patent application Ser. No. 62/012,366, entitled: Method for HLB Detection, filed on Jun. 15, 2014, the disclosure of which is incorporated by reference in its entirety herein.

TECHNICAL FIELD

The present invention is directed to methods and systems for detecting diseased trees, and in particular the disease known as Citrus greening or Huanglongbing (HLB).

BACKGROUND

Citrus is a very important crop in Florida. In the 2010-2011 season, 7.4 million tons of citrus were produced in Florida which included 63 percent of the total United States citrus production, as reported by Putnam (Putnam, A. H. 2012, "Florida Agriculture by the Numbers" in, *Florida Department of Agriculture and Consumer Services*, Tallahassee, Fla.) (Putnam 2012). Citrus greening or Huanglongbing (HLB), also known as yellow shoot disease, is a very severe disease which has decreased the citrus production in Florida. The disease is caused by the insect-vectored α-protobacterium *Candidiatus Liberibacter* Asiaticus, as reported by Mishra, et al. (Mishra, A., R. Ehsani, G. Albrigo, and W. S. Lee, 2007, "Spectral Characteristics of Citrus Greening (Huanglongbing)" in, *ASABE Paper No.* 073056, Minneapolis, Minn.: ASABE) (Mishra, et al. 2007). Blotchy mottle on leaf, yellow shoots, inverted color, and uneven fruits are some of the disease symptoms; however, it is unlikely that they would appear altogether in the same tree. The disease reduces the production, degrades the fruit quality and finally destroys the tree, as reported by Gonzalez, et al. (Gonzalez, P., J. Reyes, DeCorcuera, and Etxeberria, E., 2012, "Characterization of leaf starch from HLB-affected and unaffected-girdled citrus trees" in, *Physiological and Molecular Plant Pathology,* 79: 71-78) (Gonzalez, et al. 2012). Although, no practical treatment has been reported for the disease yet, detecting and removing the infected trees can avoid spreading the infection to the other trees.

Many studies have focused on HLB detection and several methods have been tried for this purpose. In 1996, polymerase chain reaction (PCR) method was proven to be an effective HLB detection method, as reported by Hocquellet, et al. (Hocquellet, A., P. Toorawa, J. M. Bove, and M. Garnier, 1999, "Detection and identification of the two *Candidatus Liberobacter* species associated with citrus huanglongbing by PCR amplification of ribosomal protein genes of the beta operon" in, *Mol. Cell Probes,* 373-379. England: 1999 Academic Press) (Hocquellet, et al. 1999). Li, et al. (Li, W., J. S. Hartung, and L. Levy, 2006, "Quantitative real-time PCR for detection and identification of *Candidatus Liberibacter* species associated with citrus huanglongbing" in, *Journal of Microbiological Methods,* 66(1): 104-115)(Li, et al. 2006) also developed a real-time and quantitative PCR assay method and examined it successfully for HLB confirmation in Florida. However, the PCR method is a laboratory based approach which is expensive and time consuming, and so cannot be used in a real-time in-field application. Currently, growers try to find noticeable HLB symptoms to identify the infected trees. However, it is not easy to differentiate the symptoms resulting from nutrient deficiency and HLB.

Early and quick detection has been considered widely in recent studies. The use of near-infrared and mid-infrared spectroscopy, for example, has been investigated to identify the HLB infected trees from healthy or nutrient deficient ones under laboratory and field conditions, as reported by Mishra, et al. (Mishra, et al. 2007); Mishra, et al. (Mishra, A., D. Karimi, R. Ehsani, and L. G. Albrigo, 2011, "Evaluation of an active optical sensor for detection of Huanglongbing (HLB) disease" in, *Biosystems Engineering,* 110: 302-309) (Mishra, et al. 2011); Mishra, et al. (Mishra, A. R., D. Karimi, R. Ehsani, and W. S. Lee, 2012, "Identification of citrus greening (HLB) using a VIS-NIR spectroscopy technique" in *Trans. ASABE,* 55(2): 711-720) (Mishra et al. 2012); Sankaran and Eshani (Sankaran and Eshani, 2011, "Visible-near infrared spectroscopy based citrus greening detection: Evaluation of spectral feature extraction techniques" in *Crop Protection,* 30: 1508-1513) (Sankaran and Ehsani 2011); Sankaran, et al. (Sankaran, S., R. Ehsani, and E. Etxeberria, 2010, "Mid-infrared spectroscopy for detection of Huanglongbing (greening) in citrus leaves" in *Talanta,* 83: 574-581)(Sankaran, et al. 2010); and, Sankaran, et al. (Sankaran, S., A. Mishra, J. M. Maja, and R. Ehsani, 2011, "Visible-near infrared spectroscopy for detection of Huanglongbing in citrus orchards" in, *Computers and Electronics in Agriculture,* 77(2): 127-134)(Sankaran, et al. 2011).

Airborne hyperspectral and multispectral imaging approaches have also been employed in HLB disease detection, as reported by Kumar, et al. (Kumar, A., W. S. Lee, R. J. Ehsani, L. G. Albrigo, C. H. Yang, and R. L. Mangan, 2012, "Citrus greening disease detection using aerial hyperspectral and multispectral imaging techniques" in *Journal of Applied Remote Sensing,* 6(1)) (Kumar, et al. 2012); Li, et al. (Li, H., W. S. Lee, R. Wang, R. Ehsani, and C. Yang, 2012, "Spectral angle mapper (SAM) based citrus greening disease detection using airborne hyperspectral imaging" in, 11*th International Conference on Precision Agriculture,* Indianapolis, Ind.) (Li, Lee and Wang, et al. 2012); Li, et al. (Li, X., W. S. Lee, M. Li, R. Ehsani, A. R. Mishra, C. Yang, and R. L. Mangan, 2011, "Comparison of different detection methods for citrus greening disease based on airborne multispectral and hyperspectral imagery" in *ASABE Paper No.* 1110570, Louisville, Ky.: ASABE)(Li, et al. 2011); and, Li, et al. (Li, X. H., W. S. Lee, M. Z. Li, R. Ehsani, A. R. Mishra, C. H. Yang, and R. L. Mangan, 2012, "Spectral difference analysis and airborne imaging classification for citrus greening infected trees" in, *Computers and Electronics in Agriculture,* 83: 32-46) (Li, Lee, and Li, et al. 2012). Based on their results, the difference between the reflectance signatures of HLB and healthy trees can be used to highlight the severely symptomatic areas. Some researchers examined the capability of laser-induced fluorescence spectroscopy and imaging for citrus disease identification, as reported by Belasque, Jr., et al. (Belasque, Jr., J., M. Gasparoto, and L. Marcassa, 2008, "Detection of mechanical and disease stresses in citrus plants by fluorescence spectroscopy" in, *Applied Optics* 47(11): 1922-1926) (Belasque, Jr., et al. 2008); Lins, et al. (Lins, E. C., J. Belasque Jr, and L. G. Marcassa, 2009, "Detection of citrus canker in citrus plants using laser induced fluorescence spectroscopy" in, *Precision Agriculture,* 10(4): 319-330) (Lins, et al. 2009); and, Marcassa, et al. (Marcassa, L., M. Gasparoto, J. Belasque Jr, E. Lins, F. D. Nunes, and V. Bagnato, 2006, "Fluorescence spectroscopy applied to orange trees" in, *Laser Physics,*

16(5): 884-888) (Marcassa, et al. 2006). Pereira, et al. (Pereira, F. M. V., D. M. B. P. Milori, E. R. Pereira-Filho, A. L. Venincio, M. D. S. T. Russo, M. C. D. B. Cardinali, P. K. Martins, and J. Freitas-Astúa, 2011, "Laser-induced fluorescence imaging method to monitor citrus greening disease" in *Computers and Electronics in Agriculture,* 79: 90-93) (Pereira, et al. 2011), for instance, achieved an accuracy of 95% for detection of HLB symptomatic in early stages from healthy samples. Microscopic images from the citrus leaves turned out to be a capable method to identify the HLB symptoms from nutrient deficiencies, as reported by Kim, et al. (Kim, D. G., T. F. Burks, A. W. Schumann, M. Zekri, X. Zhao, and Q. Jianwei, 2009, "Detection of Citrus Greening Using Microscopic Imaging" in, *Agricultural Engineering International: the CIGR Ejournal*) (Kim, et al. 2009). Kim, et al. (Kim, et al. 2009) extracted color co-occurrence features from the leaf images and obtained the overall accuracy of 97% using a selected feature-set and a discriminant classifier.

Gonzalez et al. (Gonzalez, et al. (2012) proved that the starch content in HLB-infected leaves increases compared to the healthy ones. Their results indicated that the accumulated starch in HLB symptomatic leaves were not biochemically similar to the healthy leaves' starch which was accumulated as a result of a mechanical injury. Therefore, the starch measurement in citrus leaves can be considered as a HLB detection method. Furthermore, starch was determined to be able to rotate the polarization planer of light by McMahon (McMahon, K. A., 2004, "Practical Botany—The Maltese Cross" in, *Tested Studies for Laboratory Teaching,* 25: 352-357) (McMahon, 2004). This capability of starch on polarized light was previously evaluated by the authors and an imaging system which was able to highlight the starch accumulated on HLB leaf was developed. The system was examined for Hamlin variety of citrus in four classes of healthy, HLB symptomatic, zinc deficient, and HLB symptomatic-zinc deficient samples and the overall accuracy of 90% was achieved. The classification rate increased to 93% when the HLB detection was considered as the purpose of the classification.

SUMMARY

Embodiments of the present invention provide a portable and real-time sensing system, which identifies HLB symptoms, and differentiates them from nutrient deficiencies.

In other embodiments of the invention, citrus canopies may be illuminated with polarized light at various wavelengths. Polarized light may be rotated with angles different than 90°. For each angle of rotation, highest reflectance intensity may be read by adjusting the angle between the filter mounted in front of the lamp and the filter through which reflected light passes.

Embodiments of the present invention provide for starch determination in citrus leaves are such that gray values from images obtained from reflected polarized light have a gray value of above 52 on a gray scale range of 0-255 obtained, for example, by a vision-based sensor. The gray values pairwise Fisher Ratio of the examined tree, e.g., leaves thereof, and a healthy tree, e.g., leaves therefor, is lower than 15. The aforementioned values are indicative of the examined tree (tree in question) being a starch accumulation-deficient tree, and an HLB candidate.

Embodiments of the present invention are directed to a method for detecting starch accumulation-deficient trees. The method comprises: illuminating at least one tree leaf with a polarized light at a first reference plane; obtaining light reflected from the at least tree leaf having been polarized at a second reference plane, the second reference plane at a predetermined angle relative to the first reference plane; and, generating at least one image from the obtained light, and analyzing the image for a correlation to starch accumulation in the at least one tree leaf.

Optionally, the correlation to starch accumulation is in accordance with predetermined starch concentration values in leaves.

Optionally, the method additionally comprises obtaining a starch concentration value for the at least one tree leaf, the obtained starch concentration value based on the correlation of starch accumulation in the at least one tree leaf with the predetermined starch concentrations, and analyzing the obtained starch concentration value with respect to starch concentration values of leaves of starch-accumulation deficient trees including Huanglongbing (HLB)-symptomatic trees.

Optionally, the at least one image includes gray values and the gray values are analyzed for the correlation to starch accumulation in the at least one tree leaf.

Optionally, the at least one image includes pixels, and each of the pixels corresponds to at least one of the gray values.

Optionally, predetermined angle for the second reference plane is approximately 90 degrees from the first reference plane.

Optionally, the polarized light is at a wavelength of approximately 550 nanometers (nm) to approximately 650 nm.

Optionally, the polarized light is at a wavelength of approximately 590 nm to approximately 610 nm.

Optionally, the polarized light is at a wavelength of approximately 600 nm.

Optionally, the polarized light is at a wavelength of approximately 591 nm.

Optionally, the at least one tree leaf is from a Citrus tree.

Embodiments of the invention are directed to a system for detecting starch accumulation-deficient trees. The system comprises: a polarized light source, for illuminating a tree leaf, the polarized light from the polarized light source emitted at a first reference plane; a polarizer at second plane at an angle relative to the first reference plane; at least one sensor in communication with the polarizer for detecting the intensity of received reflected light which is filtered by the polarizer; an image processor in communication with the at least one sensor for producing images based on the intensity of the received reflected light; and, an image analyzer configured analyzing the image for a correlation to starch accumulation in the at least one tree leaf.

Optionally, the image analyzer is configured for correlating the starch-accumulation with starch accumulation values for starch accumulation deficient trees including Huanglongbing (HLB)-symptomatic trees.

Optionally, the at least one sensor, and the image processor are associated with a charge coupled device (CCD) camera, and the image processor generates images from the received reflected light.

Optionally, the image processor generates an image including pixels, each of the pixels including at least one gray scale value, each of the gray scale values with respect to a reference gray scale.

Optionally, the image analyzer includes at least one processor for analyzing reach of the pixel gray scale values with respect to the reference gray scale, the reference gray scale including gray scale values associated with leaves of a Huanglongbing (HLB)-symptomatic tree.

Optionally, the polarized light source includes a light source coupled to at least one first polarizing filter oriented to define the first reference plane.

Optionally, the polarizer includes at least one second polarized filter at the second plane.

Optionally, the second plane is oriented approximately 90 degrees from the first reference plane.

Optionally, the light source emits light at a wavelength of approximately 550 nanometers (nm) to approximately 650 nm.

Optionally, the light source emits light at a wavelength of approximately 590 nm to approximately 610 nm.

Optionally, the light source emits light at a wavelength of approximately 600 nm.

Optionally, the light source emits light at a wavelength of approximately 591 nm.

Embodiments of the invention are directed to a computer usable non-transitory storage medium having a computer program embodied thereon for causing a suitable programmed system to detect birefringent materials in a acquired image, by performing the following steps when such program is executed on the system. The steps comprise: generating gray scale images with gray values from acquired images of citrus leaves; translating the gray values to at least one scatterplot; and, applying predetermined thresholds on the scatterplot for starch accumulation values for citrus leaves.

Optionally, the applying thresholds includes, applying a threshold for starch accumulation values associated with leaves of a Huanglongbing (HLB)-symptomatic tree.

Optionally, the gray values include the mean and standard deviation (SD), which for the respective vertical (y) and horizontal (x) axes of a histogram.

Optionally, the applying thresholds includes, applying a threshold for starch accumulation values associated with leaves of a Huanglongbing (HLB)-symptomatic tree.

Optionally, the predetermined thresholds are determined by machine learning.

Optionally, the acquired images include pixels, each of the pixels having a gray value.

Unless otherwise defined herein, all technical and/or scientific terms used herein have the same meaning as commonly understood by one of ordinary skill in the art to which the invention pertains. Although methods and materials similar or equivalent to those described herein may be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF DRAWINGS

Some embodiments of the present invention are herein described, by way of example only, with reference to the accompanying drawings. With specific reference to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Attention is now directed to the drawings, where like reference numerals or characters indicate corresponding or like components. Throughout this document, the drawings are referred to by the identifiers "Figure," "FIG.," regardless of case, which are used interchangeably herein. In the drawings:

FIGS. 3A-3D are charts of the detection of an HLB-symptomatic canopy of Example 2;

FIG. 15 is a diagram of a classification model for Example 3;

FIG. 16A are histograms of leaf samples acquired at various distances in Example 3;

FIG. 16B shows leaf sample colors from Example 3;

DETAILED DESCRIPTION

I. Introduction

Figure 1:
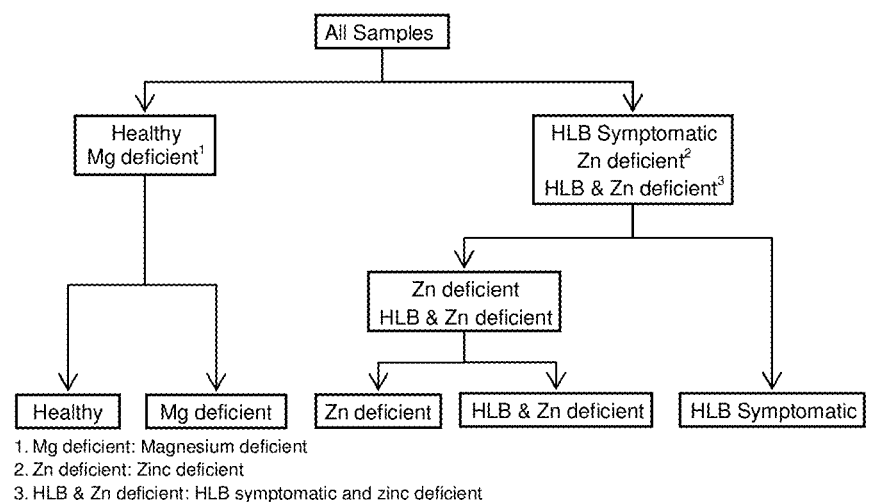
FIG. 1 is a diagram of a classification model for Example 1.

The present invention relates to method for detecting trees whose leaves possess over-quantities of starch. Embodiments of the present invention also relate to methods for detecting the greening in symptomatic trees. For detecting the greening symptomatic trees, one needs to irradiate the trees with polarized light (using a projector together with a polarized filter that will be mounting in front of the projector) and read the intensity of the light reflection from the tree. In front of the sensor that will be use to measure the reflection intensity we will put a second polarized filter that its polarization planar will be perpendicular to the polarization planar of projector polarized filter.

In embodiments of the invention, processes are performed to distinguish greening of citrus trees. For example, the processes performed are on or more of: 1) illuminating a tree canopy in conditions of darkness with polarized light at a wavelength of between 550 to 650 nm (nanometers), such as approximately 600 nm, and approximately 591 nm; 2) read the reflection light intensity from the leaves of the tree canopy with a light sensor mounted with a polarized filter such that polarization plane is approximately perpendicular to the polarization plane of the light used for illuminating the canopy (measuring of min. reflection); and, 3) in cases where gray values are above 52 (on a gray scale ranging between 0 to 255), the tree is an HLB candidate.

In other embodiments, should the pixels reading of the minimum (min)-reflection be greater by 60% or more of those of a healthy tree, the tree is characterized as greening-symptomatic-tree candidate, such that leaves of this candidate tree should be analyzed by PCR (Polymerase Chain Reaction), for confirmation of the leaves as those of a greening-symptomatic-tree.

II. Determining the Optimum Wavelength for Polarization

The inventors have determined that the polarization planer rotation caused by the starch accumulated in the HLB infected citrus leaf can be effectively used for HLB detection. As a result, it was determined that the wavelength of 591 nm for a light beam was a potential waveband in the visible range for the disease detection. The processes from which these determinations were made are provided in Examples 1 and 2, below.

The inventors further determined that the use of 591 nm light was optimal for analysis of citrus leaves plants for HLB detection. The processes from which these determinations were made are provided in Example 2, below.

Example 1

In this Example, the citrus variety (Valencia) was to confirm the robustness of the system, provided in this study, e.g., this Example, "study" and "Example" used interchangeably in this Example below. One more class of magnesium deficient samples is also added to test the system in a more challenging situation.

The main objective of this study was to evaluate a machine vision based sensing system for identification of HLB symptomatic citrus leaves from healthy and nutrient deficient samples. The particular objectives were: 1) to compare the performance of the proposed method for two different varieties of citrus; 2) to evaluate the system capability of discriminating between HLB and nutrient deficiency symptoms; and, 3) to assess the capabilities of image textural features for HLB detection.

Materials and Methods

The starch accumulation in the HLB symptomatic leaves can be emphasized in images captured with a narrow band illumination and a polarizing filter. Because starch rotates the polarization planer of the light, this effect can be used to differentiate between HLB symptoms and nutrient deficiency symptoms. In May 2010, a preliminarily experiment was conducted in the Citrus Research and Education Center (CREC) in Lake Alfred and it was determined that the maximum and minimum polarization rotation caused by accumulated starch in HLB symptomatic leaves mostly happened at 600 nm and 400 nm wavebands, respectively. Based on these results, an imaging system was designed and tested for the Hamlin variety of citrus. The classification results showed that the proposed system is able to differentiate HLB symptomatic leaves from healthy and zinc deficient leaves. In order to confirm the reliability of the proposed method, it was examined with a different citrus variety (Valencia) and also additional nutrient deficiency classes.

Data Collection

A total of 96 citrus leaf samples of the Valencia variety in four classes of healthy, HLB symptomatic, zinc deficient, and magnesium deficient leaves were collected from the CREC grove in December, 2012. In order to identify the HLB infected samples, a PCR test, as per Sankaran, et al. (Sankaran, et al. 2010), was conducted for each individual leaf in the diagnostic laboratory of the United States Sugar Corporation (USSC)/Southern Gardens located in Clewiston, Fla. The starch concentration for each leaf was also measured in μg starch/mm$^2$ based on the method introduced by Gonzalez et al. (Gonzalez et al. 2012). The starch concentration value of 5 μg/mm$^2$ was defined as the threshold to evaluate the HLB infection status of samples, as it was suggested by them.

Image Acquisition

An image acquisition system, such as that shown in FIG. 4 and described in Example 2 below, as well as immediately below, took citrus leaf images in a controlled illumination system. Four high power LEDs (LZ1-00A100, LED Engine, San Jose, Calif.) at 591 nm were used for illumination purpose. A monochrome camera (EBC-B100G, EZ SPY CAM, Los Angeles, Calif.) was also used to capture the leaf reflectance with a good spectral sensitivity characteristic at 591 nm (Sony CCD image sensors, ICX404AL) and a horizontal resolution of 420 TV lines. Since the camera output was analog, a USB frame grabber (Model 2255, Sensory, Tigard, Oreg.) was employed to produce digital images with a 640×480 pixel resolution. Two polarizing filters (Visible linear polarizing laminated film, Edmund Optics, Barrington, N.J.) in perpendicular directions were employed; one was placed in front of the LEDs and the other was mounted in front of the camera lens. Therefore, the camera was able to capture the minimum reflectance of the leaf; however, since the HLB symptomatic leaves contained starch accumulation, which rotates the polarization planer of the light, the HLB symptomatic areas were expected to be highlighted with brighter gray levels. The imaging and illumination components were assembled in a wooden box with 16 cm length, 14 cm width, and 47.5 cm height. The distance between the camera lens and the leaf was 39 cm.

Preprocessing

Automatic gain control (AGC) is a camera capability which increases the average gain if the image is too dim and reduces the gain if the image is too bright, as per Fowler (Fowler, K. R., 2004, "Automatic Gain Control for Image-Intensified Camera, Instrumentation and Measurement" in, *IEEE Transactions*, 53(4): 1057-1064) (Fowler 2004). AGC is typically a non-deactivatable feature for the commercial cameras. Since the real reflectance of the leaf was required for this study, the AGC effect was not favorable. In order to cancel the AGC effect on the images, a similar background was used in all the images. Then, they were calibrated using a ratio of an average of background gray values in all the images to an average of those in each image, as a gain multiplier for each individual image.

Feature Extraction

MATLAB™ (version R2011a, MathWorks™, Natick, Mass., USA) software was used for all steps of feature extraction, features selection, data analysis, and classification. A total of 30 textural features in four groups were extracted from the images. The features included statistical histogram features from gray level, local binary pattern (LBP), and local similarity pattern (LSP) matrices as well as gray level cooccurrence matrix (GLCM) features. Equations (Eqs.) 1 through 8 show the formulas which were used to extract the statistical features from the normalized histogram (p(i)) of each image's gray level matrix when the gray level (ranged from 0 to 255) was shown with i.

$$\text{Mean } \mu = \Sigma_i i p(i) \quad (1)$$

$$\text{Standard Deviation (STD) } \sigma = \sqrt{\Sigma_i (i-\mu)^2 p(i)} \quad (2)$$

$$\text{Third Moment } \Sigma_i (i-\mu)^3 p(i) \quad (3)$$

$$\text{Smoothness } 1 - 1/(1+\sigma^2) \quad (4)$$

$$\text{Uniformity } \Sigma_i p(i)^2 \quad (5)$$

$$\text{Entropy } -\Sigma_i p(i) \log\{p(i)\} \quad (6)$$

$$\text{Maximum Gray Level Probability } (i|p(i)=\max) \quad (7)$$

$$\text{Range } \{\max(i|p(i)\neq 0) - \min(i|p(i)\neq 0)\} \quad (8)$$

LBP is an innovative image textural descriptor which was first introduced by Ojala, et al. (Ojala, T., M. Pietikäinen, and D. Harwood, 1996, "A comparative study of texture measures with classification based on featured distributions" in, *Pattern Recognition*, 29(1): 51-59) (Ojala, et al. 1996). In this method each matrix element in a 3×3 neighborhood is compared to the central element and substituted by 1 if it is greater than the value of the central element, and by 0 if it is smaller than the central element. The threshold values are then assumed to be an 8-bit binary number and its corresponding decimal number substitutes the central element. Similarly, in LSP the neighborhood elements are compared with the central element; however, the relation between each neighbor element and the central element is described with a 2-bit code. In this method the neighborhood elements are substituted with 00, 01, or 10 if they are below, within or above a defined similarity range, respectively. Then each element code is multiplied by its respective weight, as per Pourreza, et al. (Pourreza, H. R., M. Masoudifar, and M. Manaf Zade, 2011, "LSP: Local similarity pattern, a new approach for rotation invariant noisy texture analysis" in *18th IEEE International Conference on Image Processing (ICIP)*, 837-840. Brussels, Belgium: IEEE) (Pourreza, et al. 2011). LBP and LSB employ the same approach to prevent the variation caused by code rotation. The rotational invariance is obtained by rotating the codes to achieve their least possible decimal values. The equations 1 through 6 were also used to extract the statistical features from the normalized histogram of LBP and LSP matrices.

GLCM is a 256×256 matrix (for an 8-bit gray level image) in which each (i,j) element shows the number of times that two gray values of i and j were adjacent in any of four principal directions (0°, 45°, 90°, and 135°). Equations 9 through 18 show the formulas which were used to extract the textural features from the normalized GLCM matrix, as per Pourreza, et al. (Pourreza, A., H. Pourreza, M. H. Abbaspour-Fard, and H. Sadrnia, 2012, "Identification of nine Iranian wheat seed varieties by textural analysis with image processing" in, *Computers and Electronics in Agriculture*, 83: 102-108, http://dx.doi.org/10.1016/j.compag.2012.02.005) (Pourreza and Pourreza, et al. 2012).

$$\text{Mean } \mu = \Sigma_{i,j} i g(i,j) \quad (9)$$

$$\text{Variance } \sigma^2 = \Sigma_{i,j} (i-\mu)^2 g(i,j) \quad (10)$$

$$\text{Entropy } -\Sigma_{i,j} g(i,j) \log\{g(i,j)\} \quad (11)$$

$$\text{Uniformity } \Sigma_{i,j} \{g(i,j)\}^2 \quad (12)$$

$$\text{Homogeneity } \Sigma_{i,j} g(i,j)/\{1+(i-j)^2\} \quad (13)$$

$$\text{Inertia } \Sigma_{i,j} (i-j)^2 g(i,j) \quad (14)$$

$$\text{Cluster Shade } \Sigma_{i,j} (i+j-2\mu)^3 g(i,j) \quad (15)$$

$$\text{Cluster Prominence } \Sigma_{i,j} (i+j-2\mu)^4 g(i,j) \quad (16)$$

$$\text{Maximum Probability } \max\{g(i,j)\} \quad (17)$$

$$\text{Correlation } \Sigma_{i,j} (i-\mu)(j-\mu)/\sigma^2 g(i,j) \quad (18)$$

When g(i,j) was the normalized GLCM matrix and i and j were the indices of each normalized GLCM matrix element.

Data Analysis and the Classification Model

Based on the PCR results, all samples were categorized into five classes of healthy, HLB symptomatic, magnesium deficient, zinc deficient, and zinc deficient and HLB symptomatic samples. Then a principal component analysis (PCA) was performed on the data and all 96 samples were plotted using the first two principal components to visualize them in a two dimensional scatter plot. It was inferred from this scatter plot that the classification can be done in several 2-class identifications steps. FIG. 1 is a step by step classification model which was designed based on the principal component analysis. FIG. 1 illustrates the classification model which was designed based on the principal component analysis. At the first step, all samples were classified into two merged classes of healthy or magnesium deficient samples, and HLB symptomatic and zinc deficient samples. Then the samples at the left side of the model were classified into healthy and magnesium deficient classes. Samples at the right side of the model were also classified into two classes of HLB symptomatic and zinc deficient. Finally at the last step, HLB symptomatic samples were detected within the zinc deficient class.

The performances of seven classifiers including linear, naive Bayes linear, Mahalanobis, quadratic, naive Bayes quadratic, support vector machine (SVM), and K-nearest neighbors (KNN) were evaluated in this study. To prove that the obtained classification results do not depend on the validation and training sets, a K-fold cross validation approach, as per Huang and Chang (Huang, H. L., and F. L. Chang, 2007, "ESVM: Evolutionary support vector machine for automatic feature selection and classification of microarray data" in, *Biosystems,* 90(2): 516-528) (Huang and Chang 2007), with five folds was used in all classification steps. For this purpose, the dataset in each step was randomly separated in five folds; one for validation and four for training.

In order to find the best set of features for each step of the classification model, five different feature ranking methods containing t-test, entropy (or Kullback-Leibler distance), Bhattacharyya distance (or Chernoff bound), ROC (receiver operating characteristic), and Wilcoxon test (or Mann-Whitney) were conducted using Rankfeatures™ function in Matlab™ and evaluated. Then, all seven classifiers were trained using different number of top features which were ranked with each of the five ranking methods to determine the best set of features and classifier with the highest accuracy. Therefore, a total of 1050 different features-classifier sets (30 different number of top features×five ranking methods× seven classifiers) were compared to each other and the classifier which employed the minimum number of top features to yield the most accurate rate was selected for each step.

Classification

In this part, the whole classification model was run for each sample to classify it in each of five classes. For this purpose, all the data-set was divided randomly into two equal sets. Then the whole classification model was performed on the first half while the second half was used as the training set. The classification model was repeated for the second half, and this time the first half was used as the training set. Therefore, the results were available for all 96 samples. The best set of features and classifiers which were determined in the previous part were used in each step of the classification.

Results

PCR Test and Starch Measurement Results

Figure 2:
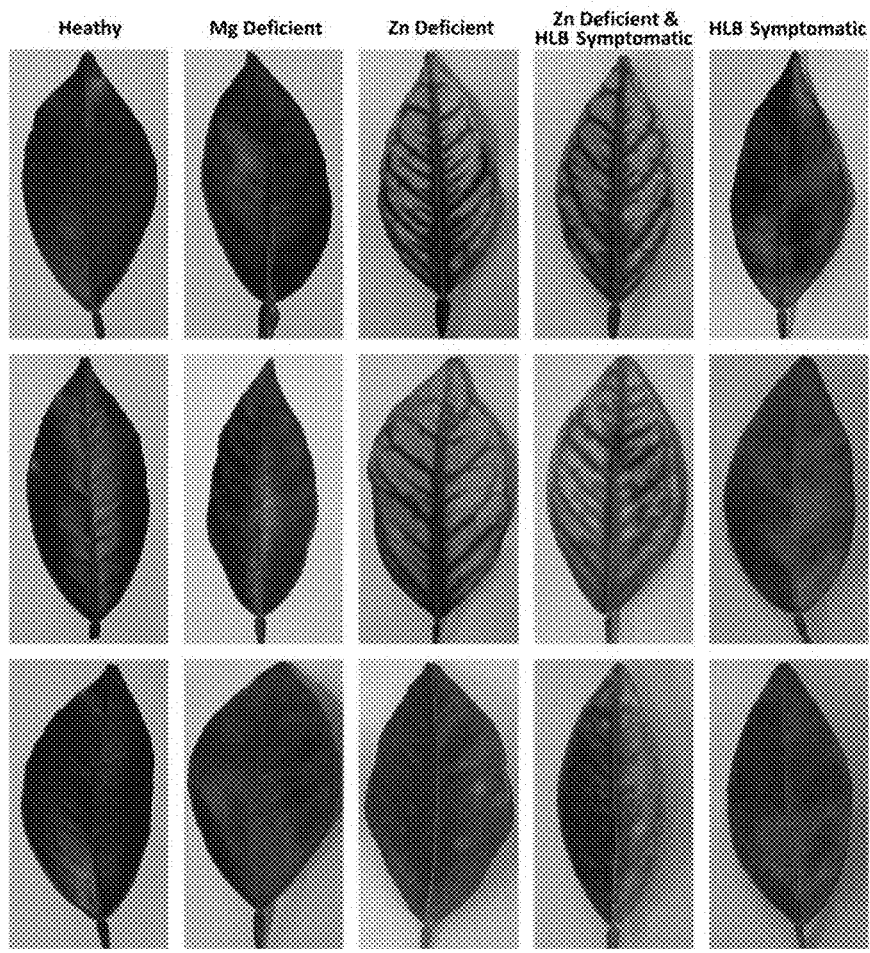
FIG. 2 are photographs of leaf samples for Example 1.

The PCR results were used to confirm the HLB infection of samples as a reference for creating the training and validation sets in the classification steps. Five different classes including healthy (20 samples), HLB symptomatic (20 samples), magnesium deficient (20 samples), zinc deficient (6 samples), and zinc deficient-HLB symptomatic (30 samples) leaves were defined based on the PCR results. FIG. 2 shows leaf sample images in five different classes. Three samples are shown for each class to illustrate the symptoms similarity and variability for each situation. HLB infection is almost impossible to be identified within the zinc deficient samples. The starch measurement was also conducted for all samples. The results showed that the starch concentration in all healthy samples was below the defined threshold with an average of 1.48 $\mu g/mm^2$. All samples except healthy class samples contained some yellow or light green areas and usually with similar patterns. For example, HLB symptomatic and magnesium deficient classes included an analogous light green symptom. However, the starch measurement results confirmed that the starch concentration in all magnesium deficient leaves was below 2 $\mu g/mm^2$ (with an average of 0.78 $\mu g/mm^2$), while the starch level in all HLB symptomatic samples exceeded the defined threshold (with an average of 37.46 $\mu g/mm^2$). It can be concluded that the light green symptom in the magnesium deficient class was not due to the starch concentration despite the fact that it looked similar to HLB symptom. The HLB infection within the zinc deficient samples was also extremely difficult to identify, since the zinc deficiency symptoms buried the HLB symptoms. Although the PCR results did not identify any HLB infection in six zinc deficient samples, the starch concentration exceeded the defined threshold in all six samples of this class with an average of 20.58 $\mu g/mm^2$. However, it was still less than the starch concentration average in HLB symptomatic leaves within the zinc deficient class which was 29.71 $\mu g/mm^2$.

Preprocessing

All images were calibrated so the averages of their background pixel values were similar after the calibration. Using the suggested gain adjustment approach, the AGC effect was partially cancelled because the images were calibrated to be analogous and they did not represent the original reflectance yet. However, since the textural features were used in this study, the relative variation in pixel values was good enough for the rest of the analysis, because they do not depend on the original reflectance.

Classification

The classification model was designed to identify the five classes in four different steps as described in the materials and methods. The best combination of classifier and features in each step was determined based on its performance compared to other combinations (Table 1-1). Mahalanobis classifier was able to identify the healthy and magnesium deficient leaves from the rest of samples with an accuracy of 100%. The top 13 features (ranked with Wilcoxon method) which were used in this classifier included six gray features (mean, STD, third moment, smoothness, entropy, and uniformity), six GLCM features (uniformity, inertia, mean, homogeneity, cluster shade, and maximum probability), and one LSP feature (third moment). Healthy and magnesium deficient samples were also classified with an accuracy of 100% using two gray features (ranked with T-Test method) including entropy and maximum probability. On the right side of the model, a linear classifier was able to identify HLB infected leaves from all zinc deficient samples with an accuracy of 94.4%. The top six features (ranked with Bhattacharyya method) included two gray features (uniformity and maximum probability), three GLCM features (cluster shade, cluster prominence, and variance) and one LSP feature (STD). Finally, the HLB infection within the zinc deficient samples was detected with an accuracy of 83.3% using linear classifier and top four features (ranked with entropy method) including one LSP feature (uniformity), two LBP features (mean and STD) and one GLCM feature (uniformity).

TABLE 1-1

The best combinations of features and classifier in each step of the classification model

| Step | Class 1 | Class 2 | Classifier | Number of top Features | Rank Method | Accuracy |
|---|---|---|---|---|---|---|
| 1 | Healthy Magnesium deficient | HLB symptomatic HLB symptomatic & Zinc deficient Zinc deficient | Mahalanobis | 13 | Wilcoxon | 100% |

TABLE 1-1-continued

The best combinations of features and classifier in each step of the classification model

| Step | Class 1 | Class 2 | Classifier | Number of top Features | Rank Method | Accuracy |
|---|---|---|---|---|---|---|
| 2 | Healthy | Magnesium deficient | SVM | 2 | T-Test | 100% |
| 3 | Zinc deficient HLB symptomatic & Zinc deficient | HLB symptomatic | Linear | 6 | Bhattacharyya | 94.4% |
| 4 | Zinc deficient | HLB symptomatic & Zinc deficient | Linear | 4 | Entropy | 83.3% |

The best combinations of classifier and features which were determined in the previous phase were employed to run the whole classification model on the dataset. Table 1-2 illustrates the classification results of the proposed model. The classification rates were shown in the diagonal of the table, and the rest of the grids demonstrated misclassification errors. Healthy and HLB symptomatic samples were identified correctly with the maximum accuracy of 100%. Magnesium deficiency was identified with an accuracy of 95% and only one sample of this class was misclassified in the HLB symptomatic class. Zinc deficiency was also identified with an accuracy of 88.9%, however, 66.7% of those zinc deficient samples which were not HLB infected based on the PCR result, were misclassified into either HLB symptomatic or zinc deficient and HLB symptomatic classes. The high misclassification error in the non-HLB symptomatic zinc deficient class was probably because of the high level of starch concentration (20.58 μg/mm$^2$ in average) in the samples, and since the proposed method was designed to highlight the starch in the leaf; their misclassification in the HLB symptomatic classes was expected. They can also be justified as HLB symptomatic samples which were not identified by PCR test because of the several inconsistencies caused by internal biotic conditions, as per Gottwald (Gottwald, T. R., 2010, "Current Epidemiological Understanding of Citrus Huanglongbing" in, *Annual Review of Phytopathology*, 48: 119-139, doi: 10.1146/annurev-phyto-073009-114418)(Gottwald 2010). The comparably high classification rate in magnesium deficient class also supported this idea, since the starch concentration levels in this class were considerably below the threshold (0.78 μg/mm$^2$ in average) and the PCR results confirmed that as well.

The main purpose of this study was to identify the HLB symptomatic samples, and so in another evaluation, the nutrient deficiency of samples was disregarded and the results in the Table 2 was merged into only two main classes of healthy and HLB symptomatic. Table 3 shows the classification accuracies and misclassification errors as well as the number of samples identified in each class, while only HLB detection was considered. The results showed that only five samples of each class were misclassified in the other class. The overall accuracy of 89.6% was achieved when only HLB detection was considered which included the accuracies of 90% for HLB class and 89.1% for healthy class. Four out of five false positive samples were actually zinc deficient leaves which were identified as the non-HLB symptomatic by PCR test but contained high level of starch accumulation. Since the starch measurement results contradicted the PCR results for these samples, their infection status could be considered questionable. All false negative samples were also zinc deficient leaves which their HLB infection was not identified using this method. Training the classifier using these zinc deficient samples with questionable HLB statuses might be another factor which decreased the overall accuracy.

TABLE 1-2

Number of samples classified into each of five classes and their corresponding classification accuracies or misclassification errors

| | | Actual class | | | | | |
|---|---|---|---|---|---|---|---|
| | | Healthy | Magnesium deficient | Zinc deficient | Zinc deficient & HLB symptomatic | HLB symptomatic | Sum |
| Prediction | Healthy | 20 (100%) | 0 | 0 | 0 | 0 | 20 |
| | Magnesium Deficient | 0 | 19 (95%) | 0 | 0 | 0 | 19 |
| | Zinc deficient | 0 | 0 | 2 (33.3%) | 5 (16.7%) | 0 | 7 |
| | Zinc deficient & HLB symptomatic | 0 | 0 | 3 (50%) | 22 (73.3%) | 0 | 25 |
| | HLB symptomatic | 0 | 1 (5%) | 1 (16.7%) | 3 (10%) | 20 (100%) | 25 |
| | Sum | 20 | 20 | 6 | 30 | 20 | 96 |

TABLE 1-3

Number of samples classified into each of healthy or HLB symptomatic classes and their corresponding classification accuracies and misclassification errors (%), the nutrient deficiency was disregarded in this table.

| | | Actual class | | |
|---|---|---|---|---|
| | | HLB | Healthy | Sum |
| Prediction | HLB | 45 (90%) | 5 (10.9%) | 50 |
| | Healthy | 5 (10%) | 41 (89.1%) | 46 |
| | sum | 50 | 46 | 96 |

Diagnostic approaches such as PCR test, starch measurement, and crop scouting are not absolutely accurate, and there is no 100% precise detection method that has been reported yet. Therefore, the assessment of the suggested method was definitely affected by this imprecision.

Combination of polarizing filters and narrow band imaging was confirmed to be able to highlight the HLB infection symptom (starch accumulation) in the citrus leaf. In the previous study, the same method was applied to the Hamlin variety of citrus and the overall accuracy of 91% was achieved for four-class identification. We added one more class of magnesium deficiency in this study and applied the method on the Valencia variety and obtained the overall accuracy of 86.5%. The zinc deficient classes in both studies decreased the overall accuracy because either the zinc deficiency symptoms buried the HLB symptoms or their HLB statuses were questionable. If the zinc deficiency classes were disregarded in this study, the overall accuracy would increase to 98.3% for three-class (healthy, HLB symptomatic, and magnesium deficient) identification.

Observations

The results of this study, i.e., this Example, suggest that the polarization planer rotation caused by the starch accumulated in the HLB infected citrus leaf can be effectively used for HLB detection. They also confirmed the results of the previous study which was conducted with a different variety of citrus. The wavelength of 591 nm was determined as a potential waveband in the visible range for the disease detection. Textural descriptors such as gray, GLCM, LBP, and LSP features were determined powerful tools to detect the polarization planer rotation caused by starch accumulation. However, gray and GLCM features contributed more effectively to the classification steps compared to the LBP and LSP descriptors. The magnesium deficiency which caused similar symptoms to HLB infection was identified with an excellent accuracy. It was determined that the HLB detection within the zinc deficient samples was not as accurate as the other classes, mostly because their HLB infection statuses were not confirmed precisely. However, it can be inferred from the overall accuracy that this method can be successfully employed in a fast and easy HLB detection application.

Example 2

The overall objective of this study, e.g., this Example, "study" and "Example" used interchangeably herein, was to develop a sensing system based on machine vision capable of discriminating between HLB-symptomatic and healthy leaves using polarized light. This concept is based on the prominent starch accumulation that takes place in HLB-symptomatic leaves compared to the lack of starch in otherwise healthy leaves or those under any other biotic or abiotic stress. Additionally, the known capability of starch to rotate the polarization planar of a polarized light, as per McMahon (McMahon, 2004), was evaluated for HLB-symptomatic citrus leaves. The specific objectives were: 1) to determine how starch accumulation in an HLB-symptomatic leaf affects the polarized light and how this can be used in HLB detection; 2) to develop an imaging system that can highlight the starch accumulation on leaves under field conditions; 3) to determine the best set of image features that differentiates HLB-symptomatic and healthy leaves; and, 4) to evaluate the accuracy of the proposed method compared with other techniques such as qrt-PCR analysis, starch measurement, spectroscopy, and airborne imaging.

Materials and Methods

Preliminary Experiment

In order to evaluate the effect of starch accumulation in HLB-symptomatic leaves on the polarization planar of the light, an initial experiment was conducted in May 2010 in the Citrus Research and Education Center (CREC) in Lake Alfred, Fla. In this experiment, citrus canopies were illuminated (after the sunset in darkness) with a halogen lamp (100 watt, JCD type, GY 6.35) and a polarized filter mounted in front of the lamp. Leaf reflectance was measured using a portable spectrometer (HR-1024, Spectra Vista Corporation, Poughkeepsie, N.Y.) with another polarized filter installed in front of the spectrometer in two separate positions: parallel to the lamp filter (to measure the maximum reflectance) and perpendicular to the lamp filter (to measure the minimum reflectance).

FIGS. 3A-3D show detection of HLB-symptomatic canopy using diffuse reflectance in a citrus grove—FIG. 3A is maximum reflectance, FIG. 3B is minimum reflectance, FIG. 3C shows a ratio between maximum and minimum reflectance, and FIG. 3D shows a ratio between healthy leaf reflectance ratio and HLB-symptomatic leaf reflectance ratio.

FIGS. 3A and 3B show maximum and minimum reflectance using parallel and perpendicular filters, respectively. The spectra were an average of 10 different sample measurements, and their standard deviations are shown as error bars at each wavelength. FIG. 3C is the minimum to maximum reflectance ratio of control (healthy) and greening (HLB-symptomatic). Also the ratio between the healthy and symptomatic leaf reflectance ratio is plotted in FIG. 3D. As shown in this figure, the highest ratio (1.6) was found near 600 nm, which suggested that this was the optimal wavelength to detect HLB-symptomatic leaves. Also, the ratio was close to 1.0 at 400 nm which meant the min/max ratio of healthy and HLB-symptomatic leaves were the same, so this wavelength can be used as a reference wavelength.

The Angle of Polarization—Planar Rotation Caused by Starch

In order to establish the degree which pure starch rotates the polarization planar of the light, pure starch powder (Cornstarch, Clabber Girl, Terre Haute, Ind.) was illuminated with polarized light, and its reflectance was measured using a spectrometer in 400-1000 nm (USB 2000+, Ocean Optics, Clear Water, Fla.). Based on the initial experimental results, the maximum rotation occurred at around 600 nm. Therefore, high luminous efficiency LEDs (LED Engin, San Jose, Calif.) at 591 nm (LZ1-00A100, 4 LEDs, 5 W per LED) were selected for illuminating the starch samples, since LEDs at exactly 600 nm were not available. A visible linear polarizing laminated film (Edmund Optics, Barrington, N.J.) was used for polarizing purpose. One filter was mounted in front of the light source and another was also placed in front of the spectrometer sensor in parallel direction. Then the angle between the spectrometer's filter and the light source's filter was varied from 0° (parallel) to 90° (perpendicular) by 10° increment and the reflectance was measured in each step. It was determined that the maximum reflectance of pure starch occurred when the light source and the spectrometer's polarizing filters were exactly perpendicular to each other.

Data Collection

Two datasets were collected for this study. In each dataset, there were two main super classes of HLB positive and HLB negative. The HLB positive super class included the HLB symptomatic samples as well as the nutrient deficient samples which were HLB infected too. The HLB symptomatic class contained the samples which their HLB infection were confirmed by qrt-PCR test but they did not show any nutrient deficiency symptoms. On the contrary, healthy samples and non HLB infected nutrient deficient samples were included in HLB positive super class. The first dataset contained 90 citrus leaf samples (Hamlin' sweet orange) in four classes including healthy (32 samples), HLB-symptomatic (28 samples), HLB negative zinc deficient (15 samples), and HLB positive zinc deficient (15 samples) samples were collected from a grove located at CREC in August, 2012. The second dataset which was collected from the same grove in December, 2012, contained 96 citrus leaf samples (Valencia) in five classes including healthy (20 samples), HLB-symptomatic (20 samples), HLB negative magnesium deficient (20 samples), HLB negative zinc deficient (6 samples), and HLB positive zinc deficient (30 samples) samples, from Example 1 above. Concentration of starch in each leaf was measured in μg starch/mm$^2$ according to the procedure described by Gonzalez, et al. (Gonzalez, et al. 2012). For this measurement, a tissue disk of 27.3 mm$^2$ from each leaf was excised with a paper puncher and homogenized in water. After a series of steps including boiling, alcohol precipitation and re-suspension of the starch in water, aliquots were combined with a 2% iodine solution. The absorbance was determined using a micro-plate reader (model 680, BioRad, Hercules, Calif.) at 595 nm. Starch concentration was calculated from an established standard curve. Finally, the threshold of 5 μg/mm$^2$ was used for HLB-infection detection (Gonzalez et al., 2012). For verification, a qrt-PCR analysis, as per Sankaran, et al. (Sankaran et al., 2010) was also conducted in a diagnostic laboratory located at the United States Sugar Corporation (USSC)/Southern Gardens (Clewiston, Fla.) for each individual leaf to determine their infection status.

Image Acquisition

Preliminarily evaluation showed that the accumulation of starch rotated part of the polarization planar of the light by 90 degrees in a detectable magnitude. Based on this fact, an image acquisition system was designed to measure leaf reflection of the polarized light in both parallel and perpendicular directions to the direction of polarized light of illumination. Also 591 nm and 400 nm were selected for narrow band illumination sources based on the preliminarily results as described earlier.

Figure 4:
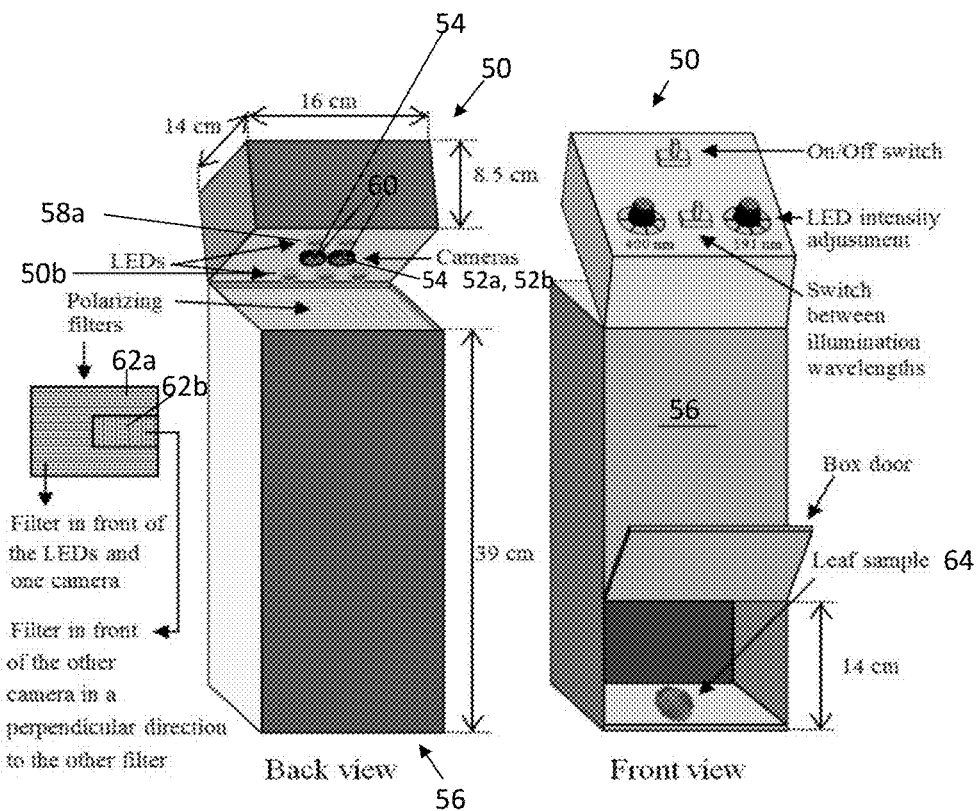
FIG. 4 is a diagram of an image acquisition system for the HLB-symptomatic canopy of Example 2.

FIG. 4 is a diagram showing an image acquisition system for detecting HLB-symptomatic leaves. The top part of the imaging box can be opened to adjust the cameras' lenses and polarizing filters. The illumination intensity and wavelength can be adjusted from the top panel. FIG. 4 shows a diagram of the image acquisition system 50 for detecting HLB-symptomatic leaves. Two commercial monochrome cameras 52a, 52b (EBC-B100G, EZ SPY CAM, Los Angeles, Calif.) with ICX404AL Sony CCD image sensors 54 that had the horizontal resolution of 420 TV lines were used. The cameras 52a, 52b were equipped with 25 mm narrow field of view lenses 60 and they were mounted at the top of the imaging box 56. A 4-Channel USB frame grabber (Model 2255, Sensory, Tigard, Oreg.) was used to convert analog output of the cameras to digital image with a resolution of 640×480 pixels.

A total of five high luminous efficiency LEDs 58a, 58b (LED Engine, San Jose, Calif.), one at 400 nm 58a (LZ1-00UA00, 1 LED, 5 W) and four 58b at 591 nm (LZ1-00A100, 4 LEDs, 5 W) were mounted at the top of the imaging box 56 for the narrow band illumination purpose. Narrow field of view LED lenses 60 were used to prevent any reflection inside the box 56. Two polarizing filters 62a, 62b (Visible linear polarizing laminated film, Edmund Optics, Barrington, N.J.) were also used: one 62a in front of the illumination system and one of the cameras 52a, and the other one 62b in front of the other camera 52b, but in a perpendicular direction to the first filter 62a. Therefore, at each wavelength, one camera 52a acquired an image with only the reflected light (from the leaf sample 64) which was in parallel polarization to the illumination polarization planar (maximum reflection), and the other camera 52b acquired an image with only reflected light in a perpendicular direction (minimum reflection). The imaging platform was enclosed by a wooden box (16×14×47 cm), so the LED light was the only source of illumination available for taking leaf sample 64 images. An electronic circuit was designed to control the light intensity and also switch between the two wavelengths. It also contained a 70 W LED driver (RCD-48-0.70-W, RECOM Electronic GmbH, Neu-Isenburg, Germany) which was designed for driving high power LED applications. Therefore, the image acquisition system was able to produce images from each sample in four different conditions which used parallel and perpendicular filters at 400 nm and 591 nm illumination conditions. The cameras 52a, 52b common field of view was determined by manual comparison of the images captured by the two cameras 52a, 52b.

Image Preprocessing

Commercial cameras are customarily equipped with automatic gain control (AGC), a feature which keeps similar image's intensity and contrast regardless of the illumination condition. In this study, the effect of AGC was removed using a calibration process because the real measurement of intensity was required. In order to solve this problem, calibration of images was conducted utilizing a same background in all images. At the first step of calibration, the average of backgrounds gray levels in the images captured with a same illumination-polarization (or imaging) condition was measured and the ratio between this average to each image background gray level was used as a unique gain multiplier for the corresponding image. Then the exact reflectance of background in all four illumination-polarization conditions was measured using the spectrometer and the ratios between these values were used to adjust the intensity in a second step.

Pixel-Based Analysis

All the data analyses were conducted using MATLAB™ (version R2011a, MathWorks™, Natick, Mass., USA). Every pixel belonging to the leaf area in the images of all 90 samples (the 'Hamlin' dataset) was used in this analysis. There were four monochrome images for each sample that were acquired in four different illumination-polarization conditions: 1) 400 nm (Max) image: an image acquired with the 400 nm LED, and parallel polarizing filters mounted in front of the camera and the LED; 2) 400 nm (Min) image: an image acquired with the 400 nm LED, while the polarizing filter mounted in front of the camera was in a perpendicular direction to the polarizing filter mounted in front of the LED; 3) 591 nm (Max) image: an image acquired with the 591 nm LEDs, and parallel polarizing filters mounted in front of the camera and the LEDs; and, 4) 591 nm (Min) image: an image acquired with the 591 nm LEDs, while the polarizing filter mounted in front of the camera was in a perpendicular direction to the polarizing filter mounted in front of the LEDs.

"Max" represents the maximum reflectance which was acquired using polarizing filters in parallel directions for the camera and the LEDs. "Min" represents the minimum reflectance which was acquired with polarizing filters in perpendicular directions for the camera and the LEDs. All four images were acquired from the same scene; therefore there were four different values for each pixel representing the reflectance in four imaging conditions. In order to determine which imaging condition had the ability to differentiate the pixels belonging to the healthy and HLB-symptomatic areas, a K-means clustering method was conducted for each imaging condition separately. Therefore, K-means was applied to a one dimensional feature vector every iteration, and as a result, it tried to determine the best gray level threshold for image segmentation. Two clusters (healthy and HLB-symptomatic) were defined for the K-means algorithm and the accuracy of correct clustering was evaluated and used to judge about each imaging condition ability in HLB detection. The clustering was performed in two runs; first, it was applied for the pixels belonging to all the images at the same time (general clustering); at the second run, it was applied on each image pixels separately (individual clustering).

Textural Feature Extraction

Textural features of 591 nm (Min) images were used because the pixel based analysis showed that only this imaging condition provided useful information for the detection purpose (as explained in the results, pixel based analysis section). The features were extracted from the leaf area in four different groups including gray, local binary pattern (LBP), local similarity pattern (LSP) and gray level cooccurrence matrix (GLCM) features.

LBP is a very creative approach in image textural description in which each pixel in a 3×3 window is threshold by the central gray level and replaced by 0 if its value is smaller than the central pixel value and by 1 if its value is larger than the central pixel value. Then the threshold values are considered as an 8-bit binary value and its equivalent decimal value replaces the central pixel value, as per Ojala, et al. (Ojala, et al. 1996). LSP uses almost the same principle of comparing the neighborhood pixels with the central pixel which is employed in LBP procedure, but in a different approach. In LSP, a 2-bit code describes the relation between each neighbor pixel and central pixel. A similarity range is defined in LSP, and if the neighbor pixel value is below, within or above the similarity range, it is replaced by 00, 01, or 10, respectively. Each neighbor pixel code is multiplied by the corresponding weight and the LSP code is created. The same approach in LBP was also used in LSP to make it a rotational invariant. Both LBP and LSP codes are rotated to obtain their minimum possible values and this procedure makes them rotational invariant, as reported by Pourreza, et al. (Pourreza et al. 2011). GLCM for an 8-bit gray scale image is a 256×256 matrix which shows how often two different gray values are neighbors in four main directions (0°, 45°, 90°, and 135°). The normalized GLCM as it was described by Majumdar and Jayas (Majumdar, S., and D. S. Jayas, 1999, "Classification of Bulk Samples of Cereal Grains Using Machine Vision" in, *Journal of Agricultural Engineering Research*, 73(1): 35-47) (Majumdar and Jayas 1999), was used in this research, i.e., this Example.

Table 2-1 shows features extracted from normalized histogram (p(i) when i was the gray level ranged from 0 to 255) of the gray image in 591 nm (Min). These features are common statistical image descriptors which have been used frequently by other researchers. The first six features of Table 2-1 (mean, standard deviation, third moment, smoothness, uniformity, and entropy) were also extracted from the normalized histogram of LBP and LSP matrices, as per Pourreza, et al. (Pourreza and Pourreza, et al. 2012).

TABLE 2-1

Features extracted from the normalized histogram of gray, LBP, and LSP matrices.

| Feature | Equation |
| --- | --- |
| Mean | $\mu = \Sigma_i i p(i)$ |
| Standard Deviation (SD) | $\sigma = \sqrt{\Sigma_i (i - \mu)^2 p(i)}$ |
| Third Moment | $\Sigma_i (i - \mu)^3 p(i)$ |
| Smoothness | $1 - 1/(1 + \sigma^2)$ |
| Uniformity | $\Sigma_i p(i)^2$ |
| Entropy | $-\Sigma_i p(i) \log \{p(i)\}$ |
| Maximum Gray Level Probability Range | $(i|p(i) = \max)$ $\{\max (i|p(i) \neq 0) - \min (i|p(i) \neq 0)\}$ |

Table 2-2 shows equations used for extracting 10 features from normalized GLCM (g(i,j), when i and j were the indices of GLCM matrix elements) of 591 nm (Min) images.

TABLE 2-2

Features extracted from the normalized GLCM matrices

| Feature | Equation |
| --- | --- |
| Mean | $\mu = \Sigma_{i,j} i g(i, j)$ |
| Variance | $\sigma^2 = \Sigma_{i,j} (i - \mu)^2 g(i, j)$ |
| Entropy | $-\Sigma_{i,j} g(i, j) \log \{g(i, j)\}$ |
| Uniformity | $\Sigma_{i,j} \{g(i, j)\}^2$ |
| Homogeneity | $\Sigma_{i,j} g(i, j) / \{1 + (i - j)^2\}$ |
| Inertia | $\Sigma_{i,j} (i - j)^2 g(i, j)$ |
| Cluster Shade | $\Sigma_{i,j} (i + j - 2\mu)^3 g(i, j)$ |
| Cluster Prominence | $\Sigma_{i,j} (i + j - 2\mu)^4 g(i, j)$ |
| Maximum Probability | $\max\{g(i, j)\}$ |
| Correlation | $\Sigma_{i,j} (i - \mu)(j - \mu)/\sigma^2 g(i, j)$ |

Classification Models

Two principal component analysis (PCA) was performed on the feature vectors of both datasets, and all samples in each dataset were illustrated in a separate two dimensional plot in which the x and y axes were the first and second PCs. These plots depicted the distributions of samples which were used to design the step by step classification models.

Figure 5:
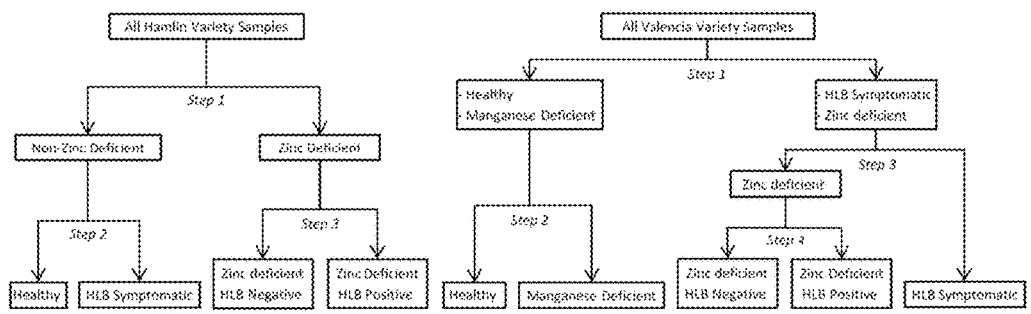
FIG. 5 is a diagram of a classification model for Example 2.

FIG. 5 shows step by step classification models for 'Hamlin' dataset (left) and 'Valencia' dataset (right). FIG. 5 shows the classification model for the 'Hamlin' dataset which was designed in three successive steps. In the first step, zinc deficient samples were detected, followed by two HLB detections carried out as the second and third steps in each of non-zinc deficient class or zinc deficient class separately. Since there was an additional class of magnesium deficient samples in the 'Valencia' dataset, the classification model was designed in four successive steps for this dataset (FIG. 5). In the first step, the healthy and magnesium deficient samples were detected from the rest of dataset, and these two classes were divided in the second step. In the third step, HLB-symptomatic samples were identified from zinc deficient samples, followed by another HLB detection conducted within the zinc deficiency class as the forth step.

Gray, GLCM, LBP, and LSP features were investigated and ranked both separately and together. The 'rankfeatures' function of MATLAB was used to rank the features which contribute more in each step of the classification. In this method, a nonlinear matrix equation under an orthonormal coordinate system was solved and the optimal transformation matrix solution was determined from the nonlinear matrix equation using a recursive algorithm, as per Xuan, et al. (Xuan, G., P. Chai, and M. Wu, 1996, "Bhattacharyya distance feature selection" in, *Proceedings of the 13th International Conference on Pattern Recognition*, 195-199. Vienna, Austria: IEEE) (Xuan et al., 1996). The performance of seven supervised learning methods including support vector machine (SVM), linear, naive Bayes linear, quadratic, naive Bayes quadratic, Mahalanobis, and KNN were evaluated using MATLAB functions. SVM tries to minimize the misclassification error by constructing a hyperplane which maximizes the margin between the two classes' nearest training data points. Linear method tries to project all the data point to a one dimensional space and classify them based on the training set. A quadratic classifier is similar to linear classifier with the assumption of normally distributed features in each class; however, each class's covariance is not necessarily identical. Naive Bayes classifiers add an assumption (to the linear and quadratic classifiers) in which the existence of a specific descriptor in a class is not related to the existence of any other descriptor. A Mahalanobis classifier works based on the general squared interpoint distance (or Mahalanobis distance) between data points of the classes. The KNN method also classifies samples based on the closest training examples' label, as per Bishop (Bishop, C. M., 2006, "Pattern Recognition And Machine Learning," 1st ed., New York: Springer Science) (Bishop 2006). A K-fold (5-fold) cross validation method, as per Huang and Chang (Huang and Chang 2007), was employed in all classification steps to confirm that the achieved results were independent to the training and validation sets. The dataset was randomly divided into five folds (four folds for training and one fold for validation) in each classification and the whole process was repeated 10 times. Then the range and average accuracy were determined and considered for the system evaluation. In order to find the optimized number of features in each step, each classifier was employed several times using different number of top features (starting with one feature) until the accuracy reached its highest level. The classifier that achieved the highest accuracy with minimum number of features was considered as the best classifier in the corresponding step.

After determining the best combination of features and classifier for all the steps, each dataset was divided randomly into two equal sets. Then the whole model was conducted while one set was used as the training set and the other set was used as the validation set. Afterwards, the classification model was repeated while the two sets exchanged their role. Therefore, the classification results for all samples were obtained.

Results i. Image Preprocessing

Figure 6:
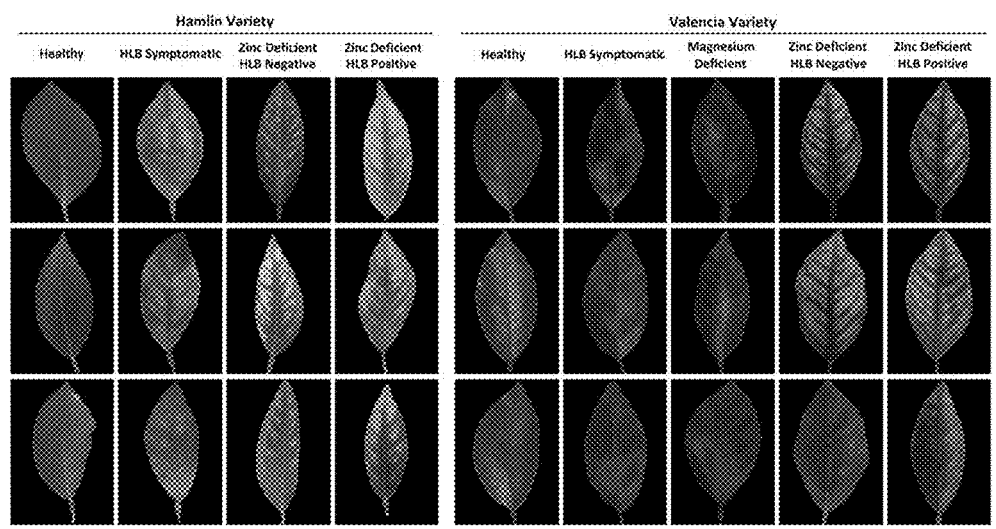
FIG. 6 are images of leaves in four classes for the "Hamlin" dataset (left) and for the "Valencia" dataset (right) of Example 2.

FIG. 6 shows images of leaves in four different classes for 'Hamlin' dataset (left) and in five classes for 'Valencia' dataset (right) used for HLB analyses. Three samples are presented for each category to demonstrate the variability for each condition and the frequent overlapping of characteristics. Magnesium deficient leaves were the most difficult to differentiate from HLB-symptomatic. HLB infection within the zinc deficient class was also impossible to be identified by human eyes.

FIG. 6 shows some examples of leaves representing each class in both datasets. Healthy samples were mostly evenly green in color, while HLB-symptomatic, magnesium deficient and zinc deficient leaves had some similar yellow molting patters. The molting symptoms on HLB-symptomatic samples were in a range of very clear symptoms (for advanced level of infection) to unclear symptoms (for early stage of infection). Additionally, HLB symptoms were typically in an asymmetric pattern while zinc and magnesium deficient leaves usually had a symmetric pattern of molting; nevertheless, they were not easily distinguishable. HLB infection in a zinc deficient leaf was even more difficult to detect since the zinc symptoms masked HLB symptoms.

Figure 7:
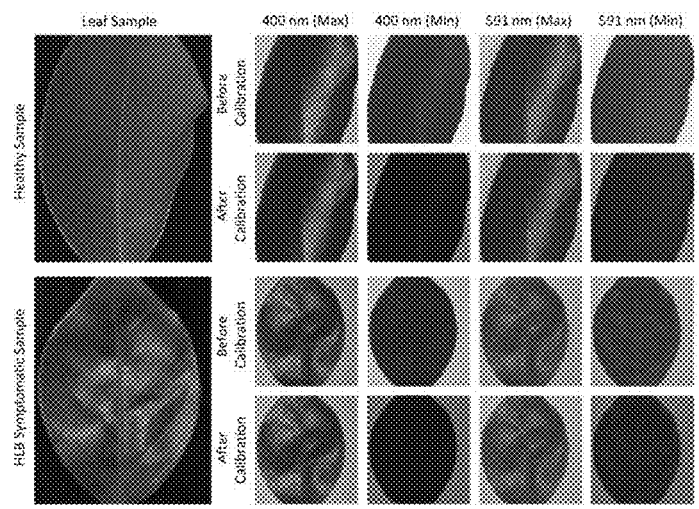
FIG. 7 are images of leaves of calibration results for "Hamlin" leaves, healthy (top) and HLB-symptomatic (bottom), of Example 2.

FIG. 7 shows examples of the calibration result on two samples images (from 'Hamlin'): healthy sample (top) and HLB-symptomatic sample (bottom). FIG. 7 illustrates example images of two leaves (one healthy and one HLB-symptomatic) before and after the calibration. The average intensity usually decreased after the calibration of the images which were acquired using perpendicular filters [400 nm (Min) and 591 nm (Min)]. The effect of AGC was mostly cancelled using the proposed gain adjustment method. Although the original reflectance was not completely recovered using this method, the correct reflectance ratios between two polarization conditions in each wavelength were retrieved, which was acceptable for this study.

ii. Starch Measurement and qrt-PCR Analysis

In a qrt-PCR analysis, a positive reaction is identified by the accumulation of a fluorescent signal. The cycle threshold (CT value) is the number of necessary cycles for the fluorescent signal to cross the threshold. The CT threshold of 33 was selected to indicate HLB infection as customarily for the state labs, as per Li, et al. (Li, W., J. S. Hartung, and L. Levy, 2006, "Quantitative real-time PCR for detection and identification of *Candidatus Liberibacter* species associated with citrus huanglongbing" in, *Journal of Microbiological Methods*, 66(1): 104-115) (Li, et al, 2006). CT values below the threshold indicated HLB infection of the samples. Tables 2-3 and 2-4 show the results of the qrt-PCR analysis by the CT values for each sample as well as the corresponding starch concentrations for 'Hamlin' and 'Valencia' datasets correspondingly. The CT values in the healthy, magnesium deficient, and zinc deficient HLB negative classes were above the threshold, and so, they were considered as HLB negative samples. Contrarily, the CT values in the HLB-symptomatic and zinc deficient HLB positive classes were below the established threshold value. Based on these results, the 'Hamlin' dataset included 32 healthy, 28 HLB-symptomatic, 15 zinc deficient HLB negative, and 15 zinc deficient HLB positive samples. The 'Valencia' dataset also contained 20 healthy, 20 HLB-symptomatic, 20 magnesium deficient, 6 zinc deficient HLB negative, and 30 zinc deficient HLB positive samples.

TABLE 2-3

Results of the qrt-PCR analysis and starch measurement for 'Hamlin' dataset

| Sample No. | qrt-PCR (CT) | Starch ($\mu g/mm^2$) |
|---|---|---|
| Healthy | | |
| 1 | 40 | 1.46 |
| 2 | 40 | 2.13 |
| 3 | 40 | 1.91 |

TABLE 2-3-continued

Results of the qrt-PCR analysis and starch measurement for 'Hamlin' dataset

| Sample No. | qrt-PCR (CT) | Starch (µg/mm²) |
|---|---|---|
| 4 | 40 | 1.07 |
| 5 | 40 | 2.10 |
| 6 | 40 | 3.16 |
| 7 | 40 | 1.77 |
| 8 | 40 | 2.58 |
| 9 | 40 | 3.47 |
| 10 | 40 | 1.31 |
| 11 | 40 | 2.03 |
| 12 | 40 | 1.48 |
| 13 | 40 | 0.86 |
| 14 | 40 | 1.79 |
| 15 | 40 | 2.51 |
| 16 | 40 | 0.79 |
| 17 | 40 | 2.01 |
| 18 | 40 | 1.07 |
| 19 | 40 | 1.67 |
| 20 | 40 | 1.24 |
| 21 | 40 | 0.93 |
| 22 | 40 | 0.91 |
| 23 | 40 | 2.29 |
| 24 | 40 | 1.05 |
| 25 | 40 | 1.17 |
| 26 | 40 | 1.77 |
| 27 | 39.84 | 2.37 |
| 28 | 37.30 | 0.55 |
| 29 | 36.51 | 2.25 |
| 30 | 36.00 | 1.53 |
| 31 | 34.91 | 2.44 |
| 32 | 33.53 | 21.72 |
| HLB-Symptomatic | | |
| 33 | 31.98 | 20.02 |
| 34 | 30.99 | 25.19 |
| 35 | 27.36 | 10.79 |
| 36 | 26.09 | 12.49 |
| 37 | 22.93 | 29.26 |
| 38 | 22.92 | 8.35 |
| 39 | 22.81 | 46.62 |
| 40 | 22.54 | 61.24 |
| 41 | 22.49 | 82.32 |
| 42 | 22.46 | 5.12 |
| 43 | 22.43 | 11.94 |
| 44 | 22.34 | 61.77 |
| 45 | 22.17 | 82.32 |
| 46 | 22.08 | 71.24 |
| 47 | 22.07 | 51.43 |
| 48 | 22.05 | 60.04 |
| 49 | 21.86 | 39.28 |
| 50 | 21.45 | 54.90 |
| 51 | 21.45 | 43.66 |
| 52 | 21.37 | 72.75 |
| 53 | 21.35 | 61.86 |
| 54 | 21.31 | 11.38 |
| 55 | 21.27 | 70.86 |
| 56 | 21.11 | 82.32 |
| 57 | 21.11 | 38.54 |
| 58 | 20.86 | 69.28 |
| 59 | 20.76 | 82.32 |
| 60 | 20.7 | 65.02 |
| Zinc deficient - HLB negative | | |
| 61 | 40 | 7.65 |
| 62 | 40 | 7.44 |
| 63 | 40 | 8.04 |
| 64 | 40 | 12.41 |
| 65 | 40 | 5.60 |
| 66 | 40 | 9.11 |
| 67 | 39.78 | 7.27 |
| 68 | 39.46 | 2.63 |
| 69 | 39.32 | 14.81 |
| 70 | 38.83 | 18.13 |
| 71 | 37.93 | 11.55 |
| 72 | 37.18 | 4.04 |
| 73 | 36.86 | 10.67 |
| 74 | 36.78 | 28.06 |
| 75 | 36.24 | 2.63 |
| Zinc deficient - HLB positive | | |
| 76 | 24.6 | 18.47 |
| 77 | 24.11 | 57.01 |
| 78 | 23.97 | 58.99 |
| 79 | 23.81 | 17.51 |
| 80 | 23.7 | 17.37 |
| 81 | 23.51 | 2.58 |
| 82 | 23.38 | 21.72 |
| 83 | 23.19 | 8.99 |
| 84 | 22.62 | 9.42 |
| 85 | 22.53 | 43.15 |
| 86 | 22.23 | 41.48 |
| 87 | 21.76 | 45.98 |
| 88 | 21.61 | 74.11 |
| 89 | 21.47 | 82.32 |
| 90 | 21.21 | 9.95 |

TABLE 2-4

Results of the qrt-PCR analysis and starch measurement for 'Valencia' dataset

| Sample No. | qrt-PCR (CT) | Starch (µg/mm²) |
|---|---|---|
| Healthy | | |
| 1 | 40 | 1.56 |
| 2 | 40 | 1.61 |
| 3 | 40 | 0.77 |
| 4 | 40 | 0.74 |
| 5 | 40 | 1.11 |
| 6 | 40 | 1.96 |
| 7 | 38 | 1.73 |
| 8 | 40 | 1.66 |
| 9 | 40 | 3.37 |
| 10 | 40 | 0.39 |
| 11 | 38.85 | 1.93 |
| 12 | 40 | 1.41 |
| 13 | 40 | 1.46 |
| 14 | 40 | 0.87 |
| 15 | 40 | 1.31 |
| 16 | 40 | 1.04 |
| 17 | 40 | 0.94 |
| 18 | 40 | 1.29 |
| 19 | 40 | 2.58 |
| 20 | 40 | 1.78 |
| HLB-Symptomatic | | |
| 21 | 23.38 | 24.35 |
| 22 | 23.14 | 44.12 |
| 23 | 21.12 | 22.71 |
| 24 | 22.35 | 43.05 |
| 25 | 22.64 | 44.74 |
| 26 | 21.61 | 20.85 |
| 27 | 23.33 | 68.99 |
| 28 | 22.39 | 44.02 |
| 29 | 22.06 | 42.98 |
| 30 | 23.39 | 38.83 |
| 31 | 21.07 | 32.09 |
| 32 | 23.26 | 42.65 |
| 33 | 24.34 | 5.68 |
| 34 | 24.9 | 24.20 |
| 35 | 23.39 | 34.47 |
| 36 | 22.98 | 51.38 |
| 37 | 22.22 | 54.11 |
| 38 | 22.81 | 41.96 |
| 39 | 23.9 | 26.78 |

TABLE 2-4-continued

Results of the qrt-PCR analysis and starch measurement for 'Valencia' dataset

| Sample No. | qrt-PCR (CT) | Starch (μg/mm²) |
|---|---|---|
| 40 | 22.2 | 41.29 |
| Magnesium deficient | | |
| 41 | 40 | 0.42 |
| 42 | 40 | 0.57 |
| 43 | 40 | 0.52 |
| 44 | 40 | 0.52 |
| 45 | 40 | 0.69 |
| 46 | 40 | 1.31 |
| 47 | 40 | 1.14 |
| 48 | 40 | 1.04 |
| 49 | 40 | 1.44 |
| 50 | 37.48 | 0.54 |
| 51 | 40 | 0.69 |
| 52 | 39.31 | 0.84 |
| 53 | 40 | 0.62 |
| 54 | 40 | 0.92 |
| 55 | 40 | 0.72 |
| 56 | 40 | 0.52 |
| 57 | 40 | 0.27 |
| 58 | 40 | 1.58 |
| 59 | 40 | 0.92 |
| 60 | 40 | 0.30 |
| Zinc deficient - HLB negative | | |
| 61 | 36.71 | 11.36 |
| 62 | 37.37 | 20.90 |
| 63 | 40 | 27.00 |
| 64 | 40 | 11.13 |
| 65 | 37.89 | 40.30 |
| 66 | 36 | 12.79 |
| Zinc deficient - HLB positive | | |
| 67 | 22.9 | 47.12 |
| 68 | 21.33 | 55.87 |
| 69 | 21.41 | 10.69 |
| 70 | 23.16 | 22.81 |
| 71 | 23.35 | 39.50 |
| 72 | 21.17 | 29.83 |
| 73 | 22.54 | 14.51 |
| 74 | 22.29 | 36.92 |
| 75 | 21.64 | 49.03 |
| 76 | 27.57 | 27.38 |
| 77 | 23.42 | 23.66 |
| 78 | 22.56 | 4.36 |
| 79 | 23.78 | 0.69 |
| 80 | 23.38 | 13.02 |
| 81 | 21.69 | 29.78 |
| 82 | 21.35 | 51.53 |
| 83 | 22.18 | 8.60 |
| 84 | 25.6 | 18.25 |
| 85 | 26.93 | 2.08 |
| 86 | 22.51 | 40.07 |
| 87 | 22.41 | 47.81 |
| 88 | 23.03 | 67.78 |
| 89 | 21.25 | 19.66 |
| 90 | 23.31 | 30.35 |
| 91 | 25.67 | 22.74 |
| 92 | 25.34 | 50.81 |
| 93 | 23.05 | 35.02 |
| 94 | 20.56 | 45.08 |
| 95 | 29.24 | 3.94 |
| 96 | 24.74 | 42.48 | iii. Pixel-Based Analysis

Figure 8:
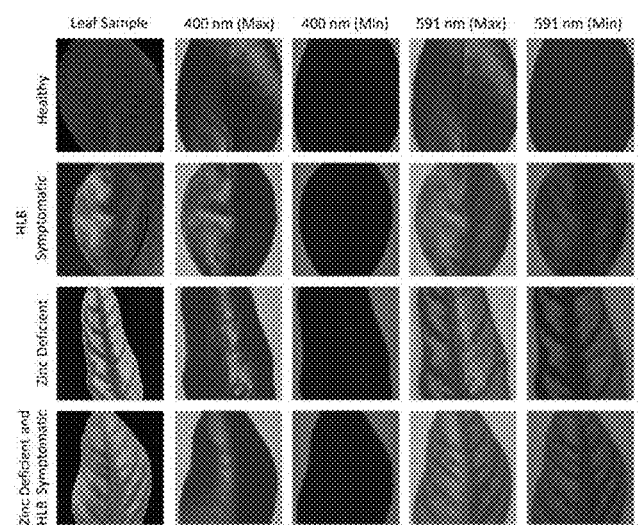
FIG. 8 shows images acquired with the image acquisition system of Example 2.

FIG. 8 shows images acquired using the image acquisition system with four imaging conditions (Hamlin' dataset). FIG. 8 illustrates some examples of the images acquired using the image acquisition system including healthy, HLB-symptomatic, zinc deficient HLB negative and zinc deficient HLB positive leaves from the 'Hamlin' dataset. The first column shows the samples color images and the following four columns show the same sample images in four different imaging conditions.

Figure 9:
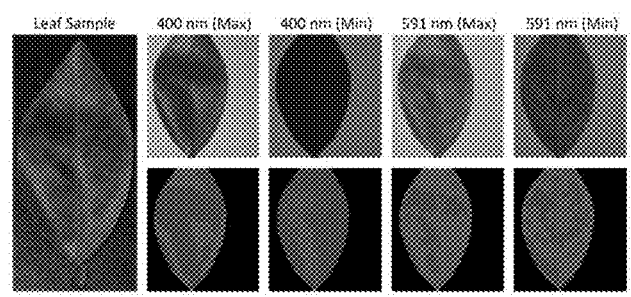
FIG. 9 shows image segmentation based on general clustering for the "Hamlin" leaves of Example 2.

An example of image segmentation based on a general clustering (a single threshold for all the images) in which the K-means algorithm was applied once to all the samples at the same time is shown in FIG. 9. (An example of image segmentation based on a general clustering using K-means for an HLB-symptomatic sample; green and pink colors indicate the healthy and symptomatic clusters, respectively ('Hamlin' dataset)).

It was established that the 400 nm (Max) images did not contain any useful information about the symptomatic areas, and the clustering procedure just distinguished the glossy (high intensity) parts of the leaf from non-glossy (low intensity) parts. The pixel values belonging to healthy and HLB-symptomatic (or zinc deficient) areas were also not significantly different in 400 nm (Min) images as expected based on the preliminarily results. In the 591 nm (Max) images, the pixel values belonging to healthy, HLB-symptomatic and zinc deficient areas were different; however, there were also some glossy parts on the leaves (specially on healthy leaves) in which their pixel values were extremely similar to non-healthy parts such as HLB-symptomatic and/or zinc deficient parts. The 591 nm (Min) images, however, contained very useful information and non-healthy parts were distinctive as shown in FIG. 9.

Figure 10:
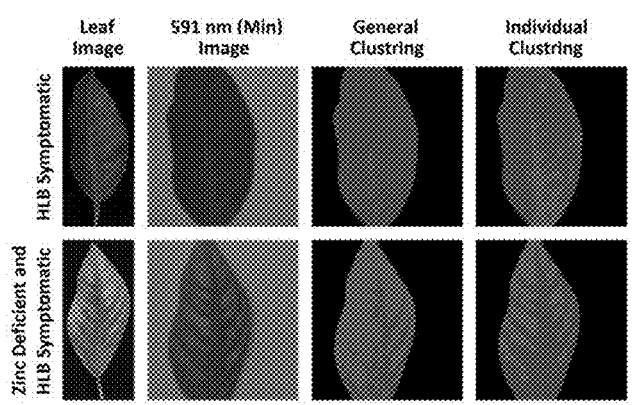
FIG. 10 shows images comparing the results of segmentation methods in Example 2.

Due to the incomplete AGC effect cancelation, the overall average intensity of the image for some samples was different than the others in 591 nm (Min) images. This led to a misclassification of some healthy pixels in non-healthy classes including HLB-symptomatic or zinc deficient classes; still the healthy and non-healthy areas were distinguishable while the clustering was performed for individual samples separately, as shown in FIG. 10 (comparison of the results of two segmentation methods based on general and individual clustering for an HLB-symptomatic sample (above) and a zinc deficient HLB positive leaf samples (below)). Green and pink colors indicate the healthy and symptomatic clusters correspondingly ('Hamlin' dataset)), and FIG. 10 shows two examples of segmentation based on general and individual clustering. The top sample in FIG. 10 is an HLB-symptomatic sample in which the image intensity was below the average, so the general clustering segmented most of its pixels into a healthy cluster (green color), while the individual clustering (individual threshold for each image) was able to detect the symptomatic areas more accurately. The opposite situation happened for the sample on the bottom in FIG. 10, in which the image intensity was higher than the average and the general clustering misclassified many healthy pixels into a symptomatic cluster. The individual clustering was able to more accurately distinguish healthy and symptomatic areas in this case as well. From these data, it was concluded that employing the pixel values alone did not result in a general criteria with high recognition accuracy; however, some features such as textural features which describe each sample individually could play a more effective role in the classification process.

iv. Step by Step Classification

Table 2-5 illustrates the best set of features and classifier which resulted in the maximum average accuracy in each step of the classification models. The Mahalanobis classifier presented the best performance in the all three classification steps for the 'Hamlin' dataset and also in the first classification step for the 'Valencia' dataset.

TABLE 2-5

The best set of features and classifier for each step of the classification models

| Step | | TPR* (%) | FPR** (%) | Best Classifier | # of Top Features |
|---|---|---|---|---|---|
| | 'Hamlin' Dataset | | | | |
| 1 | Identification of zinc deficient samples from the rest of dataset | 96.7 | 1.7 | Mahalanobis | 15 |
| 2 | Identification of HLB positive samples within non-zinc deficient class | 92.9 | 0.0 | Mahalanobis | 14 |
| 3 | Identification of HLB positive samples within zinc deficient class | 80.0 | 0.0 | Mahalanobis | 3 |
| | 'Valencia' Dataset | | | | |
| 1 | Identification of healthy and magnesium deficient samples from the rest of dataset | 100.0 | 0.0 | Mahalanobis | 13 |
| 2 | Identification of healthy samples from magnesium deficient samples | 100.0 | 0.0 | SVM | 2 |
| 3 | Identification of HLB symptomatic samples from zinc deficient samples | 88.9 | 0.0 | Linear | 6 |
| 4 | Identification of zinc deficient HLB positive samples from zinc deficient HLB negative samples | 83.3 | 16.7 | Linear | 4 |

*True Positive Rate (TPR)
**False Positive Rate (FPR)

Table 2-6 also shows the best sets of features which were employed in the classification steps. Zinc deficiency in 'Hamlin' dataset was detected with an average accuracy of 97.5% using top 15 features of all feature groups. The healthy samples were identified with 100% accuracy using 14 top features, while the highest HLB identification rate was 92.9%. The zinc deficient HLB negative samples were also identified with 100% accuracy using only the top three features which were from LBP feature group, while the highest HLB detection within the zinc deficiency class was 80%. Healthy and magnesium deficient samples were identified with an accuracy of 100.0% at the first and second steps of the classification model using Mahalanobis (with top 13 features) and SVM (with top two features) classifiers respectively. The HLB symptomatic samples were also recognized from zinc deficient samples using linear classifier and top six features with an average accuracy of 94.5% at the third step of the classification model. The best average classification rate (83.3%) for HLB identification within the zinc deficient class was obtained using linear classifier and top four features.

TABLE 2-6

Sets of features which were used in the step by step classification models. The features in each step were ordered based on their rankings which indicate the contribution level of each feature in an accurate classification process

| Step | Features |
|---|---|
| | 'Hamlin' Dataset |
| 1 | LBP Entropy, Gray Smoothness, LSP Uniformity, LBP Standard Deviation, GLCM Cluster Shade, GLCM Maximum Probability, LSP 3rd Moment, LBP Mean, LSP Smoothness, Gray Mean, Gray Entropy, GLCM Correlation, Gray Standard Deviation, LSP Mean, and LSP Standard Deviation. |
| 2 | LSP Mean, Gray Entropy, LBP Uniformity, LSP Standard Deviation, Gray Smoothness, Gray 3rd Moment, LSP 3rd Moment, LSP Entropy, LSP Uniformity, LBP Mean, Gray Uniformity, Gray Standard Deviation, GLCM Homogeneity, and LSP Smoothness. |
| 3 | LBP Smoothness, LBP Uniformity, and LBP 3rd Moment. |
| | 'Valencia' Dataset |
| 1 | Gray Mean, Gray Standard Deviation, GLCM Uniformity, Gray 3d Moment, GLCM Inertia, Gray Smoothness, GLCM Mean, GLCM Homogeneity, LSP 3d Moment, Gray Entropy, Gray Uniformity, GLCM Cluster Shade, GLCM Maximum probability. |
| 2 | Gray Entropy, Gray Maximum Probability. |
| 3 | Gray Uniformity, Gray Maximum Probability, GLCM Cluster Shade, GLCM Cluster Prominence, LSP Standard Deviation, GLCM Variance. |
| 4 | LSP Uniformity, LBP Mean, GLCM Uniformity, LBP Standard Deviation. |

Using the best set of features and classifier for each step, the complete classification models were performed for all samples in each dataset. Table 2-7 and 2-8 illustrate the step by step classification results for 'Hamlin' and 'Valencia' datasets correspondingly. The number of samples classified into the correct classes and also their classification accuracies in the parentheses (percent) are shown in the principal diagonal of the table and the number of incorrect detections in each class and their misclassification rate in the parentheses are shown in other grids. Healthy samples were classified with 100% of accuracy in both datasets. The classification rates for HLB-Symptomatic samples were 100% for 'Valencia' dataset and 85.7% for 'Hamlin' dataset. Still two out of 4 misclassified HLB-Symptomatic samples in 'Hamlin' dataset were identified as zinc deficient HLB positive which means their HLB infections were identified correctly. Only one magnesium deficient sample in 'Valencia' dataset was misclassified in HLB-symptomatic class which was a remarkable result because magnesium deficiency symptom in citrus leaf are very similar to HLB symptom. The classification rates in zinc deficient classes were usually lower than other classes since zinc deficiency symptom hid the HLB symptom in HLB positive ones.

TABLE 2-7

Number of samples in 'Hamlin' dataset which were classified into each of four classes and their classification accuracies and misclassification errors (%)

|  |  | Actual class | | | | |
|---|---|---|---|---|---|---|
|  |  | Healthy | HLB-Symptomatic | Zinc deficient HLB Negative | Zinc deficient HLB Positive | Sum |
| Prediction | Healthy | 32 (100.0%) | 2 (7.1%) | 0 | 0 | 34 |
|  | HLB-Symptomatic | 0 | 24 (85.7%) | 1 (6.7%) | 0 | 25 |
|  | Zinc Deficient HLB Negative | 0 | 0 | 14 (93.3%) | 3 (20.0%) | 17 |
|  | Zinc Deficient HLB Positive | 0 | 2 (7.1%) | 0 | 12 (80.0%) | 14 |
|  | Sum | 32 | 28 | 15 | 15 | 90 |

TABLE 2-8

Number of samples in 'Valencia' dataset which were classified into each of five classes and their classification accuracies and misclassification errors (%).

|  |  | Actual class | | | | | |
|---|---|---|---|---|---|---|---|
|  |  | Healthy | HLB-Symptomatic | Magnesium Deficient | Zinc Deficient HLB Negative | Zinc Deficient HLB Positive | Sum |
| Prediction | Healthy | 20 (100.0%) | 0 | 0 | 0 | 0 | 20 |
|  | HLB-Symptomatic | 0 | 20 (100.0%) | 1 (5.0%) | 1 (16.7%) | 3 (10.0%) | 25 |
|  | Magnesium Deficient | 0 | 0 | 19 (95.0%) | 0 | 0 | 19 |
|  | Zinc Deficient HLB Negative | 0 | 0 | 0 | 2 (33.3%) | 5 (16.7%) | 7 |
|  | Zinc Deficient HLB Positive | 0 | 0 | 0 | 3 (50.0%) | 22 (73.3%) | 25 |
|  | Sum | 20 | 20 | 20 | 6 | 30 | 96 |

Although the nutrient deficient classes were included in the datasets, the main purpose in this study was to detect the HLB infection and not the nutrient deficiency. Therefore, the contents in Tables 2-7 and 2-8 were merged into only two classes of HLB positive and HLB negative for each dataset (Table 2-9). Considering only the HLB detection, the average classification accuracies of 93.1% and 89.6% were achieved for 'Hamlin' and 'Valencia' datasets correspondingly.

TABLE 2-9

Number of samples classified into each of HLB positive or HLB negative classes, their classification accuracies and misclassification errors (%) regardless of their nutrient deficiency conditions for 'Hamlin' (left) and 'Valencia' (right) datasets

| | | 'Hamlin' Dataset | | | | | 'Valencia' Dataset | | |
|---|---|---|---|---|---|---|---|---|---|
| | | Actual | | | | | Actual | | |
| | | HLB Positive | HLB Negative | Sum | | | HLB Positive | HLB Negative | Sum |
| Prediction | HLB Positive | 38 (88.4%) | 1 (2.1%) | 39 | Prediction | HLB Positive | 45 (90.0%) | 5 (10.9%) | 51 |
| | HLB Negative | 5 (11.6%) | 46 (97.9%) | 51 | | HLB Negative | 5 (10.0%) | 41 (89.1%) | 39 |
| | sum | 43 | 47 | 90 | | sum | 47 | 43 | 90 |

Observations

This study, i.e., this Example, investigated the effect of starch accumulation of the HLB-symptomatic citrus leaves on the polarization planar of light in two specific wavelengths and employed it to develop a machine vision based sensing system which was able to distinguish between HLB-symptomatic and healthy leaves.

Generally, starch concentration for healthy sweet orange leaf samples should not exceed 5-7 $\mu g/mm^2$; however, our 'Hamlin' dataset contained one healthy and 11 zinc deficient HLB negative samples with starch concentrations higher than 7 $\mu g/mm^2$. Also, the starch concentrations in all six zinc deficient HLB negative samples of 'Valencia' dataset exceeded 7 $\mu g/mm^2$. This can be explained as either outliers or as HLB-symptomatic leaves not identified by qrt-PCR analysis due to the many inconsistencies brought about by internal biotic conditions, as per Gottwald (Gottwald, T. R., 2010, "Current Epidemiological Understanding of Citrus Huanglongbing" in, *Annual Review of Phytopathology*, 48: 119-139)(Gottwald 2010). However, most reasonable explanation relates to the bacteria life cycle. Visible symptoms of starch accumulation (indicating high starch content) only arise after phloem plugging, as per Schneider (Schneider, H., 1968, "Anatomy of greening-disease sweet orange shots" in, *Phytopathology*, 58: 1155-1160) (Schneider 1968); and Etxeberria, et al. (Etxeberria, E., P. Gonzalez, D. Achor, and G. Albrigo, 2009, "Anatomical distribution of abnormally high levels of starch in HLB-affected Valencia orange trees" in, *Physiological and Molecular Plant Pathology*, 74(1): 76-83) (Etxeberria, et al. 2009). During the process of phloem plugging and eventual collapse, CLas concentration declines, resulting in diminished DNA fingerprinting and lack of PCR detection, as per Folimonova and Achor (Folimonova, S. Y., Anchor, D. S., 2010, "Early Events of citrus greening (Hunglongbing) disease development at the ultrastructural level" in *Phytopath*, 100(9), 949-958, http://dx-.doi.org/10.1094/PHYTO-100-9-0949) (Folimonova and Achor 2010). At some point, this situation would result in CLas infected leaves with high levels of starch but no PCR positive signal. The reverse situation was also found. One HLB-symptomatic sample and one zinc deficient HLB positive sample in the 'Hamlin' dataset as well as four zinc deficient HLB positive samples in the 'Valencia' dataset, on the contrary, contained a starch concentration below than 7 $\mu g/mm^2$ which could be considered as an experimental error. However, the most reasonable explanation relates to the long latency period between HLB infection time and the starch accumulation symptom appearance. In such cases, early HLB infected leaves will give a positive PCR signal at times where starch accumulation is in early stages and has not reached the threshold level.

This determination indicated that 400 nm (Max), 400 nm (Min), and 591 nm (Max) images did not provide any useful information in the detection process. The results obtained in 400 nm illumination condition confirmed the preliminarily results in which the reflectance ratio between healthy and HLB-symptomatic samples was close to one. The pixel values of the glossy regions in 591 nm (Max) images were very similar to the pixel values of HLB-symptomatic or zinc deficient parts, and as a result, the information of these images was impractical. As expected from preliminarily results (FIGS. 3A-3D), the pixels belonging to healthy, HLB-symptomatic, and zinc deficient regions in 591 nm (Min) images were different (FIG. 9), but the classification based on these pixel values did not always result in an increased accuracy (FIG. 9). One important reason for this discrepancy might be due to the AGC effect which was not completely canceled in the calibration process. Leaf color inconsistency was also a minor reason for some samples. Consequently, a detection method based on image segmentation using a single threshold which can be applied to all leaf samples was not promising. Most of the image textural descriptors such as Local pattern based textural features are grayscale invariant, as per Ojala, et al. (Ojala, et al. 1996), and the overall image brightness does not affect them. Hence, they were chosen to be used in the detection process, and as a result, the detection accuracy increased significantly. Local pattern features (LBP and LSP) included more than half of the features which were used in zinc deficiency detection and also HLB detection within the non-zinc deficient class (Table 2-5) as well as all the three features employed in HLB detection within zinc deficiency class. Grayscale invariant textural features such as entropy (which defines the busy-ness of an image), smoothness and standard deviation (which depend on the image contrast) extracted directly from the images were also determined to be useful in zinc and HLB detection (Table 2-6). It was concluded that the symptomatic areas on infected leaves generated different measures of image busy-ness and contrast compared to healthy leaves. The small contribution of GLCM features in all detection processes established that the pixels' spatial relationships in healthy and symptomatic samples were not noticeably different compared to the other textural descriptors. The use of Mahalanobis classifier resulted in the best accuracies in all the classification steps in 'Hamlin' dataset and also the first classification step in 'Valencia' dataset.

The HLB detection accuracy within the zinc deficient class was comparatively lower than the one in the non-zinc deficient class in both datasets. This lower accuracy was expected because the zinc deficient leaves already included some higher intensity areas in the 591 nm (Min) images which were very similar to HLB-symptomatic areas, but unrelated to HLB infection. Additionally, according to tables 3 and 4, the starch accumulations within the zinc deficient classes (mostly in HLB negative classes) were usually inconsistent with the corresponding PCR test results. This might be another reason for the lower classification rates in zinc deficient classes.

In total, five HLB positive samples in each dataset were misclassified in the HLB negative classes which led to comparatively lower classification accuracies of 88.4%, and 90.0% for the HLB positive classes in 'Hamlin' and 'Valencia' datasets correspondingly. Three out of these five samples in 'Hamlin' dataset and all five samples in 'Valencia' dataset were within the zinc deficiency classes and as explained before, HLB detection for zinc deficient samples was less accurate. The measured starch concentrations for these samples were 2.63, 9.42, 12.49, 61.77, and 74.11 μg/mm$^2$ in 'Hamlin' dataset and 8.60, 10.69, 32.02, 47.12, and 51.53 μg/mm$^2$ in 'Valencia' dataset. One of the samples contained a starch concentration below the threshold (5 μg/mm$^2$) and the starch concentrations for five others were also below the average of the HLB-symptomatic class (37.4 μg/mm$^2$). Therefore, the comparatively low concentration of starch might be a likely reason of misclassification. On the other hand, one HLB negative sample in 'Hamlin' dataset and five HLB negative samples in 'Valencia' dataset (all in nutrient deficiency classes) were misclassified into the HLB positive classes. Although the CT value for these samples were "undetected" (which indicates they were not infected), their starch concentration was 0.52, 8.0, 10.69, 11.13, 12.79, 20.90, and 40.30 μg/mm$^2$ which were above the threshold for five of them. Therefore, there is a possibility that the qrt-PCR analysis did not recognize their HLB infection given the many stated inconsistencies outlined by Gottwald (Gottwald 2010) or, their starch concentrations were elevated due to a different biological reason, a different disease, or a deficiency.

None of the confirmation methods including crop scouting, starch measurement, and qrt-PCR analysis are 100% accurate, and no absolute, precise detection approach has been reported yet. Consequently, the evaluation of the proposed method was certainly under the influence of this inaccuracy. Additionally, the incomplete gain adjustment process might be another source of error. Using a camera without an AGC feature may resolve this problem and increase the accuracy.

The results of this study demonstrate that starch accumulation due to an HLB infection can be detected using polarizing filters in a citrus leaf image taken at 591 nm wavelength. The starch accumulation on HLB-symptomatic leaves rotates the polarization planar of the light mostly around 600 nm waveband and a reflectance measurement system was capable of sensing this polarization rotation. However, this rotation was more clearly detected using textural features extracted from leaf images acquired with a commercial camera and proper use of polarizing filters. On the contrary, using additional classes of nutrient deficient samples which had similar visual symptoms to HLB infection verified that this system detected the starch accumulation on citrus leaves regardless of their visual color.

The laboratory based detection methods such as qrt-PCR analysis and starch measurement may have higher accuracy; however, they are time and labor consuming and relatively expensive. Using spectroscopy approaches as per, Hawkins, et al. (Hawkins, S. A., B. Park, G. H. Poole, T. Gottwald, W. R. Windham, and K. C. Lawrence, 2010, "Detection of citrus huanglongbing by Fourier transform infrared-attenuated total reflection spectroscopy" in, *Applied Spectroscopy*, 64(1): 100-103)(Hawkins, et al. 2010), Sankaran, et al. (Sankaran, et al. 2011), and, Pereira, et al. (Pereira, et al. 2011) achieved up to 95% of accuracy in HLB detection; however, their proposed methods needed expensive equipment and trained staff. Li, et al. (Li, H., W. S. Lee, K. Wang, R. Ehsani, and C. Yang, 2013, "Extended spectral angle mapping (ESAM) for citrus greening disease detection using airborne hyperspectral imaging" in, *Precision Agriculture*, 1-22) (Li, et al. 2013) also showed that the HLB detection accuracy could increase up to 86% using an improved airborne image analysis method. Still airborne imaging is not affordable by every grower and the weather can limit its performance. In our study, an easy and inexpensive method was presented which can be used as a real time and portable in field diagnostic approach with acceptable accuracy. Additionally, the unique characteristic of starch which is accumulated in HLB-symptomatic leaves on polarized light was used successfully for the first time in a real time detection application.

III. System

Figure 11A:
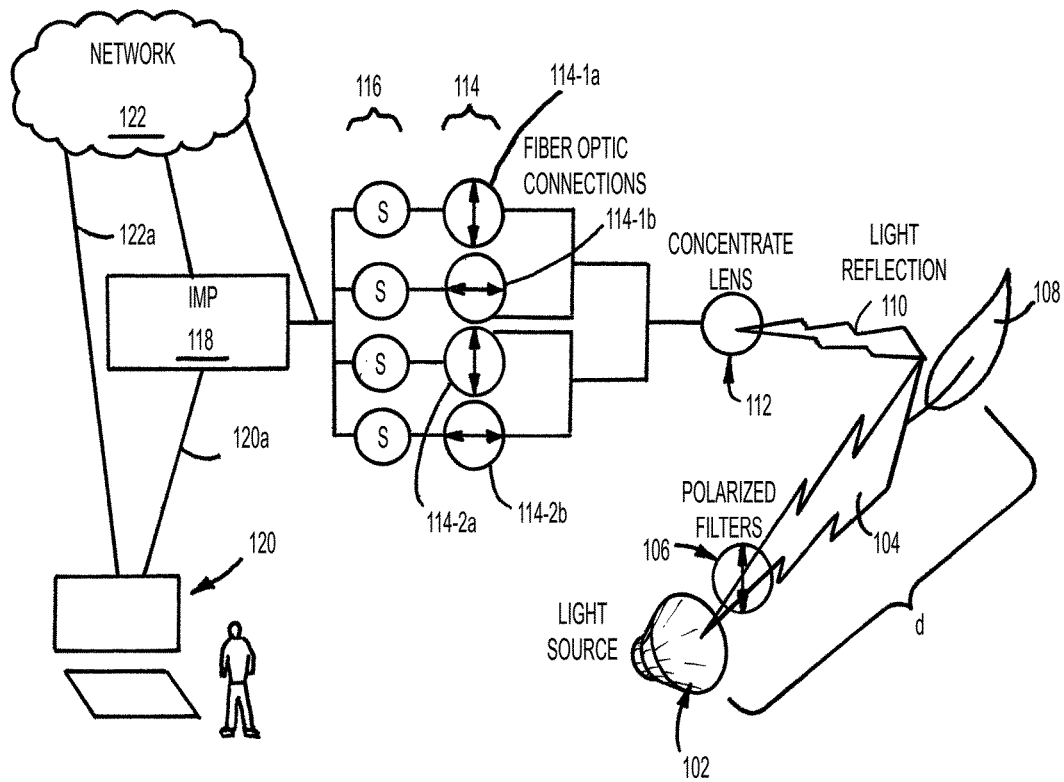
FIG. 11A is a schematic diagram of a system for performing the invention.

Attention is now directed to FIG. 11A, which is a diagram of an exemplary system 100 shown performing an embodiment of the invention. The system includes a light source 102, which outputs light, for example, as light beams 104, at wavelengths, for example, from approximately 300 nm to approximately 700 nm. For example, light may be output at 400 nm and 550 to 600 nm, and, id typically output at or approximately at 591 nm, the wavelength determined by the inventors as optimal for analysis of citrus leaves plants for HLB detection, as detailed above. A polarizer 106 is operatively coupled to the light source 102 and is oriented at a predetermined angle, with respect to the outputted light 104. For example, the predetermined angle of orientation is straight vertical, and assigned the value of 0 (zero) degrees.

The light source 102 is positioned at a predetermined distance "d" from a leaf 108, for which analysis is sought. This predetermined distance is, for example, for example, approximately 80 cm.

The light beam 104 reflects off of a leaf 108, such as a citrus leaf, with the reflected light beam 110 received in a lens 112, for example of a camera, including a charge coupled device (CCD) camera. Prior to passing through the lens 112, the reflected light 110 passes through a filter 114. The filter 114 is in a predetermined orientation, with respect to the orientation of the polarizer 106. For example, the filter 114 is which is shown is as grouped by light wavelengths, for example, two, two light wavelengths—filters 114-1, for approximately 400 nm wavelength light, and 114-2 for 591 nm wavelength light, with "a" filters 114-1a, 114-2a oriented at approximately 0 (zero) with respect to the orientation of the polarizer 106, and "b" filters 114-1b, 114-2b oriented at approximately 90 degrees or approximately perpendicular with respect to the orientation of the polarizer 106. Also, for example, the filters 114-2a, 114-2b, for 591 nm light are typically used with the system 100.

The light which passes through the filter 114 is received by sensors(S) 116, such as light intensity detectors, or other vision-based sensors, which analyze light intensity in pixels, linked, for example, to an image processor (IMP) 118. The image processor 118 is, for example, computerized and includes a processor and stored, machine executable instructions, for producing images, e.g., digital images, in gray scale, colors and the like, representative of light intensities for each of the pixels.

The sensors 116 and/or image processor 118, link to a computer 120, either directly (for example, via the link 120a), or via a network 122 (for example, via the link 122a), such as a local area network (LAN) and/or a wide area network (WAN), including public networks, such as the Internet, cellular networks and other communications networks, and combinations thereof.

Figure 12A:
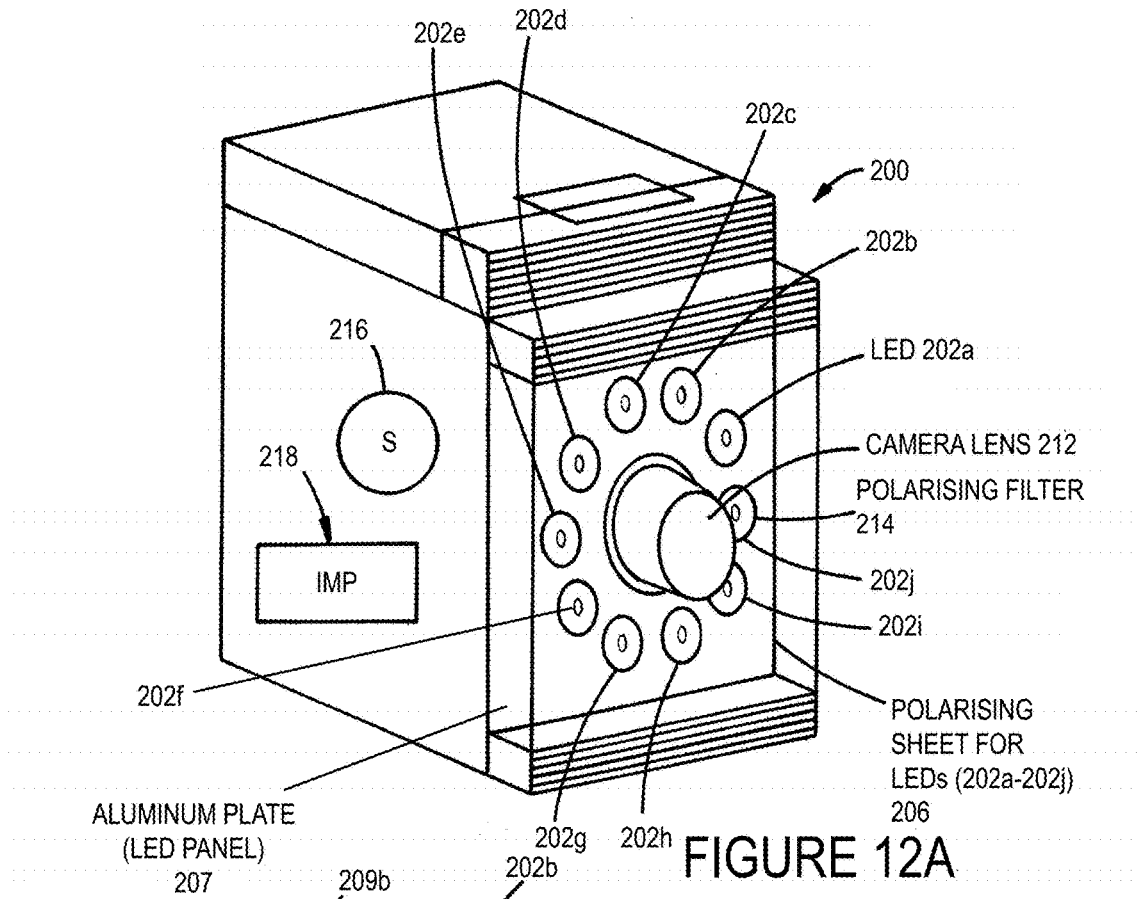
FIG. 12A is a diagram of a camera useful in the system of FIG. 11A.
Figure 12B:
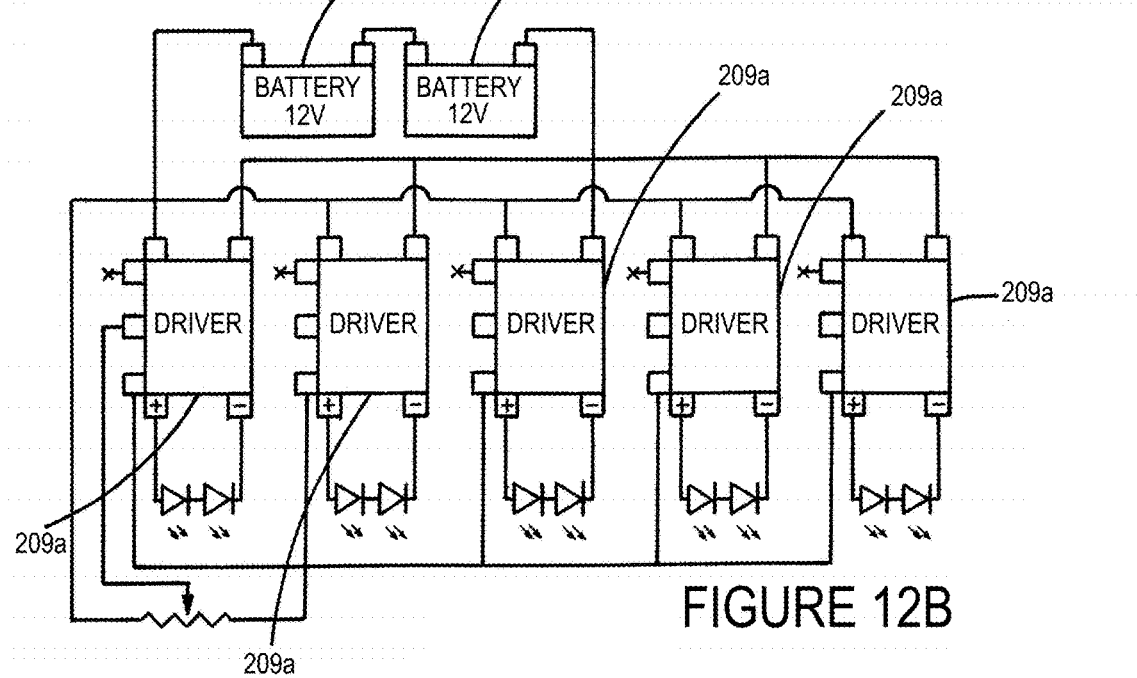
FIG. 12B is an electrical schematic for the camera of FIG. 12A.

The light source 102, polarizer 106, lens 112, filter 114, sensor 116, image processor 118 and other components necessary for creating images based light intensities, for example, pixilated, may be embodied on a CCD Camera, for example, as shown in FIGS. 12A and 12B.

Figure 11B:
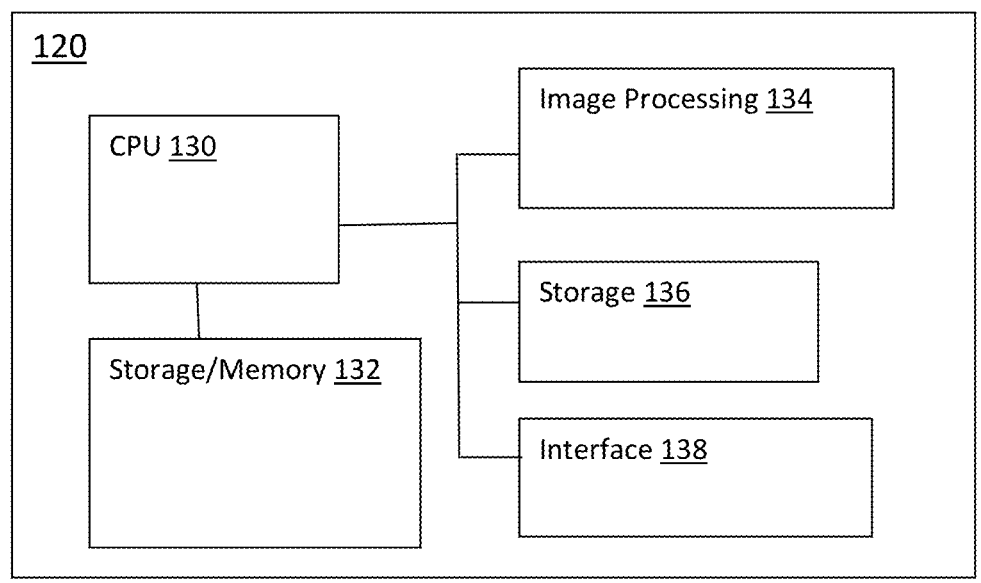
FIG. 11B is a diagram of the camera of the system of FIG. 11A.

As shown in FIG. 11B, the computer 120, for example, is processor based and includes a CPU (Central Processing Unit) 130 linked to storage/memory 132 for storing machine executable instructions executable by the processor(s) of the CPU 130. The computer 120 also may also include image processing module 134, and storage media 136 for storing data, such as sensor data and image data. There is also an interface 138 for facilitating interactions with other apparatus as well as over a network, such as the network 122. All of the processors, components and storage of the computer 120 are linked to each other, either directly or indirectly.

The CPU 130, coupled with the storage/memory 132, serve as an image analyzer and perform an image analysis process, for example, in the form of an algorithm, to detect, for example, the birefringent materials in images of leafs 108, captured by the sensor 116. This process is detailed further below.

FIGS. 12A and 12B are directed to a camera 200. For this camera 200, elements similar to those of the system above are the same numbers but in the "200s," and are in accordance with the corresponding descriptions, as provided above. Differences are noted below.

The camera 200 includes a light source 202a-202j, which are for example, light emitting diodes (LEDs). These LEDs 202a-202j emit light, for example, at 400 nm and 550 to 600 nm wavelengths, and, light is typically output at or approximately at 591 nm, the wavelength determined by the inventors as optimal for analysis of citrus leaves plants for HLB detection, as detailed above. The LEDs 202a-202j are mounted in an aluminum plate 207 on the camera 200. As shown in FIG. 12B, the LEDs 202a-202j are supplied power via drivers 209a, with one driver per two LEDs, and batteries 209b, for example, two 12 Volt batteries, in an electrical connection with the drivers 209a and LEDs 202a-202j.

A polarizer 206, in the form of a sheet, is placed over the LEDs 202a-202j. The polarizer 206 is operatively coupled to the light source 202a-202j and is oriented at a predetermined angle, with respect to the outputted light, defining, for example, a predetermined reference plane. For example, the predetermined angle of orientation for the polarizer 206 is straight vertical, and assigned the value of 0 (zero) degrees.

The camera 200 includes a lens 212, over which is a polarizer filter 214. The polarizer filter 214 is oriented at a predetermined angle with respect to the angle of the polarizer 206. For example, for light wavelengths of approximately 591 nm, this predetermined orientation of the polarizer 206 to the polarizing filter 214 is approximately 90 degrees or approximately perpendicular. Accordingly, the predetermined reference plane associated with the polarizer 206 is oriented approximately 90 degrees or approximately perpendicular to the plane of the polarizer filter 214.

Sensors (S) 216, such as light intensity detectors, which analyze light intensity in pixels, linked, for example, to an image processor (IMP) 218. The image processor 218 is, for example, computerized and includes a processor and stored, machine executable instructions, for producing images, e.g., digital images, in gray scale, colors and the like, representative of light intensities for each of the pixels. The camera 200 is such that it is placed in electronic and data communication with a computer, directly or indirectly, as detailed above, to perform embodiments of the invention.

Figure 13:
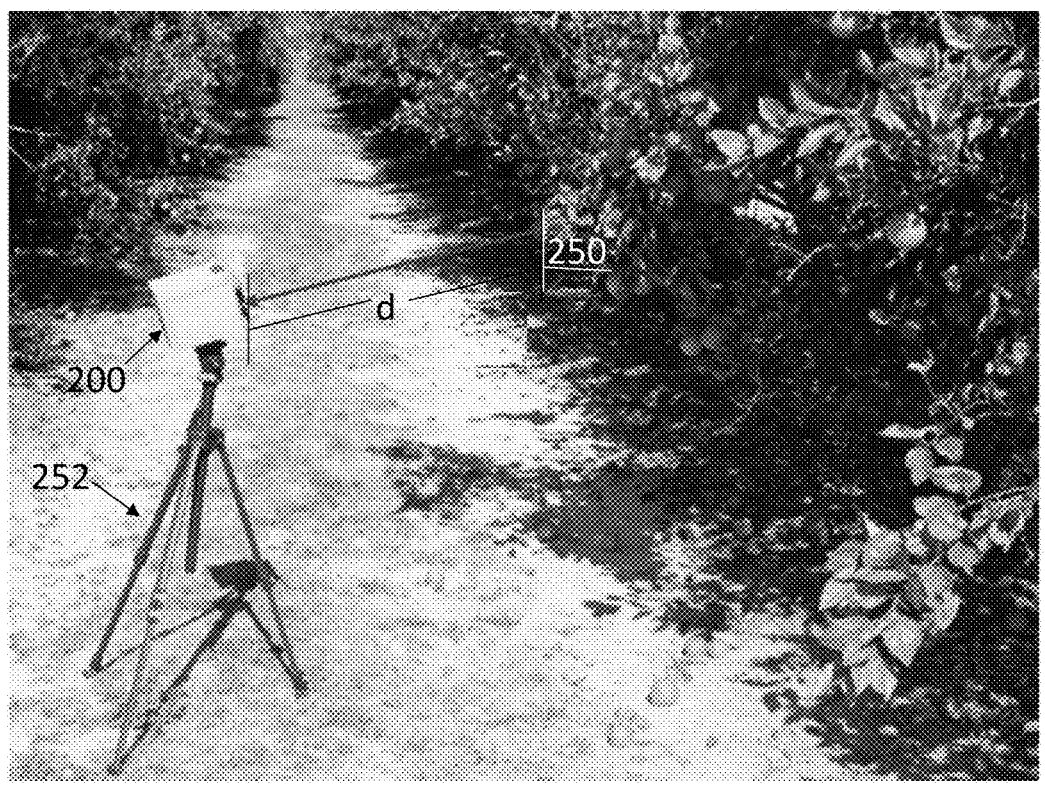
FIG. 13 is a photograph showing the camera of FIGS. 12A and 12B in an exemplary operation.

FIG. 13 shows the camera 200 in operation, performing imaging of citrus leafs, on a citrus tree 250. The camera 200 is mounted on a tripod 252 or other similar mount, and, from a distance "d" emits light and receives the reflected light, from which a determination of HLB status is made for that particular tree 250. For example, the distance "d" is approximately 80 cm.

III. Image Analysis

Figure 14:
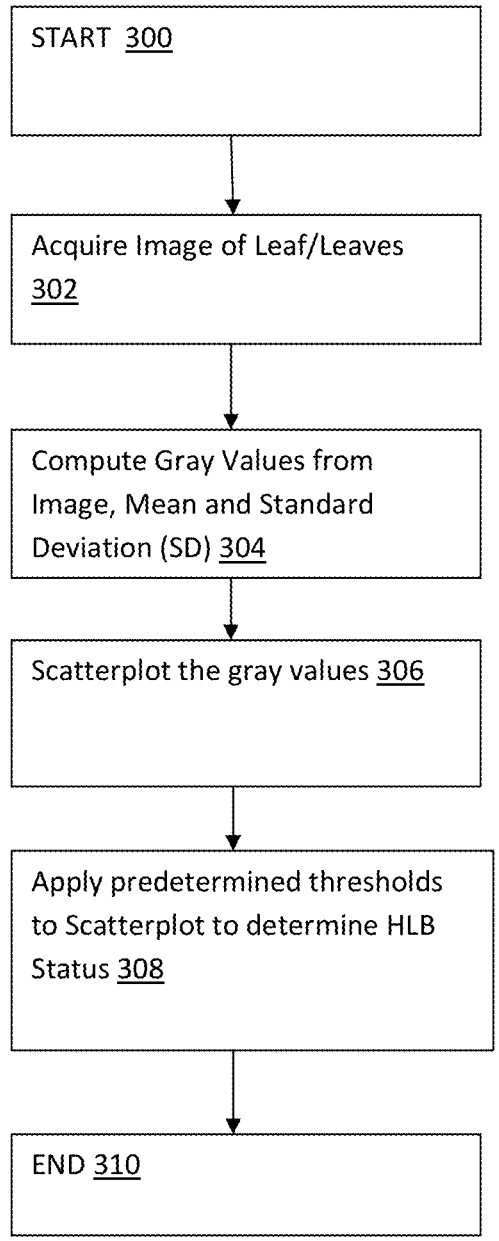
FIG. 14 is a flow diagram of a process in accordance with embodiments of the present invention.

Attention is now directed to FIG. 14, which shows a flow diagram detailing a computer-implemented process for image analysis, for example, image analysis to detect the birefringent materials in an image captured by the camera 200, via its sensors, in accordance with embodiments of the disclosed subject matter. The process and subprocesses of FIG. 14 are computerized process, performed by the computer 120, as detailed above. The aforementioned processes and sub-processes can be, for example, performed manually, automatically, or a combination thereof, and, for example, in real time.

The process begins at a START block 300. Here, any preconditions are satisfied and accommodated. The process moves to block 302 where images of leaves are acquired by the camera 200, or other imaging device. The process moves to block 304, where the gray values from the image are computed, these values including the mean and standard deviation (SD), which for the respective vertical (y) and horizontal (x) axes of a histogram.

The process moves to block 306, where the gray values from block 304 are placed on a scatterplot. The process moves to block 308, where predetermined thresholds, formed by processes, such as machine learning, are applied to the scatterplot data to determine HLB status for each of the data points, corresponding to an imaged leaf. With the HLB status determined from the scatterpoint position with respect to the threshold, the process moves to block 310, where it ends.

An example process, including the aforementioned image analysis, is detailed in Example 3.

Example 3

A. Materials and Methods i. Vision Sensor

As shown in Example 1 above, the starch accumulation in HLB-positive leaves can rotate the polarization planar of light by 90 degrees at 591 nm. This property was used to design the vision sensor enclosed in a wooden box (13×19× 15 cm) including a camera and an illumination system, similar to that of FIGS. 12A and 12B, and with the components as below. A highly sensitive monochrome camera (DMK 23G445, TheImagingSource, Bremen, Germany) with an ICX445 Sony CCD sensor was used to measure the leaf reflectance. The spectral sensitivity curve of this CCD sensor had the quantum efficiency of >90% at 591 nm which made it an appropriate option for our purpose. The camera was equipped with a wide lens (6 mm focal length) that created a diagonal field of view of 53.1° and a rotating linear polarizer and mounted inside the vision sensor housing. The very short focal length was selected to increase the depth-of-field so that more objects with different depths were in focus. FIG. 12A also shows the LED panel of the vision sensor. Ten high luminous efficiency LEDs (LED Engin, San Jose, Calif.) at 591 nm (LZ4-00A100, 10 W) were mounted on an aluminum plate in a circular pattern. The LEDs were powered with two 12 V car batteries (24 V in total) in series and five 70 W LED drivers (RCD-48, RECOM, Brooklyn, N.Y.) in parallel as shown in FIG. 12B. The LED panel was fixed on a side of the vision sensor, and a polarizing film (visible linear polarizing laminated film, Edmund Optics, Barrington, N.J.) was mounted in front of it. A hole in the center of the LED panel and another one in the center of the polarizing film were cut so that there was enough room for the camera lens to come out. The direction of the camera's linear polarizer was set to be perpendicular to the direction of the LEDs' polarizing film as illustrated in FIG. 12A. Therefore, the camera was only able to receive the minimum reflection.

ii. Data Collection

A set of citrus leaf samples (Hamlin' sweet orange) was collected from a grove at the Citrus Research and Education Center (CREC), University of Florida (Lake Alfred, Fla.) in September of 2013 by experienced HLB researchers. An experiment was conducted by acquiring images of 60 citrus leaf samples from four classes: HLB-negative (20 samples), HLB-positive (20 samples), zinc deficient HLB-negative (10 samples), and zinc deficient HLB-positive (10 samples) in a laboratory.

An in-field experiment was conducted in the CREC grove in November of 2013 in which 20 images of HLB-positive citrus trees and 10 images of HLB-negative citrus trees (the control) were acquired. Eight out of 20 samples in the HLB-positive class were also zinc deficient. The citrus trees and target leaves were located and marked by experienced researchers in the morning before the image acquisition. In order to verify the HLB status of the samples, a qrt-PCR test, as per Hansen, et al. (Hansen, A., Trumble, J., Stouthamer, R., Paine, T., 2008, "A new huanglongbing species, "*Candidatus Liberibacter psyllaurous*," found to infect tomato and potato, is vectored by the psyllid *Bactericera cockerelli* (Sulc)" in, *Applied and Environmental Microbiology*, 74, 5862)(Hansen, et al. 2008) was performed on a total of 90 samples, including 60 of the in-lab experiment samples and one leaf sample from each image in the in-field experiment. The qrt-PCR test was conducted at the United States Sugar Corporation (USSC), Technical Operations, Southern Gardens (Clewiston, Fla.).

iii. In-Lab Experiment

The lab experiment was conducted to evaluate several simulations of field imaging conditions and to determine the best settings for the sensor. Since the vision sensor had its own illumination system, the in-field experiment was conducted after sunset to prevent any interference from sunlight. Therefore, the lab experiment was conducted in a completely dark room to simulate real lighting conditions. An exposure time of 0.1 seconds was set for the camera because this was the shortest exposure time for capturing visually informative images without adding any gain (which increases the noise level). In order to determine the effect of the object depth on its histogram features, the images of one leaf were acquired from different distances, ranging from 50 cm to 150 cm. Then the histograms of the images taken at different depths were plotted and compared with each other. Two main histogram features including mean and standard deviation (SD) were considered for this evaluation, and the relationships between these features and the object depth was modeled.

All image acquisitions for the in-lab experiment were designed to be conducted with a fixed depth, assuming that the mean and SD features of any leaf at different depths can be computed accurately with its known depth.

In order to determine the optimum distance, three distances (60 cm, 80 cm, and 100 cm) were examined. Also, four leaf positioning conditions, including separated, adjacent, and overlapped leaves as well as the leaves on an artificial citrus tree were defined to evaluate how the leaf position in the image can influence the detection accuracy.

A circular area on each leaf was randomly selected from the symptomatic areas of HLB-positive and zinc-deficient samples, as well as a random area of HLB-negative samples. In order to select the same spot on the images of the same leaf taken from three different distances, the sizes of 177, 112, and 52 pixels were chosen for the circular areas on the images taken from 60 cm, 80 cm, and 100 cm, respectively. Then, the histograms of the two symptomatic areas and the HLB-negative regions were compared to each other to illustrate the dissimilarity of the histograms of the three different types of leaves. In order to determine whether the positioning condition of the leaves affects the identification accuracy of the symptomatic areas, a probability-based color transfer function was developed according to the histograms of symptomatic areas. In this function, three probabilities (corresponding to the three classes) were defined for each pixel value based on the histogram analysis (Equations 19 and 20):

$$P_c(i) = \frac{H_c(i)}{\sum_{n \in C} H_n(i)} \forall\ C = \{HLB-, HLN+, ZnDef.\} \quad (19)$$

$$P_{HLB-}(i) + P_{HLB+}(i) + P_{ZnDef.}(i) = 1 \quad (20)$$

where i is a gray value between zero and 255, $P_c(i)$ indicates the probability that pixel value i belongs to class c, and $H_c(i)$ is the histogram value of class c for pixel value i. Then, a color transfer function was developed based on these probabilities to convert the grayscale image to a red (R), green (G), and blue (B) image in which the amount of R, G, and B represents the probabilities of HLB infection, healthiness, and zinc deficiency, respectively.

iv. In-Field Experiment

In order to test the sensor in real in-field conditions, the images of citrus trees were acquired after sunset. Images were taken at an average distance of 80 cm from the trees and from the exact distance of 80 cm (80 cm=d) from the target leaves (FIG. 13). The target leaf from each image was marked and collected for a qrt-PCR test to validate its HLB status. The normalized histogram of the target leaf area in each image was obtained for further analysis.

v. Data Analysis and Classification

Two simple statistical histogram features, the mean and SD of the gray value (Equations 21 and 22), were extracted from the normalized histograms (h(i)), as per Pourreza, et al.

(Pourreza and Pourreza, et al, 2012), individual leaves and leaves on the artificial tree from the lab dataset and the target leaves from field dataset.

$$\text{Mean of the gray values: } \mu = \Sigma_i i h(i) \quad (21)$$

$$\text{SD of the gray values: } \sigma = \sqrt{\Sigma_i (i-\mu)^2 h(i)} \quad (22)$$

In order to evaluate the separability between the classes, a two-dimensional plot of the samples based on their means and SDs was used. Then, a maximum margin method, as per Bishop (Bishop 2006), was conducted to find the best divider threshold line between the classes. In this method, an objective function tries to find the optimum divider threshold which maximizes the margin between each pair of classes. A step-by-step classification model was designed based on the scatterplots of samples, as shown in FIG. 15. FIG. 15 shows a step-by-step classification model. In each step, the input samples were divided into two parts and at the final step all the dataset were divided into four classes.

A Support vector machine (SVM), which is also a maximum margin classifier, was trained with means and SDs features and employed for all steps of the classification model. A three-fold cross validation method was employed in the classification process in which the dataset was randomly divided into three folds, which two folds were used for training while the other fold was used for validation. This algorithm was repeated fifty times, and the average accuracies were calculated for each class.

All the data analyses and feature extractions were performed in MATLAB (version R2011a, MathWorks, Natick, Mass.). Also, the plot visualizations of the features were carried out in Excel (Microsoft Office, Microsoft, Redmond, Wash.).

B. Results i. Dataset Validation

The cycle threshold (CT value) in a qrt-PCR test indicates the number of required cycles for the fluorescent intensity to reach the threshold. The threshold of 33 was selected for CT values to determine the HLB status of the samples, as per Li, et al. (Li, et al. 2006). In other words, the samples with CT values below 33 were considered as HLB-positive leaves. Table 3-1 illustrates the interpretation of the CT values and HLB status for the samples used for the in-lab experiment. The CT values in all HLB-negative samples were above 33 which confirmed they were not infected. Also, all HLB-positive samples had CT values below 33 which verified their HLB infection. The CT values for half of the zinc-deficient samples were below 33 and those of the other half were above 33. Thus, there were 10 HLB-positive and 10 HLB-negative samples within the zinc deficient class.

TABLE 3-1

The qrt-PCR test results for citrus leaf samples in the lab experiment

| ID | CT Value | HLB Status |
|---|---|---|
| Zinc-deficient samples | | |
| 1 | 40.0 | − |
| 2 | 24.9 | + |
| 3 | 37.7 | − |
| 4 | 40.0 | − |
| 5 | 40.0 | − |
| 6 | 23.3 | + |
| 7 | 40.0 | − |
| 8 | 23.6 | + |
| 9 | 22.6 | + |
| 10 | 40.0 | − |
| 11 | 27.8 | + |
| 12 | 40.0 | − |
| 13 | 24.6 | + |
| 14 | 23.2 | + |
| 15 | 40.0 | − |
| 16 | 40.0 | − |
| 17 | 40.0 | − |
| 18 | 22.1 | + |
| 19 | 24.3 | + |
| 20 | 21.4 | + |

| ID | CT Value |
|---|---|
| HLB-negative samples | |
| 21 | 40.0 |
| 22 | 40.0 |
| 23 | 40.0 |
| 24 | 40.0 |
| 25 | 40.0 |
| 26 | 40.0 |
| 27 | 40.0 |
| 28 | 40.0 |
| 29 | 40.0 |
| 30 | 40.0 |
| 31 | 40.0 |
| 32 | 40.0 |
| 33 | 40.0 |
| 34 | 36.5 |
| 35 | 40.0 |
| 36 | 40.0 |
| 37 | 40.0 |
| 38 | 40.0 |
| 39 | 40.0 |
| 40 | 40.0 |
| HLB-positive samples | |
| 41 | 28.0 |
| 42 | 23.2 |
| 43 | 25.4 |
| 44 | 32.3 |
| 45 | 21.9 |
| 46 | 21.5 |
| 47 | 22.3 |
| 48 | 26.5 |
| 49 | 24.4 |
| 50 | 23.1 |
| 51 | 21.9 |
| 52 | 30.8 |
| 53 | 24.8 |
| 54 | 22.0 |
| 55 | 22.7 |
| 56 | 23.2 |
| 57 | 26.6 |
| 58 | 21.9 |
| 59 | 22.8 |
| 60 | 21.9 |

Table 3-2 shows the CT values for the samples in the field experiment dataset. The CT values for ten samples were above 33, so they were categorized as the HLB-negative samples. Sample numbers one to 20 had CT values below 33, and they were considered as HLB-negative. Eight out of 20 HLB-positive samples were also zinc-deficient, and they were categorized in another subclass of HLB-positive zinc-deficient samples. Since all the zinc-deficient samples had CT values below 33, there was no zinc-deficient HLB-negative class in this dataset.

TABLE 3-2

The qrt-PCR test results for citrus leaf samples in the field experiment

| HLB-positive Samples | | | | HLB-negative samples | |
|---|---|---|---|---|---|
| Non-zinc deficient | | Zinc-deficient | | | |
| ID | CT value | ID | CT Value | ID | CT Value |
| 1 | 21.9 | 9 | 20.7 | 21 | 40.0 |
| 2 | 24.1 | 10 | 26.0 | 22 | 40.0 |
| 3 | 24.3 | 11 | 24.2 | 23 | 36.0 |
| 4 | 21.0 | 15 | 23.2 | 24 | 37.2 |
| 5 | 19.5 | 16 | 26.5 | 25 | 40.0 |
| 6 | 22.4 | 17 | 23.3 | 26 | 36.2 |
| 7 | 22.9 | 18 | 22.4 | 27 | 40.0 |
| 8 | 23.0 | 20 | 21.5 | 28 | 40.0 |
| 12 | 24.3 | | | 29 | 40.0 |
| 13 | 26.1 | | | 30 | 40.0 |
| 14 | 22.6 | | | | |
| 19 | 21.4 | | | | | ii. In-Lab Experimental Results a) The Object Depth Effect

FIGS. 16A and 16b show the leaf sample that was used for the object depth effect evaluation. FIG. 16A shows normalized histograms of the leaf sample images acquired from several distances between 50 cm to 150 cm. FIG. 16B shows color image of the sample and its gray images acquired from several distances between 50 cm to 150 cm.

Figure 17:
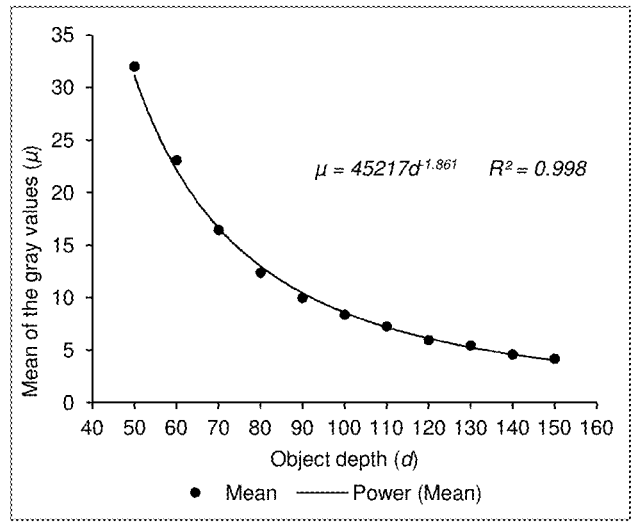
FIG. 17 is a power regression line fit curve for means values, as per Example 3.
Figure 18:
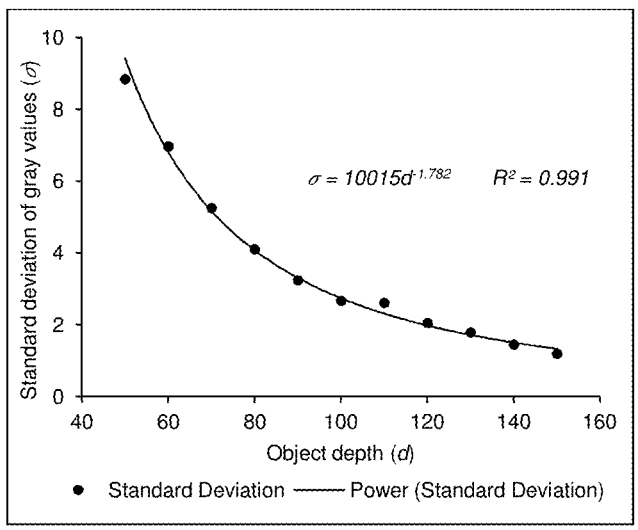
FIG. 18 is a power regression line fit curve for SD (Standard Deviation) values, as per Example 3.

FIG. 16A shows the leaf sample which was used to evaluate the effect of depth and gray images acquired at different depths. In order to find the relationship between the object depth and histogram features (mean and SD), a power regression method, as per Gennadios, et al. (Gennadios, A., Ghorpade, V., Weller, C. L., Hanna, M., 1996, "Heat curing of soy protein films" in *Biological Systems Engineering: Papers and Publications*, 94) (Gennadios, et al. 1996) was employed in Excel. FIG. 17 and FIG. 18 show a line fit, regression equation, and a coefficient of determination ($R^2$) value for mean ($\mu$) and SD ($\sigma$) based on the object depth (d). These curves and the very close coefficients of determination to the value of one confirmed the close relationship between the object depth and its histogram features. Therefore, these equations can be used for feature calibration as the pre-processing step for an on-the-go HLB diagnosis system when the depth information is available.

Figure 19A:
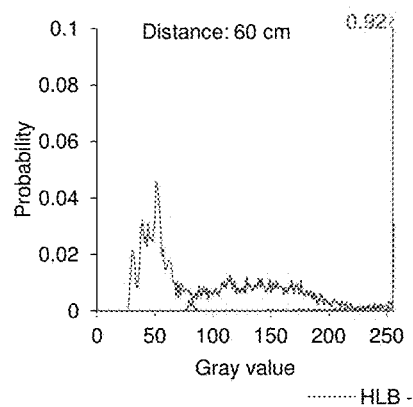
FIGS. 19A-19C are comparisons of histogram curves in three classes, in Example 3.
Figure 19B:
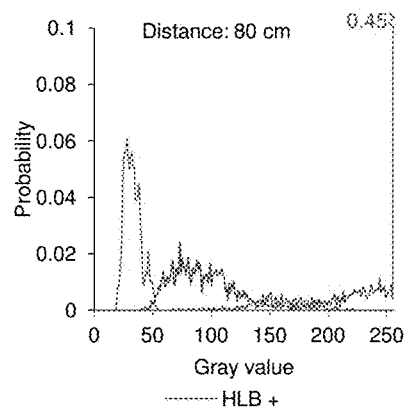
Figure 19C:
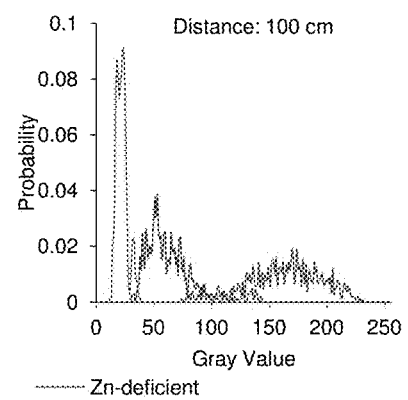

FIGS. 19A-19c show the positioning of the leaf, as comparisons of the histogram curves of symptomatic areas in three classes (HLB-negative, HLB-positive, and zinc-deficient) and at three different distances (60 cm (FIG. 19A), 80 cm (FIG. 19B), and 100 cm (FIG. 19C)). FIGS. 19A-19C show the normalized histograms of HLB-negative, HLB-positive, and zinc-deficient symptomatic areas at three different distances: 60 cm, 80 cm, and 100 cm. The histograms of three classes were distinctive at all distances with a few overlaps; however, the range of the gray values at the distance of 100 cm was shorter than the other two distances which increased the amount of overlap between neighboring curves. At the distance of 60 cm, 92% of pixels in the zinc-deficient class were saturated (gray value $\geq 255$) which overlapped with 3% of pixels in the HLB-positive. At the distance of 80 cm, 45% of zinc deficient pixels were also saturated; however, they did not overlap with the HLB-positive pixels. The maximum range of the gray values ($\{\max(i|h(i)\neq 0) - \min(i|h(i)\neq 0)\}$) was obtained at the distance of 80 cm as well. Therefore, the distance of 80 cm was chosen as the optimum distance for HLB identification in both field and lab experiments.

b) The Positioning Effect of the Leaf

Figure 20:
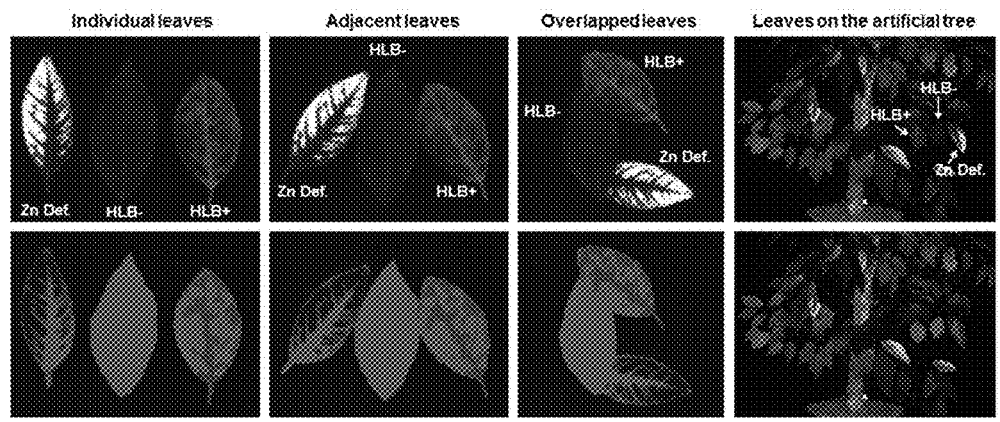
FIG. 20 is a photograph of symptomatic areas detection results, as per Example 3.

FIG. 20 shows symptomatic areas detection results for three leaf samples (one sample from each class) in four different leaf-positioning conditions. The green, red, and blue colors indicate the HLB-negative, HLB-positive, and zinc-deficient areas, respectively) shows three samples, one from each class: zinc-deficient, HLB-negative, and HLB-positive, in four leaf-positioning conditions: individual, adjacent, overlapped, and leaves on the artificial tree. The corresponding RGB images at each leaf positioning condition were created using the color transfer function in which the green, red, and blue colors indicate the HLB-negative, HLB-positive, and zinc-deficient areas, respectively. The color transfer function was able to detect the symptomatic areas in all leaf positioning conditions.

c) Histogram Features and Classification Results

The features of the mean and SD (Standard Deviation) of the gray values which were extracted from the normalized histograms of the images of the citrus leaves in the dataset for the in-lab experiment are shown in Table 3-3. Both features for healthy samples in both leaf positioning conditions (individual leaves and leaves on the artificial tree) were generally smaller than HLB-positive and zinc-deficient samples. Also, these features were normally greater in zinc-deficient samples compared to HLB-positive samples. A comparison between the features of the same leaves in the two different leaf positioning conditions indicated that the sample images acquired on the artificial tree had smaller gray value means for 83% of samples (50 out of 60 samples) and also smaller gray value SDs for 78% of samples (47 out of 60 samples).

TABLE 3-3

The mean and SD gray value features extracted from the normalized histogram of images of the leaf samples from the in-lab dataset

| | | Zinc-deficient samples | | | |
|---|---|---|---|---|---|
| | | $\mu^a$ | | $\sigma^b$ | |
| ID | HLB | Ind$^c$ | FT$^d$ | Ind. | FT |
| 1 | − | 84.7 | 55.4 | 65.8 | 35.2 |
| 2 | + | 100.4 | 71.5 | 42.6 | 31.1 |
| 3 | − | 110.3 | 79.3 | 65.7 | 52.7 |
| 4 | − | 89.4 | 114.5 | 58.6 | 66.2 |
| 5 | − | 107.9 | 104.7 | 58.6 | 51.9 |
| 6 | + | 114.8 | 119.6 | 37.1 | 49.1 |
| 7 | − | 121.4 | 112.2 | 85.4 | 78.8 |
| 8 | + | 121.0 | 86.9 | 44.1 | 38.2 |
| 9 | + | 213.8 | 212.9 | 59.0 | 50.3 |
| 10 | − | 127.5 | 122.0 | 77.5 | 71.8 |
| 11 | + | 102.9 | 92.0 | 62.4 | 57.5 |
| 12 | − | 119.4 | 111.1 | 82.2 | 71.6 |
| 13 | + | 140.9 | 93.4 | 65.7 | 53.7 |
| 14 | + | 134.5 | 111.3 | 64.3 | 53.3 |
| 15 | − | 98.0 | 77.3 | 55.3 | 41.1 |
| 16 | − | 128.6 | 108.6 | 69.2 | 61.4 |
| 17 | − | 89.3 | 65.9 | 63.7 | 40.3 |
| 18 | + | 98.7 | 85.6 | 44.5 | 36.8 |
| 19 | + | 162.1 | 159.1 | 64.5 | 65.5 |
| 20 | + | 162.3 | 149.7 | 49.7 | 45.1 |
| Average | | 121.4 | 106.6 | 60.8 | 52.6 |

TABLE 3-3-continued

The mean and SD gray value features extracted from the normalized histogram of images of the leaf samples from the in-lab dataset

| ID | μ Ind. | μ FT | σ Ind. | σ FT |
|---|---|---|---|---|
| HLB-negative samples | | | | |
| 21 | 38.3 | 38.1 | 5.7 | 8.1 |
| 22 | 28.4 | 16.8 | 4.2 | 3.8 |
| 23 | 49.5 | 32.0 | 8.0 | 4.9 |
| 24 | 26.5 | 26.1 | 3.7 | 5.5 |
| 25 | 20.9 | 21.5 | 4.7 | 4.2 |
| 26 | 26.8 | 29.2 | 4.9 | 4.5 |
| 27 | 28.0 | 24.1 | 3.2 | 3.0 |
| 28 | 26.3 | 19.4 | 4.8 | 3.2 |
| 29 | 23.1 | 24.6 | 3.8 | 4.4 |
| 30 | 23.7 | 28.2 | 3.8 | 5.5 |
| 31 | 35.8 | 31.1 | 4.0 | 4.4 |
| 32 | 34.3 | 23.9 | 5.1 | 3.5 |
| 33 | 30.2 | 17.5 | 4.8 | 2.6 |
| 34 | 29.3 | 25.9 | 6.0 | 4.5 |
| 35 | 33.7 | 24.9 | 4.7 | 3.9 |
| 36 | 26.2 | 22.7 | 5.6 | 3.5 |
| 37 | 31.9 | 21.9 | 5.3 | 4.0 |
| 38 | 36.6 | 30.8 | 5.1 | 4.8 |
| 39 | 41.8 | 36.7 | 4.5 | 6.0 |
| 40 | 34.3 | 28.6 | 6.6 | 4.3 |
|    | 31.3 | 26.2 | 4.9 | 4.4 |
| HLB-positive samples | | | | |
| 41 | 48.5 | 37.9 | 14.8 | 13.6 |
| 42 | 51.5 | 33.6 | 14.9 | 10.0 |
| 43 | 78.7 | 48.3 | 38.9 | 20.5 |
| 44 | 59.7 | 51.3 | 18.8 | 17.1 |
| 45 | 63.8 | 57.3 | 26.9 | 24.6 |
| 46 | 49.3 | 56.8 | 13.6 | 14.2 |
| 47 | 46.2 | 41.2 | 12.7 | 9.7 |
| 48 | 53.4 | 36.9 | 13.5 | 9.6 |
| 49 | 52.2 | 54.2 | 23.7 | 22.8 |
| 50 | 51.8 | 54.4 | 15.6 | 16.0 |
| 51 | 81.2 | 75.9 | 23.0 | 23.6 |
| 52 | 47.8 | 36.9 | 21.1 | 14.4 |
| 53 | 56.1 | 41.3 | 18.7 | 14.1 |
| 54 | 76.0 | 62.7 | 17.8 | 13.9 |
| 55 | 57.5 | 45.7 | 11.0 | 8.2 |
| 56 | 64.1 | 60.3 | 17.3 | 15.0 |
| 57 | 69.0 | 45.4 | 15.5 | 10.2 |
| 58 | 103.5 | 89.6 | 39.9 | 34.4 |
| 59 | 47.8 | 52.9 | 12.1 | 13.4 |
| 60 | 52.9 | 43.2 | 18.4 | 12.0 |
|    | 60.6 | 51.3 | 19.4 | 15.9 |

Figure 21:
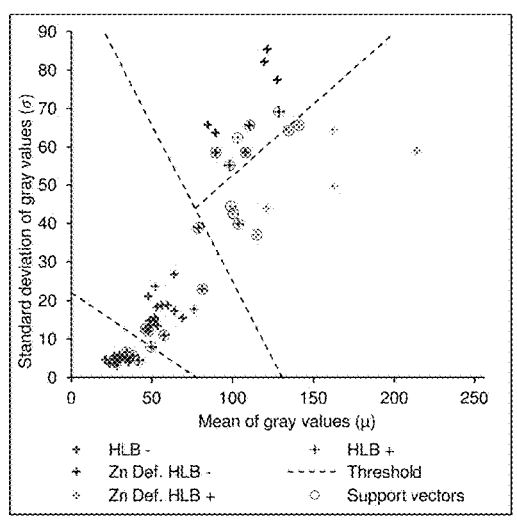
FIG. 21 illustrates a scatter plot of samples in four classes based on the means and SDs of the gray values for the images of individual leaves of Example 3.

[a] μ: The mean of the gray values
[b] σ: The SD of the gray values
[c] Ind.: Images of individual leaves
[d] FT: Images of leaves on the artificial tree FIG. 21 illustrates a scatter plot of samples in four classes based on the means and SDs of the gray values for the images of the individual leaves. This plot shows a clear distinction between the HLB-negative class compared to the HLB-positive and zinc-deficient classes. Three linear thresholds were acquired from the maximum margin method and used to divide all samples into four classes of HLB-negative, HLB-positive, zinc-deficient HLB-negative, and zinc-deficient HLB-positive. The sample number 23 had the maximum SD value equal to 8.0 in the HLB-negative class (table 3), while the minimum SD value of the classes was 11.0, which belonged to the sample number 55 in the HLB-positive class. A linear threshold ($\sigma_1=-0.28\mu+22$) separated the HLB negative samples from the rest of the dataset. The zinc-deficient samples generally had larger mean and SD values compared to the HLB-positive samples. A second linear threshold ($\sigma_2=-0.81\mu+106.43$) separated the HLB-positive samples from the zinc-deficient leaves with one misidentified HLB positive sample (#58). The last threshold was set within the zinc-deficient class ($\sigma_3=0.37\mu+15.43$) to identify the HLB-positive samples in this class. Using the optimum threshold, only one zinc-deficient HLB-positive leaf sample (#11) was misidentified in the zinc-deficient HLB-negative class.

Figure 22:
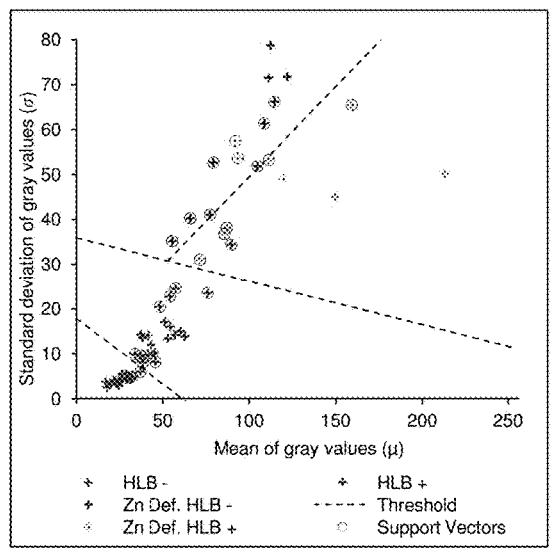
FIG. 22 shows a scatter plot of the samples in four classes based on the means and SDs of the gray value for the leaf images on an artificial tree of Example 3.

FIG. 22 shows a scatter plot of the samples in four classes based on the means and SDs of the gray value for the leaf images on the artificial tree. The maximum SD value in the HLB negative class (sample #21) was equal to 8.1, and it was smaller than the minimum SD value in the other classes (sample #55) which was equal to 8.2. However, sample #21 was misidentified as belonging to the HLB-positive class using the first linear threshold ($\alpha_1=-0.3\mu+17.74$) because it was considered to be a trade-off by the maximum margin method to create a more general threshold. The second threshold ($\sigma_2=-0.1\mu+35.89$) was set between the HLB-positive and zinc-deficient samples which resulted in one misidentified HLB-positive leaf sample (#58). The HLB-positive and HLB-negative samples within the zinc-deficient class were closer to each other in the scatter plot of the leaves on the artificial tree compared to the individual leaves. The best possible threshold ($\sigma_3=0.4\mu+11.78$) was able to separate these two subclasses with two misidentified zinc-deficient HLB positive samples (#11 and #13).

As FIG. 21 suggests, except for one HLB-positive sample and one zinc-deficient HLB-positive sample, all other samples were classified correctly in this dataset. Table 3-4 shows the classification results confusion matrix for the data sets of individual leaves. On average, 0.33 HLB-positive samples and 0.33 zinc-deficient HLB-positive samples were misclassified in a three-fold cross-validation. An overall accuracy of 97% was achieved using the proposed classification model and the mean and SD features. However, the purpose in this research was to detect HLB-infection. As long as the average of 0.33 HLB-positive samples was misclassified in another HLB-positive class (zinc-deficient), their HLB statuses were identified correctly. The dotted lines in Table 3-4 (and also table 3-5) separated the HLB-positive classes from HLB-negative classes. Therefore, the overall accuracy of 98.5% was obtained when only HLB-infection was considered in the classification results evaluation.

TABLE 3-4

Average number of samples in the individual leaves dataset which were classified into the four classes and their corresponding classification accuracies and misclassification errors (%). The last row and column illustrate the sum of samples in the corresponding rows or columns

| | | Actual Class | | | | |
|---|---|---|---|---|---|---|
| | | HLB+ | Zn Def. HLB+ | Zn Def. HLB− | HLB− | Sum |
| Prediction | HLB+ | 6.67 (95.29%) | | | | 6.67 |
| | Zn Def. HLB+ | 0.33 (4.71%) | 3.67 (91.75%) | | | 4 |
| | Zn Def. HLB− | | 0.33 (8.25%) | 4 (100%) | | 4.33 |
| | HLB− | | | | 7 (100%) | 7 |
| | Sum | 7 | 4 | 4 | 7 | 22 |

Based on FIG. 22, one HLB-positive sample was misidentified in the zinc-deficient HLB-positive cluster and two zinc-deficient HLB-positive leaves were also misidentified as zinc-deficient HLB-negative samples. Table 5 also illustrates the confusion matrix of the classification results for the leaves of the artificial tree dataset. Analogous to the scatter plot in FIG. 10, the average of 0.33 HLB-positive samples and 0.67 zinc-deficient HLB-positive samples were misclassified in a three-fold cross validation. The overall accuracy of 95.5% was achieved in the four-class classification. Also, an overall HLB detection accuracy of 97% was achieved for leaves on the artificial tree dataset.

TABLE 3-5

Average number of samples in the leaves on the artificial tree dataset which were classified into the four classes and their corresponding classification accuracies and misclassification errors (%). The last row and column illustrate the sum of samples in the corresponding rows or columns

|  |  | Actual Class | | | | |
| --- | --- | --- | --- | --- | --- | --- |
|  |  | HLB+ | Zn Def. HLB+ | Zn Def. HLB− | HLB− | Sum |
| Prediction | HLB+ | 6.67 (92.29%) |  |  |  | 6.67 |
|  | Zn Def. HLB+ | 0.33 (4.71%) | 3.33 (83.25%) |  |  | 3.66 |
|  | Zn Def. HLB− |  | 0.67 (16.75%) | 4 (100%) |  | 4.67 |
|  | HLB− |  |  |  | 7 (100%) | 7 |
|  | Sum | 7 | 4 | 4 | 7 | 22 | iii. Field Experiment Results

Figure 23:
FIG. 23 shows images of each class of an in-field dataset of Example 3.

FIG. 23 shows three samples images (one sample image per class) acquired in the field experiment. The distance between the vision sensor and the target leaf in each image (specified with a red boundary) was exactly 80 cm. In FIG. 23, the target leaf in each image is indicated with a red boundary.

Table 3-6 shows the mean and SD gray value features which were extracted from the normalized histograms of the leaf images in the field experiment. Similar to the lab experimental results, the average of the feature values in the HLB-negative class was smaller than that of the HLB-positive class. Also, these features were mostly smaller for non-zinc deficient samples within the HLB-positive class.

TABLE 3-6

The mean and SD gray value features extracted from the normalized histogram of leaf sample images from the field dataset

|  |  |  | HLB-positive | | | | |
| --- | --- | --- | --- | --- | --- | --- | --- |
| HLB-negative | | | Non-zinc-deficient | | | Zinc-deficient | | |
| ID | μ | σ | ID | μ | σ | ID | μ | σ |
| 21 | 37.6 | 5.0 | 1 | 73.7 | 22.3 | 9 | 119.8 | 38.9 |
| 22 | 29.7 | 5.5 | 2 | 39.0 | 22.6 | 10 | 126.7 | 27.4 |
| 23 | 37.0 | 7.0 | 3 | 89.3 | 38.9 | 11 | 105.4 | 38.5 |
| 24 | 33.4 | 6.9 | 4 | 45.1 | 22.1 | 15 | 159.2 | 69.3 |
| 25 | 32.8 | 5.9 | 5 | 57.4 | 16.5 | 16 | 122.1 | 37.4 |
| 26 | 29.1 | 6.4 | 6 | 96.1 | 24.5 | 17 | 211.6 | 58.1 |
| 27 | 44.2 | 9.5 | 7 | 40.5 | 10.5 | 18 | 126.6 | 72.0 |
| 28 | 29.3 | 6.3 | 8 | 86.5 | 37.6 | 20 | 127.1 | 40.2 |
| 29 | 29.8 | 6.8 | 12 | 94.2 | 28.1 |  |  |  |
| 30 | 26.4 | 3.9 | 13 | 69.1 | 27.5 |  |  |  |
|  |  |  | 14 | 73.5 | 18.9 |  |  |  |
|  |  |  | 19 | 78.0 | 50.3 |  |  |  |
| Average | 32.9 | 6.3 | Average | 70.2 | 26.7 | Average | 137.3 | 47.7 |

Figure 24:
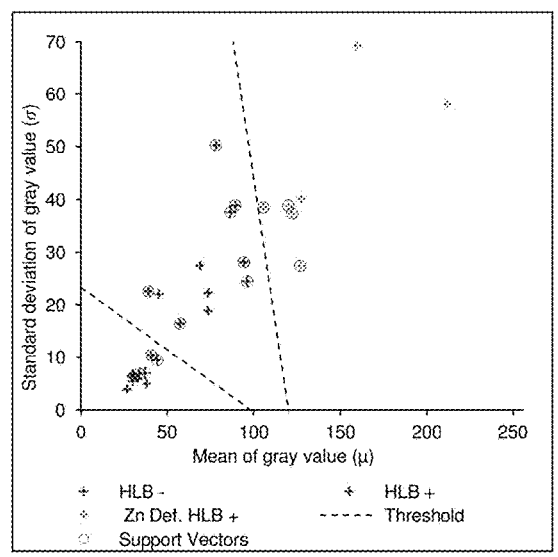
FIG. 24 is a scatter plot of samples based on the mean and SD of the gray values' for the images from the field experiment of Example 3.

A scatter plot of samples based on the mean and SD of the gray values' for the images from the field experiment is shown in FIG. 24, scatter plot of samples in the three classes based on their gray value mean and SD features of the normalized histograms of the target leaves from the field dataset. Sample #27 had the maximum SD (9.5) in the HLB-negative class which was smaller than the minimum SD in the HLB-positive class (10.5) which belonged to sample #7. However, the first linear threshold ($\sigma_1 = -0.24\mu + 23.32$) which was obtained by the maximum margin method was set above the sample #7 (HLB-positive). In other words, one HLB-positive sample was misclassified as HLB-negative in order to have a more general threshold. There were two subclasses of non-zinc-deficient and zinc-deficient samples within the HLB-positive class. Sample #6 in the non-zinc-deficient subclass had the maximum mean gray value of 96.1, while the minimum mean gray values in the zinc-deficient subclass was equal to 105.4 (sample #11). The second threshold ($\sigma_2 = -2.19\mu + 263.5$) was set between the two subclasses to separate the zinc-deficient samples from the non-zinc-deficient samples within the HLB-positive superclass. Using these two simple linear thresholds, all the samples were clustered in three classes of HLB-negative, HLB-positive and HLB-positive zinc-deficient with only one misidentified sample.

Table 3-7 includes the classification accuracies and one misclassification error for the field dataset. The overall three-class classification accuracy of 97% was achieved using the mean and SD features and the SVM classifier.

TABLE 3-7

Average number of samples in the field dataset which were classified into each of the three classes and their corresponding classification accuracies and misclassification errors (%). The last row and column illustrate the sum of samples in the corresponding rows or columns

|  |  | Actual class | | | |
| --- | --- | --- | --- | --- | --- |
|  |  | HLB+ | Zn Def. HLB+ | HLB− | Sum |
| Prediction | HLB+ | 3.67 (92%) |  |  | 3.67 |
|  | Zn Def. HLB+ |  | 3 (100%) |  | 3 |
|  | HLB− | 0.33 (8%) |  | 4 (100%) | 4.33 |
|  | Sum | 4 | 3 | 4 | 11 | iv. Observations—Part 1

The purpose of this study was to optimize the HLB detection performance of a previously introduced method, as detailed in Example 2 above, by developing a new vision sensor which could increase identification accuracy and decrease algorithm complexity and analysis time.

Our determination showed that the object depth had an extreme effect on the image histogram. However, there was a close relationship between the histogram features (mean and SD) and the object depth. Since these two histogram features were used for the classification purpose in this study, they could be easily calibrated and computed using the proposed regression equations when the object depth information is available. Depth cameras, such as an RGB-D (red, green, blue, and depth) camera, can measure the depth of each individual object in the image.

Khoshelham and Elberink (Khoshelham, K., Elberink, S. O., 2012, "Accuracy and resolution of kinect depth data for indoor mapping applications" in, *Sensors*, 12, 1437-1454) (Khoshelham and Elberink 2012) evaluated the resolution and accuracy of the depth information of a Kinect camera (Microsoft, Redmond, Wash.). They determined that the Kinect depth resolution varied from 2 mm (at a distance of 1 meter) to 25 mm (at a distance of 3 m). Since the maximum imaging distance in our application never goes beyond 3 m, a Kinect sensor can be used in our system to acquire the depth information with an acceptable resolution. Therefore, the mean and SD of the gray values of any leaf in a citrus tree image can be computed and used for HLB detection. This method will be used in the future in an on-the-go HLB diagnostic system. A comparison of three different distances between the sensor and leaf sample showed that the symptomatic areas in the three classes of HLB-negative, HLB-positive, and zinc-deficient samples were clearly distinguishable in all three distances; however, the maximum separation was achieved at a distance of 80 cm. The maximum range of the gray values (237) was also obtained at the distance of 80 cm, while it was found to be 219 and 229 at the distances of 60 cm and 100 cm, respectively. Additionally, the number of pixels in each pair of neighboring classes (HLB-negative and HLB-positive or HLB-positive and zinc-deficient), which had the same gray value decreased at a distance of 80 cm.

The results of identifying symptomatic areas using the color transform function confirmed that the positioning condition of the leaves did not have a significant effect on the identification accuracy. The results were slightly different for the leaves on the artificial tree condition (FIG. 20) because the distance between the leaves and the sensor was not exactly equal to 80 cm, and also the surfaces of the leaves were not precisely perpendicular to the line-of-sight of the camera. As a result, different locations on each leaf had different depths; still the symptomatic areas were distinctive for the leaves on the artificial tree condition as well. Because of the same reason, the mean and SD gray values of the leaves mostly decreased when their images were acquired on the artificial tree compared to the individual leaf positioning condition in which the distance between the leaves and the sensor was exactly equal to 80 cm (Table 3-3).

The mean and SD gray values of a histogram represent the overall intensity and root mean square (RMS) contrast in an image, as per Peli (Peli, E., 1990, "Contrast in complex images" in, *JOSA A*, 7, 2032-2040) (Peli 1990). Based on the results of this study, the mean gray values were smaller for the HLB-negative citrus leaves compared to the HLB-positive samples (tables 3-3 and 3-6). Since the HLB-positive citrus leaves had some starch accumulation and starch has the capability to rotate the polarization planar of polarized light, the designed sensor was able to highlight the HLB symptomatic areas on the HLB-infected leaves. These highlighted HLB-positive areas had brighter pixels which caused larger mean gray values for the HLB-positive leaves. However, the portion of HLB symptomatic area varied in each infected leaf and this variation influenced the mean gray values. Therefore, although the mean gray value was a satisfying feature for identifying HLB infection, the SD of the gray value was also used for this purpose to increase the accuracy. Still, the mean gray value alone was able to differentiate the zinc-deficient leaves from non-zinc-deficient samples within the HLB-positive class for the field experiment (FIG. 24). The SD of the gray value or RMS contrast of an image indicates the dispersion of gray values from the mean. The HLB-negative (non-zinc-deficient) samples did not have any high intensity areas, so their pixel values were mostly closer to the mean and consequently, they had smaller SD. On the contrary, the HLB-negative and zinc-deficient samples had both symptomatic (zinc or/and HLB) and non-symptomatic areas, and as a result, they had wider histogram curves and larger SD values. Accordingly, as the scatter plots in FIG. 21, FIG. 22, and FIG. 23 suggest, simple thresholds only in the SD could effectively separate HLB-negative samples from HLB-positive and zinc-deficient samples with zero error in all datasets.

Zinc deficiency develops extensive chlorosis between the veins which causes whitish yellow color in a symmetric pattern on the zinc-deficient citrus leaf. This symptom was originally brighter than the starch accumulation symptom in the HLB-positive leaves (FIG. 19 and FIG. 20) which usually caused larger mean gray values for zinc-deficient samples. Additionally, the SD values for non-zinc-deficient HLB-positive samples were usually smaller than zinc-deficient samples. A single threshold in SD for individual leaves or leaves on the artificial tree datasets (FIG. 21 and FIG. 22) could separate the HLB-positive leaves from the zinc-deficient samples with one misidentification; however, both of features were used with the maximum margin method to achieve a more general threshold.

The HLB-positive samples within the zinc-deficient class (lab experiment) had the averages of mean gray values equal to 135.1 and 118.2 for individual leaves and leaves on the artificial tree, respectively, while these averages were equal to 107.7 and 95.1 for the zinc-deficient HLB-negative samples (table 3). However, the best possible threshold in the mean gray value (e.g. $\mu$=82.95) would result in average clustering error rate of 35% for individual leaves and it would be worse for leaves on the artificial tree. The averages of the SD of the gray values for HLB-negative samples within the zinc-deficient class were also equal to 68.2 and 57.1 for individual leaves and leaves on the artificial tree, correspondingly, while these averages were equal to 53.4 and 48.1 for the HLB-positive samples. However the maximum clustering accuracy rate using the optimum threshold in the SD would not be over 70% for individual leaves. The coefficient of variation ($\sigma/\mu$) is a measure of relative variability which shows the dispersion of the gray values in relation to the mean, as per Kannan (Kannan, K., 1981, "Percentage coefficient of variation" in *CMFRI Special Publication*, 149) (Kannan 1981). The averages of the coefficients of variation values for the zinc-deficient HLB-positive samples were equal to 0.41 and 0.43 in individual leaves and leaves on the artificial tree datasets correspondingly, while they were equal to 0.64 and 0.60 for the zinc deficient HLB negative samples. The zinc-deficient HLB-positive samples included both HLB and zinc symptomatic areas, so they generally had smaller coefficients of variation which illustrated less gray value dispersion. The pixel values of the HLB symptomatic areas in an HLB-positive zinc-deficient sample filled the gap between the pixel values of the zinc-deficient symptomatic areas and healthy areas in the histogram of the leaf, and this was the reason for smaller coefficients of variation in this subclass. Therefore, it is necessary to use both the mean and SD features in HLB-positive samples identification within the zinc-deficient class. The slopes of the threshold lines between the HLB-positive and HLB-negative samples within the zinc-deficient class were analogous (FIG. 21 and FIG. 22) in both leaves positioning conditions datasets. Sample #11 was misidentified in both lab datasets, and sample #13 was also misidentified in the leaves on the artificial tree dataset. The coefficients of variation for both of these two samples were more similar to the HLB-negative zinc-deficient samples, so their misidentifications were unavoidable.

The zinc-deficient HLB-positive samples in all datasets had higher mean gray values in all three datasets. Since there was no zinc-deficient HLB-negative sample in the field dataset, a simple threshold within a comparatively wide margin ($\Delta\mu=9.3$) could also cluster these two classes with zero error.

Between all HLB detection methods, airborne image analysis can perform the fastest diagnosis in a large area. Li, Lee and Wang, et al. (Li, Lee, and Wang, et al. 2012) obtained the best accuracy (86.3%) using airborne hyperspectral imagery; however, their method was less accurate, more expensive, and more complicated comparing to the method presented in this study. Sankaran and Ehsani (Sankaran, S., Ehsani, R., 2012, "Detection of huanglongbing disease in citrus using fluorescence spectroscopy" in, *Trans. ASABE*, 55, 313-320)(Sankaran and Ehsani 2012) also reported the best overall accuracy of higher than 94% for field HLB detection; while the vision sensor in this study was able to identify HLB infection with less than 3% error. Additionally, compared with our previous study (Example 2 above), the HLB identification accuracy within the zinc-deficient samples increased significantly. Using only two simple statistical image descriptors in a step-by-step classification model required a computationally inexpensive analysis algorithm which is an advantage in design and development of the commercial diagnosis product.

v. Observations—Part 2

In this study, an HLB detection method was introduced which showed improved performance in different aspects compare to the previous studies. No sample preparation such as leaf collection or grinding was required in this method and the vision sensor could detect the infection without being in contact with leaves. Only two simple features were extracted from the leaf images and used for classification purposes. This simplification decreased the analysis expense and time, and facilitated the detection process. HLB-negative samples were classified with zero error in all three datasets. Not only was the zinc deficiency accurately detected, but also the HLB infection within the zinc-deficient leaves was identified with increased accuracies. The two major components of the vision sensor were 10 high power LEDs and an inexpensive camera, and the whole sensor was assembled with less than one-thousand dollars which made it an affordable diagnosis device even for small citrus growers. Two close relationships were found between the leaf depth in the image and the gray values' mean and SD features which were employed in leaf HLB status determination in this study. Using these two equations and a depth measurement sensor will enable this system to be used for on-the-go HLB diagnosis in future studies. Compared to our previous study, the HLB detection accuracy increased significantly in both zinc-deficient and non-zinc-deficient classes.

Example 4

Materials And Methods i. Data Collection

Two sample sets of Hamlin sweet orange leaves were collected from citrus trees at the Citrus Research and Education Center (CREC), University of Florida (Lake Alfred, Fla.). There were 60 citrus leaves in the first sample set comprising of 20 HLB-positive, 20 HLB-negative, 10 zinc-deficient HLB-positive, and 10 zinc-deficient HLB-negative samples. This sample set was used for comparing the images acquired by the proposed vision sensor with the images of the same samples which were obtained with another colour camera. The second sample set included another 30 samples containing 10 HLB-positive, 10 HLB-negative, 7 zinc-deficient HLB-positive, and 3 zinc-deficient HLB-negative. The second sample set was created to compare the images of the samples with the images of the same ground leaves. A qrt-PCR examination, as per Hansen, et al. (Hansen et al. 2008), was performed on all the 90 samples in both sample sets to confirm the HLB statuses of the leaves. The qrt-PCR test was done in the U.S. Sugar Corporation's Southern Gardens processing plant (Clewiston, Fla.).

ii. Image Acquisition

According to the results of the previous study, which is Example 3, starch in the HLB infected leaf was able to rotate the light polarization mainly around 600 nm. These results were used to develop an image acquisition system, as shown and described in FIGS. 11A, 11B, 12A, 12B, 13 and 14, and in Example 3, including a vision based sensor with the ability to highlight the symptomatic areas on an HLB infected leaf which contained excessive amount of starch. The vision sensor (vision based sensor) included a monochrome camera (DMK 23G445, TheImagingSource, Bremen, Germany) with high sensitivity at 591 nm, and 10 high power (10 W) narrow band LEDs (LZ4-00A100, LED Engine, San Jose, Calif.) concentrated at 591 nm which were mounted in a 13×19×15 cm wooden box. Five LED drivers (RCD-48, RECOM, Brooklyn, N.Y.) were used to power the LEDs. A wide lens with a 6 mm focal length was used for the camera to maximize its depth of field. Also one linear polarizer was installed in front of the camera's lens, and another polarizing film (Visible linear polarizing laminated film, Edmund Optics, Barrington, N.J.) with a perpendicular direction to the camera's filter was fixed in front of the LED panel. Using this setting, the camera only receives the minimum reflection.

iii. Imaging Conditions Evaluation

Images of citrus leaves in the first sample set were acquired in a completely dark room with the vision sensor from a distance of 80 cm because the minimum number of saturated pixels were achieved at this distance while pixel values were well distributed within the entire dynamic range. Therefore, the leaf samples only received the narrow band polarized light produced by the sensor. In order to evaluate the HLB identification efficiency of the sensor, another set of images from the same sample set were created using an RGB camera (EOS Rebel T2i, Canon, Tokyo, Japan) and with common indoor fluorescent light. All the RGB images were captured in the manual mode with a shutter speed of 0.04 s, a focal ratio of F4.5, and sensitivity of ISO800 to confirm the imaging condition uniformity and prevent the effect of camera settings on the evaluation results. The histograms of the red, green, blue, and grey (average of red, green, and blue) components of the RGB colour space and relative luminance (Y), blue-difference (Cb), and red-difference (Cr) components of YCbCr colour space were extracted from the symptomatic areas on each leaf and compared to the same symptomatic areas on the images captured by the vision sensor. Also mean and standard deviation features of the leaf area were extracted from the vision sensor images and the six colour components of the colour images, to visualize the samples in a 2-dimensional space and evaluate the separability between the four classes of HLB-positive, zinc-deficient HLB-positive, zinc-deficient HLB-negative, and HLB-negative leaves. A maximum margin approach, as per Bishop (Bishop 2006), was employed to determine the optimum thresholds between each pair of classes for the scatter plot of the samples images acquired by the vision sensor.

iv. Discriminant Analysis

In order to compare the separability of the four classes in the two imaging conditions, Fisher ratio was used as the separability index and it was calculated using the features extracted from the vision sensor images and all seven components of the RGB images (red, green, blue, grey, Y, Cb, Cr). Fisher ratio defines the ratio of the between-class variability to the within-class difference, as per Han, et al. (Han, Jeong-Su, Lee, Sang Wan, and, Bien, Zeungnam, 2013, "Feature subset selection using separability index matrix" in, *Information Sciences*, 223(0), 102-118. doi: http://dx.doi.org/10.1016/j.ins.2012.09.042)(Han, et al. 2013). Equation 23 shows the Fisher ratio for one feature in a 2-class problem.

$$F_{ij} = \frac{(\mu_i - \mu_j)^2}{(\sigma_i^2 + \sigma_j^2)} \quad (23)$$

Where $\mu_i$ and $\mu_j$ are the means and $\sigma_i$ and $\sigma_j$ are the standard deviations in class i and j. $F_{ij}$ shows the degree of the class separability in the direction of the corresponding feature. However, in order to improve the identification accuracy, two features (grey values' mean and standard deviation) were employed in this experiment and the effect of the two on a single separability index was needed. Therefore, a Fisher's linear discriminant analysis (LDA) was used to reduce the dimension of the feature vector to one dimensional for each pair of classes, as per Bishop (Bishop 2006) and then the Fisher ratio was calculated for the corresponding pair of classes. In Fisher's LDA (Equation 24), a function is employed to project the vector x down to a one-dimension vector (y).

$$y = w^T x \quad (24)$$

The projection method in Fisher's LDA was employed because it optimizes the weight vector (w) by maximizing the separation between the projected classes and minimizing variation within each projected class (Equation 25).

$$w \propto S_W^{-1}(m_2 - m_1) \quad (25)$$

Where $S_W$ is the total within class covariance matrix, and $m_1$ and $m_2$ are the mean of class one and two respectively. Using this projection, the Fisher ratio was computed between each pair of classes; however, the dataset included four classes and consequently a single separability index was required to describe the separability among all four classes. For this purpose, the arithmetic average of Fisher ratios for all possible pairs of classes was computed (Equation 26) and considered as the general separability index (F) for comparison of HLB identification efficiencies between the sensor images and the RGB images.

$$F = \frac{\sum_i^C \sum_j^C P_i P_j F_{ij}}{C(C-1) \sum_i^C \sum_j^C P_i P_j} \quad (26)$$

Where $P_i$ and $P_j$ are proportional to the number of samples in classes i and j, and C indicates the number of classes.

v. Samples Conditions Evaluation

In this part, the images of the leaves in the second sample set were compared to the same samples after being ground to investigate if the starch in ground infected leaves can be identified as accurately as unground leaves. For the grinding process, the samples were first placed in a ceramic mortar and freeze-dried with liquid nitrogen, as per Sankaran, et al. (Sankaran et al., 2010), and then they were ground using a ceramic pestle. The histograms of the whole leaves areas were acquired and compared with the histograms of the ground leaves. Also the gray values' means and standard deviations were extracted from both sample sets before and after being ground to visualize the samples in a 2-dimensional space. The separability indexes (Fisher ratio) as explained in the previous section were calculated for comparison purposes.

All the feature extractions and analyses were conducted in MATLAB™ (version R2011a, MathWorks™, Natick, Mass.). Also Excel (Microsoft™ Office™, Microsoft, Redmond, Wash.) was used to visualize the samples in scatter plots.

Results And Observations i. Dataset Validation

The number of required cycles for the fluorescent intensity to reach the threshold is considered as the cycle threshold (CT) in a qrt-PCR test. Li, et al. (Li, et al. 2006) suggested the CT value threshold of 33 to decide about the HLB status of a sample. According to their study, a CT value smaller than 33 indicates the HLB-positive status while a CT value over 33 shows no HLB infection for the corresponding sample. The measured CT values for the citrus leaves in the first sample set were illustrated in Table 4-1. Within the zinc-deficient class, 10 samples had the CT values below 33 and the rest of samples in this class had the CT values over 33. Therefore, the zinc-deficient class was divided into two subclasses of zinc-deficient HLB-positive and zinc-deficient HLB-negative classes.

TABLE 4-1

The cycle threshold (CT) values measured for the citrus leaves in the first sample set

| HLB Negative | | | |
|---|---|---|---|
| ID | CT Value | μ* | σ** |
| 21 | 40.0 | 38.3 | 5.7 |
| 22 | 40.0 | 28.4 | 4.2 |
| 23 | 40.0 | 49.5 | 8.0 |
| 24 | 40.0 | 26.5 | 3.7 |
| 25 | 40.0 | 20.9 | 4.7 |
| 26 | 40.0 | 26.8 | 4.9 |
| 27 | 40.0 | 28.0 | 3.2 |
| 28 | 40.0 | 26.3 | 4.8 |
| 29 | 40.0 | 23.1 | 3.8 |
| 30 | 40.0 | 23.7 | 3.8 |
| 31 | 40.0 | 35.8 | 4.0 |
| 32 | 40.0 | 34.3 | 5.1 |
| 33 | 40.0 | 30.2 | 4.8 |
| 34 | 36.5 | 29.3 | 6.0 |
| 35 | 40.0 | 33.7 | 4.7 |
| 36 | 40.0 | 26.2 | 5.6 |
| 37 | 40.0 | 31.9 | 5.3 |
| 38 | 40.0 | 36.6 | 5.1 |
| 39 | 40.0 | 41.8 | 4.5 |
| 40 | 40.0 | 34.3 | 6.6 |
| ID | CT Value | μ | σ |
| HLB-positive | | | |
| 41 | 28.0 | 48.5 | 14.8 |
| 42 | 23.2 | 51.5 | 14.9 |
| 43 | 25.4 | 78.7 | 38.9 |
| 44 | 32.3 | 59.7 | 18.8 |
| 45 | 21.9 | 63.8 | 26.9 |
| 46 | 21.5 | 49.3 | 13.6 |
| 47 | 22.3 | 46.2 | 12.7 |
| 48 | 26.5 | 53.4 | 13.5 |
| 49 | 24.4 | 52.2 | 23.7 |
| 50 | 23.1 | 51.8 | 15.6 |
| 51 | 21.9 | 81.2 | 23.0 |
| 52 | 30.8 | 47.8 | 21.1 |
| 53 | 24.8 | 56.1 | 18.7 |
| 54 | 22.0 | 76.0 | 17.8 |

TABLE 4-1-continued

The cycle threshold (CT) values measured for
the citrus leaves in the first sample set

| | | | |
|---|---|---|---|
| 55 | 22.7 | 57.5 | 11.0 |
| 56 | 23.2 | 64.1 | 17.3 |
| 57 | 26.6 | 69.0 | 15.5 |
| 58 | 21.9 | 103.5 | 39.9 |
| 59 | 22.8 | 47.8 | 12.1 |
| 60 | 21.9 | 52.9 | 18.4 |
| Zn Def. HLB-negative | | | |
| 1 | 40.0 | 84.7 | 65.8 |
| 3 | 37.7 | 110.3 | 65.7 |
| 4 | 40.0 | 89.4 | 58.6 |
| 5 | 40.0 | 107.9 | 58.6 |
| 7 | 40.0 | 121.4 | 85.4 |
| 10 | 40.0 | 127.5 | 77.5 |
| 12 | 40.0 | 119.4 | 82.2 |
| 15 | 40.0 | 98.0 | 55.3 |
| 16 | 40.0 | 128.6 | 69.2 |
| 17 | 40.0 | 89.3 | 63.7 |
| Zn Def. HLB-positive | | | |
| 2 | 24.9 | 100.4 | 42.6 |
| 6 | 23.3 | 114.8 | 37.1 |
| 8 | 23.6 | 121.0 | 44.1 |
| 9 | 22.6 | 213.8 | 59.0 |
| 11 | 27.8 | 102.9 | 62.4 |
| 13 | 24.6 | 140.9 | 65.7 |
| 14 | 23.2 | 134.5 | 64.3 |
| 18 | 22.1 | 98.7 | 44.5 |
| 19 | 24.3 | 162.1 | 64.5 |
| 20 | 21.4 | 162.3 | 49.7 |

*$\mu$: is the grey values' mean of the image captured by the vision sensor
**$\sigma$: is the grey values' standard deviation of the image captured by the vision sensor Table 4-2 also shows the CT values for the leaves in the second sample set. Seven samples within the zinc-deficient class had CT values smaller than 33 and three zinc-deficient samples had CT values greater than 33. So they were subcategorized into zinc-deficient HLB-positive and zinc-deficient HLB-negative classes, respectively.

TABLE 4-2

The cycle threshold (CT) values measured for
the citrus leaves in the second sample set HLB Negative

| ID | CT Value | $\mu$* | $\sigma$** |
|---|---|---|---|
| 21 | 40.0 | 23.3 | 8.2 |
| 22 | 40.0 | 27.6 | 9.5 |
| 23 | 40.0 | 27.8 | 9.1 |
| 24 | 40.0 | 20.9 | 6.7 |
| 25 | 40.0 | 22.8 | 8.7 |
| 26 | 40.0 | 28.7 | 8.3 |
| 27 | 40.0 | 37.8 | 8.9 |
| 28 | 40.0 | 23.2 | 8.7 |
| 29 | 40.0 | 27.5 | 9.0 |
| 30 | 40.0 | 18.8 | 9.1 |

| ID | CT Value | $\mu$ | $\sigma$ |
|---|---|---|---|
| HLB-positive | | | |
| 1 | 23.5 | 74.9 | 32.1 |
| 2 | 23.1 | 106.7 | 37.3 |
| 3 | 24.0 | 79.8 | 27.8 |
| 4 | 25.0 | 90.1 | 42.6 |
| 5 | 23.4 | 58.5 | 19.1 |
| 6 | 23.9 | 118.9 | 39.9 |
| 7 | 23.1 | 84.8 | 26.0 |
| 8 | 22.4 | 88.3 | 36.4 |
| 9 | 24.4 | 86.5 | 45.1 |
| 10 | 24.9 | 70.2 | 39.9 |

TABLE 4-2-continued

The cycle threshold (CT) values measured for
the citrus leaves in the second sample set

| | | | |
|---|---|---|---|
| Zn Def. HLB-negative | | | |
| 14 | 36.0 | 85.6 | 37.3 |
| 17 | 34.7 | 82.7 | 51.3 |
| 19 | 34.7 | 85.7 | 52.3 |
| Zn Def. HLB-positive | | | |
| 11 | 29.0 | 133.5 | 42.0 |
| 12 | 21.7 | 145.4 | 46.4 |
| 13 | 22.2 | 100.3 | 38.3 |
| 15 | 23.2 | 145.5 | 55.0 |
| 16 | 24.0 | 97.9 | 31.0 |
| 18 | 29.0 | 131.4 | 45.9 |
| 20 | 23.6 | 87.1 | 54.6 |

Figure 25:
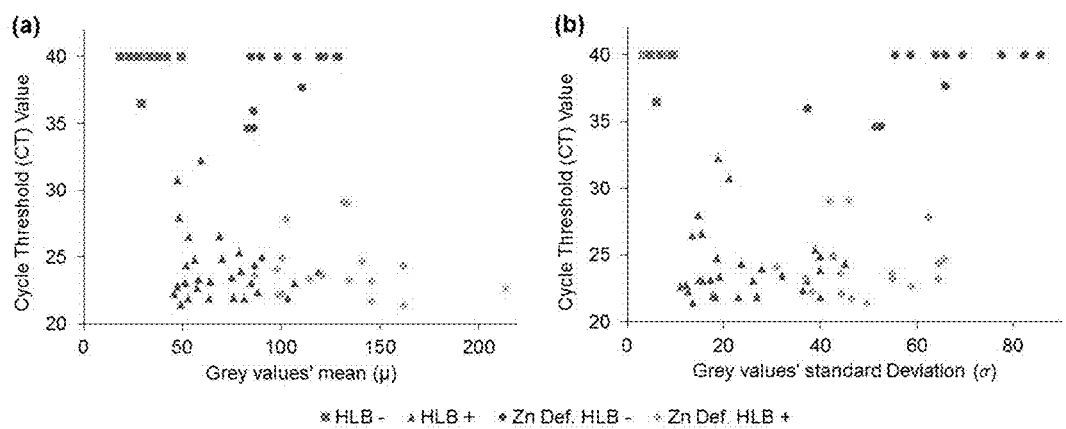
FIG. 25 is a series of scatter plots of samples in four classes based on their grey values features and cycle threshold (CT) values, for Example 4.

*$\mu$: is the grey values' mean of the image captured by the vision sensor before grinding
$\sigma$: is the grey values' standard deviation of the image captured by the vision sensor before grinding In order to examine the relationships between the grey values features (means and standard deviations) and CT values, two correlation analyses were conducted in MINITAB (version 15, Minitab Inc., State College, Pa.). The Pearson coefficients of −0.493 and −0.244 were achieved for the correlations between means and CTs, and standard deviations and CTs, respectively. Since the coefficients were negative in both correlations analyses, it can be concluded that the CT values generally tended to increase as the grey values features decreases. The absolute coefficient value also tells the strength of a relationship between two variables where a perfect relationship is indicated by one, and zero means no relationship at all. Since the obtained Pearson coefficients were closer to zero than one, it can be concluded that there is no strong relationship between CT values and the grey values features. It can be also inferred from the scatter plots in FIG. 25 (Parts a and b). FIG. 25** shows scatter plots of samples in four classes based on their grey values features and cycle threshold (CT) values; (Part a): grey values' means and CTs; (Part b): grey values' standard deviations and CTs.

Basically, there is no direct correlation between degree of symptoms of a given leaf sample and its CT values. The bacteria are very unevenly distributed throughout an HLB affected tree, so variations per samples can be quite large. Additionally, HLB symptoms may show in different ways, so it is impossible to define which symptoms show up first to be correlated with CT values, as per Gottwald (Gottwald 2010). The vision sensor (vision based sensor) in this Example was designed to highlight the accumulation of starch; however, starch can vary drastically over a certain threshold, and it is impractical to correlate the starch accumulation to CT value in a single sample. However, the CT value can be correlated to the number of symptomatic areas on an entire tree including roots. The amount of starch accumulation indicates that HLB infection is present somewhere in the tree and this can be away from the bacterial infection, while the CT value reveals the level of infection in that particular leaf sample. As the correlation analyses confirmed, there were no strong correlations between CT values and grey values' means or standard deviations. The method presented in this paper was not meant to be quantitative in terms of bacteria but rather in terms of the presence of HLB infection in a tree.

ii. Comparison of Imaging Conditions

Figure 26:
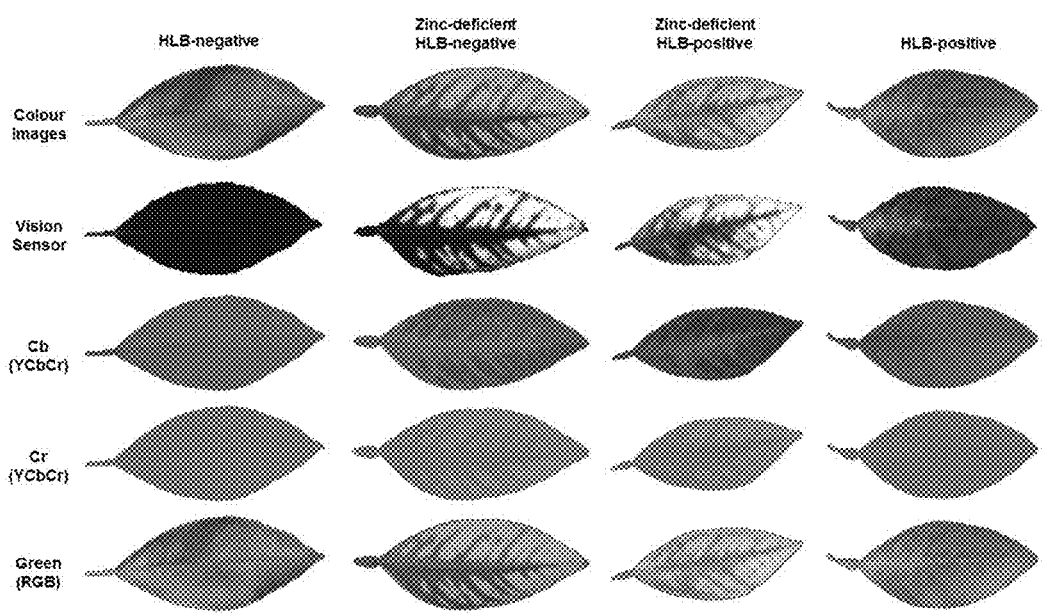
FIG. 26 is a series of colour photos of leaf samples in four classes and their corresponding monochrome images, for Example 4.

Four sample images (one from each class) acquired with the vision sensor and their corresponding colour components extracted from the colour images are shown in FIG. 26. FIG.

26 shows colour photos of leaves' samples in four classes and their corresponding monochrome images captured by the vision sensor and extracted from the colour images, Cb: blue difference (YCbCr); Cr: red difference (YCbCr).

The healthy, HLB-positive, and zinc-deficient symptomatic areas appeared more distinctive in the images acquired with the vision sensor, compared to the other colour components. The separability indices (arithmetic averages of Fisher ratios) of 0.528, 0.201, 0.196, 0.136, 0.135, 0.134, 0.114, 0.003 were achieved for vision sensor, Cb component (YCbCr), Cr component (YCbCr), green component (RGB), Y component (YCbCr), grey component (RGB), red component (RGB), and blue component (RGB) respectively. The separability index achieved for the vision sensor is more than 2.5 times greater than the runner up in the ranking which was the Cb component of colour images. This result confirmed the exceptional capability of the vision sensor to highlight the HLB symptom and differentiate it from HLB-negative and zinc-deficient areas.

Figure 27:
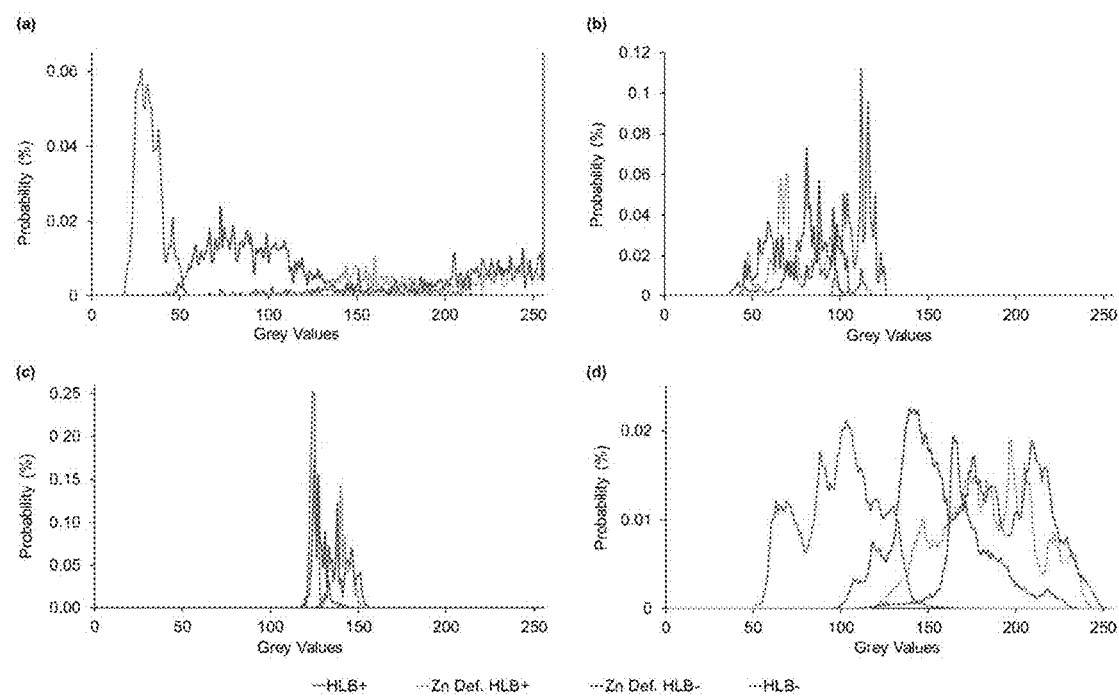
FIG. 27 is show histograms of four classes' symptomatic areas for Example 4.

The normalized histograms of the symptomatic areas in the images acquired with the vision sensor and top three components of colour images are shown in FIG. 27 (Parts a-d). FIG. 27, Parts a-d, show histograms of four classes' symptomatic areas; (Part a): vision sensor images; (Part b): colour images, blue difference (Cb) component of YCbCr; (Part c): colour images, red difference (Cr) component of YCbCr; (Part d): colour images, green component of RGB. HLB+: infected with Huanglongbing; Zn Def. HLB+: zinc deficient and infected with Huanglongbing; Zn Def. HLB−: zinc deficient but not infected with Huanglongbing; HLB−: healthy.

In order to conduct a valid comparison, the same symptomatic areas on the leaves' images were marked and used for creating the histograms. The pixel values belonging to different symptomatic areas were well distributed on the grey scale range (0-255) in the images of the vision sensor, while they are concentrated in limited ranges of grey values for the Cb and Cr components. Table 4-3 includes the exact overlap percentages between every pair of classes for the vision sensor images and the top three colour images components. Comparing to the colour components, the vision sensor histograms had minimum overlaps between every pair of classes except for the pair of HLB+/HLB− within the zinc deficient class HLB-negative symptomatic area had zero overlap with zinc deficient classes and only 1.74% overlaps with HLB-positive symptomatic areas in the images of the vision sensor while these percentages increased notably for the colour components.

TABLE 4-3

Percentages of overlaps between the histograms of every pairs of classes in the images acquired with the vision sensor and top three components of colour images.

|  | HLB+ | Zn Def. HLB+ | Zn Def. HLB− |
| --- | --- | --- | --- |
| Vision Sensor | | | |
| HLB− | 1.74% | 0.00% | 0.00% |
| HLB+ |  | 11.87% | 12.01% |
| Zn Def. HLB+ |  |  | 80.98% |
| Red difference (Cr) component of YCbCr | | | |
| HLB− | 22.37% | 4.06% | 4.07% |
| HLB+ |  | 51.66% | 46.22% |
| Zn Def. HLB+ |  |  | 67.36% |

TABLE 4-3-continued

Percentages of overlaps between the histograms of every pairs of classes in the images acquired with the vision sensor and top three components of colour images.

|  | HLB+ | Zn Def. HLB+ | Zn Def. HLB− |
| --- | --- | --- | --- |
| Blue difference (Cb) component of YCbCr | | | |
| HLB− | 56.21% | 1.29% | 0.44% |
| HLB+ |  | 14.62% | 12.23% |
| Zn Def. HLB+ |  |  | 76.05% |
| Green component of RGB | | | |
| HLB− | 19.98% | 4.92% | 1.88% |
| HLB+ |  | 54.75% | 38.68% |
| Zn Def. HLB+ |  |  | 77.45% |

Figure 28:
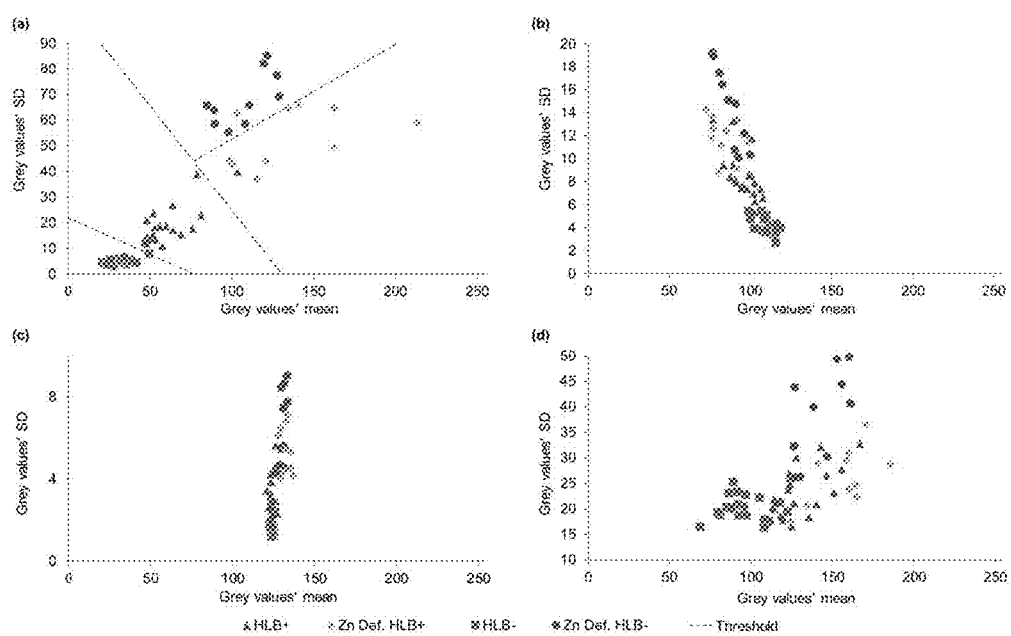
FIG. 28 shows a series of scatter plots for Example 4.

HLB+: infected with Huanglongbing;
Zn Def. HLB+: zinc deficient and infected with Huanglongbing;
Zn Def. HLB−: zinc deficient but not infected with Huanglongbing;
HLB−: healthy The scatter plots of leaf areas in the vision sensor and the top three components of the colour images are illustrated in FIG. 28 (Parts a-d). FIG. 28 shows scatter plots of samples in four classes based on their means and standard deviations; (Part a): vision sensor images; (Part b): colour images, blue difference (Cb) component of YCbCr; (Part c): colour images, red difference (Cr) component of YCbCr; (Part d): colour images, green component of RGB. HLB+: infected with Huanglongbing; Zn Def. HLB+: zinc deficient and infected with Huanglongbing; Zn Def. HLB−: zinc deficient but not infected with Huanglongbing; HLB−: healthy.

As the plots suggest, four classes of the leaf samples are more distinctive in the images of the vision sensor compared to the colour image components. The thresholds in the vision sensor scatter plot divided the four classes with maximum possible margin and minimum number of mis-classified samples. In order to find the best thresholds, the maximum margin method was applied in three steps sequentially. At the first step, it determined the optimum threshold between HLB-negative samples and the rest of the dataset. At the second step, the threshold between HLB-positive and zinc-deficient samples was acquired. Finally, at the third step, the best separating threshold between HLB-positive and HLB-negative samples within the zinc-deficient class was obtained. The HLB-negative samples in the vision sensor images had smaller means (from 20 to 50) compared to the other classes. There were neither HLB nor zinc deficiency symptomatic areas on the HLB-negative leaves. Therefore, they reflected the polarized light with the same polarization planar direction as was illuminated with and this reflection was filtered by the polarizing filter in front of the camera. The means of HLB-negative samples in other colour components, however, were over 68 which usually overlapped with the samples in other classes because the illumination and reflection were not filtered in their image acquisition process. The HLB-positive samples, on the other hand, had greater means and SDs in the vision sensor scatter plot compared to the HLB-negative samples. Starch accumulation in the HLB-positive samples rotated the polarization plane of light and, therefore, the symptomatic areas were brighter in the vision sensor images. The zinc deficiency areas had the brightest pixels in the vision sensor images, while in the other colour components, their pixel values overlapped with other classes. Zinc-deficient leaves contain starch (with different molecular properties than those of HLB-positive leaves) at some level higher than healthy leaves but less than HLB-positive leaves, as per Gonzalez, Reyes, et al. (Gonzalez, Pedro, Reyes, Jose, and, Etxeberria, Ed., 2011, "Starch Analysis of HLB-affected and Control Healthy Citrus Leaves Reveal Variations in the Amylose/Amylopectin Ratio" in, Paper presented at the Proc. Fla. State Hort. Soc.) (Gonzalez, Reyes, et al. 2011).

This might be one explanation for the high pixel values at zinc-deficient symptomatic areas. Within the zinc deficient super class, the HLB-positive samples had greater means and smaller SDs compared to the HLB-negative sample in vision sensor images. The zinc-deficient HLB-positive samples included both zinc deficiency and HLB symptoms so they had larger means. On the other hand, the pixel values belonging to the HLB symptomatic areas (mid-grey pixels) filled the gap between zinc deficient areas (bright pixels) and healthy parts (dark pixels) and as a result, the HLB-positive samples had smaller SDs in the zinc-deficient super class. The zinc-deficient HLB-negative samples had greater SDs in colour components as well, but their means were analogues to the HLB-positive samples which affects the classification accuracy. It can be concluded from the scatter plots in FIG. 28 that the vision sensor provided the best separations between the four classes.

Figure 29:
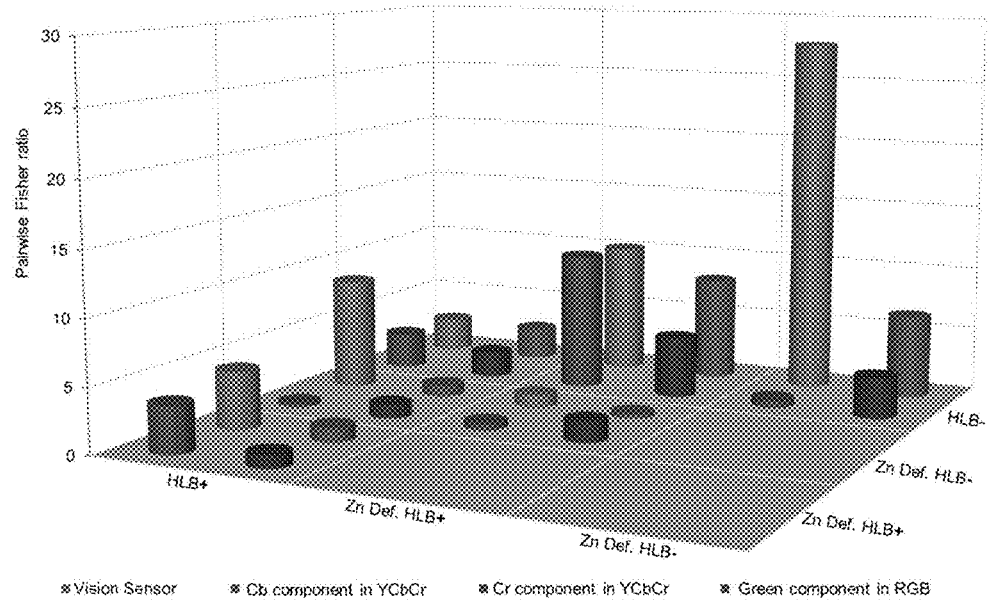
FIG. 29 shows a diagram of a comparison of the pairwise fisher ratios for Example 4.

The pairwise Fisher ratios for the vision sensor and the top three components of colour images are illustrated in FIG. 29. FIG. 29 shows a comparison of the pairwise fisher ratios (as the separability indexes) achieved using mean and standard deviation features for the vision sensor and top three colour components, Cb: blue difference (YCbCr); Cr: red difference (YCbCr).

Since the dataset included four different classes, a total number of six pairwise comparisons were conducted. The vision sensor had better separability indexes between the HLB-positive class and both zinc-deficient sub classes as well as between HLB-negative and zinc-deficient HLB-negative classes. The vision sensor and all three colour components presented comparable separability between HLB-positive and HLB-negative classes, still a better separability can be seen in the scatter plot of the vision sensor (FIG. 28). The separability indices between the HLB-positive and HLB-negative classes within the zinc deficient class were relatively smaller compared to the other pairs of classes; while the green component produced slightly better separability than the vision sensor. It is likely that starch in the zinc-deficient HLB-positive samples is more of a mixture of HLB-positive and zinc-deficient properties, which is more difficult to discern.

iii. Comparison of Sample Conditions

Figure 30:
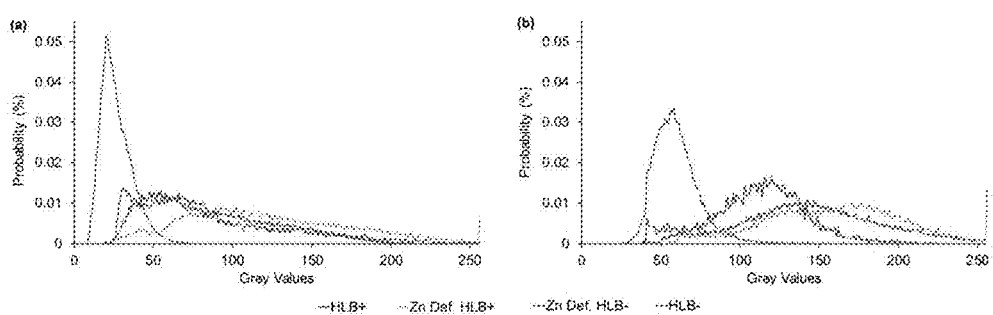
FIG. 30 is a series of histograms for Example 4.

The normalized histograms of the entire leaf areas (not only the symptomatic areas) in the vision sensor images are shown in FIG. 30 (Parts a and b) before and after grinding and in four different classes. FIG. 30 shows histograms of the entire leaves' areas in four classes; (Part a): before grinding; (Part b): after grinding. HLB+: infected with Huanglongbing; Zn Def. HLB+: zinc deficient and infected with Huanglongbing; Zn Def. HLB−: zinc deficient but not infected with Huanglongbing; HLB−: healthy. It can be seen in the normalized histograms that the leaf images became brighter after grinding.

In general, the back side of the citrus leaf is brighter compared to its front side, likely due to the thinner cuticle and more compact epidermis. After grinding, both sides of the leaves were mixed so the ground leaves looked brighter. The histograms of HLB-negative samples were noticeably detectable from the other classes in both plots. The histogram of the HLB-positive samples was comparable to the zinc-deficient HLB-negative class before grinding; but after grinding the HLB-positive samples became brighter. The accumulated starch was more visible after grinding and this could be a reason for more brightness in ground leaves images. According to FIG. 30, zinc-deficient HLB-positive samples were the brightest class either before grinding or after grinding. Including both HLB and zinc deficiency symptoms made them brighter in average compared to the other classes.

Figure 31:
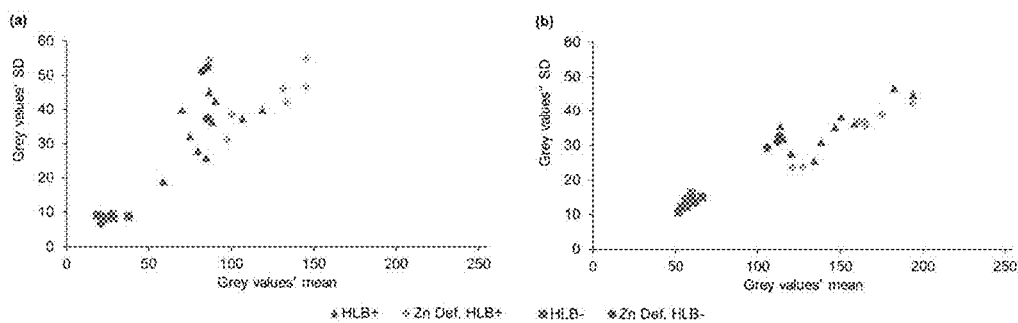
FIG. 31 is another series of scatterplots for Example 4.

The scatter plots of samples before and after grinding are illustrated in FIG. 31 (Parts a and b). FIG. 31 shows scatter plots of samples in four classes based on their mean and standard deviation; (Part a): before grinding; (Part b): after grinding. HLB+: infected with Huanglongbing; Zn Def. HLB+: zinc deficient and infected with Huanglongbing; Zn Def. HLB−: zinc deficient but not infected with Huanglongbing; HLB−: healthy.

As the histograms in FIG. 30 also suggest, the grey values' means generally increased after grinding but the range of SDs variation decreased. Before grinding, the means of the HLB-positive samples were close to the means of the zinc-deficient HLB-negative leaves; however, after being ground their means were more similar to the zinc-deficient HLB-positive samples. This is another reason that supports the unique starch characteristic of rotating the polarization plane of light and becoming brighter in the images acquired by the vision sensor. Since the samples from both HLB positive and zinc-deficient HLB-positive classes included excessive levels of starch, and their starch content were more visible after being ground, they had more high-intensity pixels and consequently greater grey values' means also.

Figure 32:
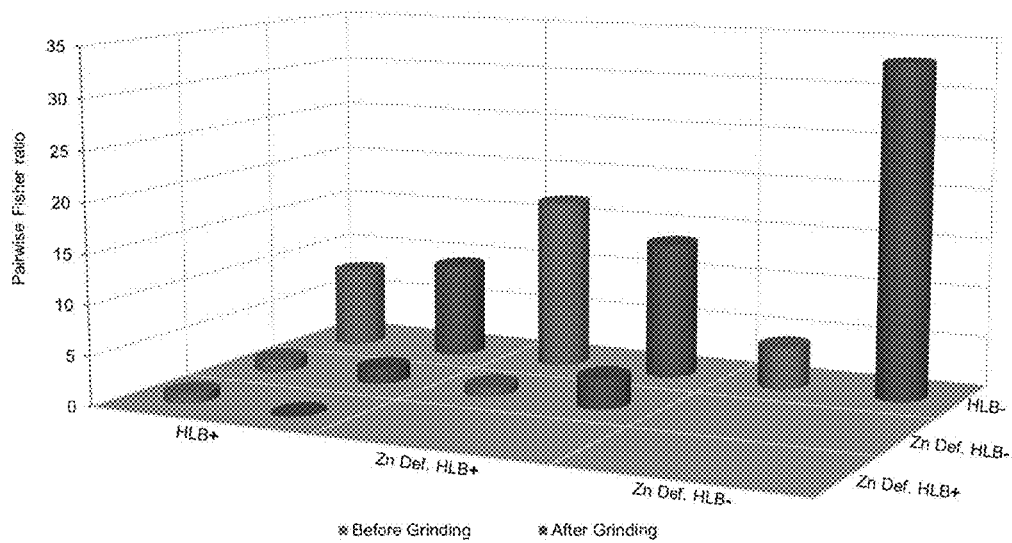
FIG. 32 is a diagram of a pairwise fisher ratio and arithmetic average of Fisher ratio as the separability index for Example 4.

The pairwise Fisher ratios before and after grinding are plotted in FIG. 32. FIG. 32 shows a pairwise fisher ratio and arithmetic average of Fisher ratio as the separability index achieved using mean and standard deviation features before and after grinding. HLB+: infected with Huanglongbing; Zn Def. HLB+: zinc deficient and infected with Huanglongbing; Zn Def. HLB−: zinc deficient but not infected with Huanglongbing; HLB−: healthy.

The separability indexes (arithmetic averages of Fisher ratios) of 0.415, and 0.559 were achieved for samples before and after being ground, respectively. According to FIG. 32, the HLB-positive and HLB-negative samples were better separated in the ground leaves images, regardless of their zinc deficiency. Again that was due to more visibility of starch after grinding. HLB-positive and zinc-deficient HLB-positive classes were hardly separable after grinding (Fisher ratio <0.1). On average, the grey values means increased by 72% for HLB-positive samples after grinding, while this percentage was about 32% for zinc deficient samples. One reason might be that HLB symptom overrode zinc deficiency symptom in zinc-deficient HLB-positive ground leaves, and as a result only HLB symptoms could be seen after grinding. On the other hand, the average of grey values' SDs increased by 7% for the HLB-positive samples after grinding, while it decreased by 25% for the zinc-deficient leaves. In other words, after grinding the zinc-deficient leaves had smoother images, while there was more contrast in the images of the HLB-positive samples which happened due to the increased difference between the pixel values of HLB symptomatic and healthy areas. This was another proof supporting the outstanding capability of the vision sensor to highlight the starch accumulation in citrus leaf.

The separability index between the HLB-positive and zinc-deficient HLB-negative samples did not change much after being ground. However, a huge increase in the Fisher ratio happened for the pair of HLB-negative and zinc-deficient HLB-negative classes which also influenced the increased arithmetic average of the Fisher ratios for ground leaves. It can be concluded that the four classes were generally better separated after grinding; however, the separability before grinding was acceptable enough for a non-destructive on-the-go HLB diagnosis application.

Among different HLB identification approaches, aerial imaging systems can conduct the quickest diagnosis on a large scale grove, as per Li, Lee and Li, et al. (Li, Lee and Li, et al. 2012); however, comparing to the method introduced in this study, airborne image analysis is less accurate, more costly, and more complicated. The laboratory based diagnosis methods such as qrt-PCR test, as per Hansen, et al. (Hansen et al. 2008), and starch measurement, as per Gonzalez, et al. (Gonzalez et al. 2012), can perform the most accurate HLB identification; however, these methods can be only conducted in a laboratory, they are time consuming and they need an additional step of sample collection, while the vision sensor in this paper can handle a real-time on-the-go diagnosis. Also it can be easily equipped with a Differential Global Positioning System (DGPS) to produce the HLB status map of the grove.

Observations

A new prototype vision sensor was introduced in this study, i.e., this Example, which was able to recognize HLB infection with a high accuracy. One of the main advantages of this vision sensor was the ability to highlight the symptomatic areas by employing a customized illumination system and proper use of polarizing filters. The other important advantage was the non-destructive diagnosis capability of this sensor in which no sample preparation was required. Two experiments were designed to assess these two features of the sensor. The results confirmed that the narrow band polarized illumination at 591 nm significantly increased the diagnosis accuracy. Additionally, it was shown that grinding the citrus leaf samples could increase the separability index; however, the images of unground leaves were informative enough for a non-destructive on-the-go diagnosis application. Another advantage of this sensor was its affordability. This sensor included a few inexpensive components which makes it a reasonably priced approach for every citrus grower. The total cost of the sensor components was less than one thousand dollars. This sensor can help the growers conduct a constant monitoring of their grove and prevent huge losses from massive incurable HLB infection.

The implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

Selected tasks in software, according to embodiments of the invention, could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, non-transitory storage media such as a magnetic hard-disk and/or removable media, for storing instructions and/or data. Optionally, a network connection is provided as well. A display and/or a user input device such as a keyboard or mouse are optionally provided as well.

For example, any combination of one or more non-transitory computer readable (storage) medium(s) may be utilized in accordance with the above-listed embodiments of the present invention. The non-transitory computer readable (storage) medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

As will be understood with reference to the paragraphs and the referenced drawings, provided above, various embodiments of computer-implemented methods are provided herein, some of which can be performed by various embodiments of apparatuses and systems described herein and some of which can be performed according to instructions stored in non-transitory computer-readable storage media described herein. Still, some embodiments of computer-implemented methods provided herein can be performed by other apparatuses or systems and can be performed according to instructions stored in computer-readable storage media other than that described herein, as will become apparent to those having skill in the art with reference to the embodiments described herein. Any reference to systems and computer-readable storage media with respect to the following computer-implemented methods is provided for explanatory purposes, and is not intended to limit any of such systems and any of such non-transitory computer-readable storage media with regard to embodiments of computer-implemented methods described above. Likewise, any reference to the following computer-implemented methods with respect to systems and computer-readable storage media is provided for explanatory purposes, and is not intended to limit any of such computer-implemented methods disclosed herein.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The above-described processes including portions thereof can be performed by software, hardware and combinations thereof. These processes and portions thereof can be performed by computers, computer-type devices, workstations, processors, micro-processors, other electronic searching tools and memory and other non-transitory storage-type devices associated therewith. The processes and portions thereof can also be embodied in programmable non-transitory storage media, for example, compact discs (CDs) or other discs including magnetic, optical, etc., readable by a machine or the like, or other computer usable storage media, including magnetic, optical, or semiconductor storage, or other source of electronic signals.

The processes (methods) and systems, including components thereof, herein have been described with exemplary reference to specific hardware and software. The processes (methods) have been described as exemplary, whereby specific steps and their order can be omitted and/or changed by persons of ordinary skill in the art to reduce these embodiments to practice without undue experimentation. The processes (methods) and systems have been described in a manner sufficient to enable persons of ordinary skill in the art to readily adapt other hardware and software as may be needed to reduce any of the embodiments to practice without undue experimentation and using conventional techniques.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A method for detecting starch accumulation-deficient trees comprising:
    (a) illuminating at least one tree leaf with a polarized light at a first reference plane;
    (b) obtaining light reflected from the at least tree leaf having been polarized at a second reference plane, the second reference plane at a predetermined angle relative to the first reference plane; and,
    (c) generating at least one image from the obtained light, and analyzing the image for a correlation to starch accumulation in the at least one tree leaf.

2. The method of claim 1, wherein the correlation to starch accumulation is in accordance with predetermined starch concentration values in leaves.

3. The method of claim 2, additionally comprising: obtaining a starch concentration value for the at least one tree leaf, the obtained starch concentration value based on the correlation of starch accumulation in the at least one tree leaf with the predetermined starch concentrations, and analyzing the obtained starch concentration value with respect to starch concentration values of leaves of starch-accumulation deficient trees including Huanglongbing (HLB)-symptomatic trees.

4. The method of claim 2, wherein the at least one image includes gray values and the gray values are analyzed for the correlation to starch accumulation in the at least one tree leaf.

5. The method of claim 4, wherein the at least one image includes pixels, and each of the pixels corresponds to at least one of the gray values.

6. The method of claim 1, wherein the predetermined angle for the second reference plane is approximately 90 degrees from the first reference plane.

7. The method of claim 1, wherein the polarized light is at a wavelength of approximately 550 nanometers (nm) to approximately 650 nm.

8. The method of claim 7, wherein the polarized light is at a wavelength of approximately 590 nm to approximately 610 nm.

9. The method of claim 8, wherein the polarized light is at a wavelength of approximately 600 nm.

10. The method of claim 8, wherein the polarized light is at a wavelength of approximately 591 nm.

11. The method of claim 1, wherein the at least one tree leaf is from a Citrus tree.

12. A system for detecting starch accumulation-deficient trees comprising:
    (a) a polarized light source, for illuminating a tree leaf, the polarized light from the polarized light source emitted at a first reference plane;
    (b) a polarizer at second plane at an angle relative to the first reference plane;

(c) at least one sensor in communication with the polarizer for detecting the intensity of received reflected light which is filtered by the polarizer;

(d) an image processor in communication with the at least one sensor for producing images based on the intensity of the received reflected light and, analyzing the image for a correlation to starch accumulation in the at least one tree leaf.

13. The system of claim 12, wherein the image processor is configured for correlating the starch- accumulation with starch accumulation values for starch accumulation deficient trees including Huanglongbing (HLB)-symptomatic trees.

14. The system of claim 12, wherein the at least one sensor, and the image processor are associated with a charge coupled device (CCD) camera, and the image processor generates images from the received reflected light.

15. The system of claim 12, wherein the image processor generates an image including pixels, each of the pixels including at least one gray scale value, each of the gray scale values with respect to a reference gray scale.

16. The system of claim 15, wherein the image processor includes at least one processor for analyzing reach of the pixel gray scale values with respect to the reference gray scale, the reference gray scale including gray scale values associated with leaves of a Huanglongbing (HLB) symptomatic tree.

17. The system of claim 16, wherein the polarizer includes at least one second polarized filter at the second plane.

18. The system of claim 17, wherein the light source emits light at a wavelength of approximately 550 nanometers (nm) to approximately 650 nm.

19. The system of claim 18, wherein the light source emits light at a wavelength of approximately 590 nm to approximately 610 nm.

20. The system of claim 19, wherein the light source emits light at a wavelength of approximately 600 nm.

21. The system of claim 19, wherein the light source emits light at a wavelength of approximately 591 nm.

22. The system of claim 16, wherein the second plane is oriented approximately 90 degrees from the first reference plane.

23. The system of claim 12, wherein the polarized light source includes a light source coupled to at least one first polarizing filter oriented to define the first reference plane.

24. A computer usable non-transitory storage medium having a computer program embodied thereon for causing a suitable programmed system to detect birefringent materials in a acquired image, by performing the following steps when such program is executed on the system, the steps comprising:

generating gray scale images with gray values from acquired images of citrus leaves; translating the gray values to at least one scatterplot; and, applying predetermined thresholds on the scatterplot for starch accumulation values for citrus leaves.

25. The computer usable non-transitory storage medium of claim 24, wherein, the applying thresholds includes, applying a threshold for starch accumulation values associated with leaves of a Huanglongbing (HLB)-symptomatic tree.

26. The computer usable non-transitory storage medium of claim 24, wherein the gray values include the mean and standard deviation (SD), which for the respective vertical (y) and horizontal (x) axes of a histogram.

27. The computer usable non-transitory storage medium of claim 26, wherein, the applying thresholds includes, applying a threshold for starch accumulation values associated with leaves of a Huanglongbing (HLB)-symptomatic tree.

28. The computer usable non-transitory storage medium of claim 27, wherein, the predetermined thresholds are determined by machine learning.

29. The computer usable non-transitory storage medium of claim 26, wherein the acquired images include pixels, each of the pixels having a gray value.

* * * * *